US012653636B2

(12) United States Patent
Comenencia Ortiz et al.

(10) Patent No.: US 12,653,636 B2
(45) Date of Patent: Jun. 16, 2026

(54) DEVICES AND METHODS FOR COMPACT, REDUNDANT INDUCTIVE FORCE SENSOR

(71) Applicant: Intuitive Surgical Operations, Inc., Sunnyvale, CA (US)

(72) Inventors: Lizmarie Comenencia Ortiz, San Bruno, CA (US); David I. Moreira Ridsdale, Saratoga, CA (US); Alan W. Petersen, Cupertino, CA (US); Harsukhdeep S. Ratia, Los Altos Hills, CA (US); Sharathchandra Somayaji, Santa Clara, CA (US); Ashwinram Suresh, San Jose, CA (US); Zhou Ye, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 407 days.

(21) Appl. No.: 18/026,040

(22) PCT Filed: Sep. 10, 2021

(86) PCT No.: PCT/US2021/049792
§ 371 (c)(1),
(2) Date: Mar. 13, 2023

(87) PCT Pub. No.: WO2022/056213
PCT Pub. Date: Mar. 17, 2022

(65) Prior Publication Data
US 2023/0363849 A1     Nov. 16, 2023

Related U.S. Application Data

(60) Provisional application No. 63/077,833, filed on Sep. 14, 2020.

(51) Int. Cl.
A61B 34/00     (2016.01)
A61B 34/30     (2016.01)
A61B 90/00     (2016.01)

(52) U.S. Cl.
CPC .............. *A61B 90/06* (2016.02); *A61B 34/30* (2016.02); *A61B 2090/064* (2016.02)

(58) Field of Classification Search
CPC .......................... A61B 2090/064; A61B 90/06
See application file for complete search history.

(56) References Cited

U.S. PATENT DOCUMENTS

| | | | |
|---|---|---|---|
| 2,623,386 A | 12/1952 | Baker | |
| 3,325,761 A | 6/1967 | Mclellan | |
| (Continued) | | | |

FOREIGN PATENT DOCUMENTS

| | | | |
|---|---|---|---|
| CN | 101448464 A | 6/2009 | |
| CN | 103717355 A | 4/2014 | |
| (Continued) | | | |

OTHER PUBLICATIONS

Office Action for Chinese Application No. CN202080066153, mailed Oct. 12, 2024, 15 pages.
Office Action for Chinese Application No. CN202080066153.X, mailed Nov. 30, 2023, 20 pages.
(Continued)

*Primary Examiner* — Allen Porter

(57) ABSTRACT

A medical device includes a mechanical structure and a force sensor unit. The force sensor unit comprises a mounting bracket, a first rod, a second rod, a first magnet, a second magnet, a first coil coupled to the mounting bracket, and a second coil coupled to the mounting bracket. The first rod and the second rod each have a center axis defined between a proximal and distal portion of the respective first and second rods. The center axis of the second rod is noncoaxial with the center axis of the first rod. The first magnet is coupled to the first rod and translates within the first coil (Continued)

along the center axis of the first rod. Similarly, the second magnet is coupled to the second rod and translates within the second coil along the center axis of the second rod.

28 Claims, 32 Drawing Sheets

(56) References Cited

U.S. PATENT DOCUMENTS

| | | | |
|---|---|---|---|
| 3,358,511 A | 12/1967 | David | |
| 4,064,758 A | 12/1977 | Harrison | |
| 4,146,864 A | 3/1979 | Bethe | |
| 4,507,170 A | 3/1985 | Myhre | |
| 5,024,107 A | 6/1991 | Bethe | |
| 5,333,504 A | 8/1994 | Lutz et al. | |
| 5,625,576 A | 4/1997 | Massie et al. | |
| 5,784,542 A | 7/1998 | Ohm et al. | |
| 5,855,583 A | 1/1999 | Wang et al. | |
| 6,005,199 A | 12/1999 | Harada et al. | |
| 6,197,017 B1 | 3/2001 | Brock et al. | |
| 6,331,181 B1 | 12/2001 | Tierney et al. | |
| 6,394,998 B1 | 5/2002 | Wallace et al. | |
| 6,459,926 B1 | 10/2002 | Nowlin et al. | |
| 6,494,882 B1 | 12/2002 | Lebouitz et al. | |
| 6,594,552 B1 | 7/2003 | Nowlin et al. | |
| 6,663,641 B1 | 12/2003 | Kovac et al. | |
| 6,817,974 B2 | 11/2004 | Cooper et al. | |
| 6,994,708 B2 | 2/2006 | Manzo | |
| 7,083,571 B2 | 8/2006 | Wang et al. | |
| 7,169,141 B2 | 1/2007 | Brock et al. | |
| 7,935,130 B2 | 5/2011 | Williams | |
| 8,256,306 B1 | 9/2012 | Bauer et al. | |
| 8,306,656 B1 | 11/2012 | Schaible et al. | |
| 8,444,631 B2 | 5/2013 | Yeung et al. | |
| 8,479,969 B2 | 7/2013 | Shelton, IV | |
| 8,506,555 B2 | 8/2013 | Ruiz Morales | |
| 8,551,115 B2 | 10/2013 | Steger et al. | |
| 8,597,280 B2 | 12/2013 | Cooper et al. | |
| 8,602,288 B2 | 12/2013 | Shelton, IV et al. | |
| 8,620,473 B2 | 12/2013 | Diolaiti et al. | |
| 8,628,518 B2 | 1/2014 | Blumenkranz et al. | |
| 8,771,270 B2 | 7/2014 | Burbank | |
| 8,800,838 B2 | 8/2014 | Shelton, IV | |
| 8,945,095 B2 | 2/2015 | Blumenkranz et al. | |
| 8,992,565 B2 | 3/2015 | Brisson et al. | |
| 9,028,494 B2 | 5/2015 | Shelton, IV et al. | |
| 9,192,448 B2 | 11/2015 | Blumenkranz | |
| 9,204,923 B2 | 12/2015 | Manzo et al. | |
| 9,232,979 B2 | 1/2016 | Parihar et al. | |
| 9,671,860 B2 | 6/2017 | Ogawa et al. | |
| 9,707,684 B2 | 7/2017 | Ruiz et al. | |
| 9,782,214 B2 | 10/2017 | Houser et al. | |
| 9,952,107 B2 | 4/2018 | Blumenkranz et al. | |
| 10,085,809 B2 | 10/2018 | Blumenkranz et al. | |
| 10,130,366 B2 | 11/2018 | Shelton, IV et al. | |
| 10,201,365 B2 | 2/2019 | Boudreaux et al. | |
| 10,219,874 B2 | 3/2019 | Yu et al. | |
| 10,238,458 B2 | 3/2019 | Verner et al. | |
| 10,398,433 B2 | 9/2019 | Boudreaux et al. | |
| 10,595,836 B2 | 3/2020 | Smaby et al. | |
| 10,595,887 B2 | 3/2020 | Shelton, IV et al. | |
| 10,653,435 B2 | 5/2020 | Shelton, IV et al. | |
| 10,682,141 B2 | 6/2020 | Moore et al. | |
| 12,390,291 B2 * | 8/2025 | Suresh | A61B 34/77 |
| 2003/0135203 A1 | 7/2003 | Wang et al. | |
| 2005/0096502 A1 | 5/2005 | Khalili | |
| 2005/0119527 A1 | 6/2005 | Banik et al. | |
| 2007/0043338 A1 | 2/2007 | Moll et al. | |
| 2007/0078484 A1 | 4/2007 | Talarico et al. | |
| 2007/0119274 A1 | 5/2007 | Devengenzo et al. | |
| 2007/0156019 A1 | 7/2007 | Larkin et al. | |
| 2008/0046122 A1 | 2/2008 | Manzo et al. | |
| 2008/0065105 A1 | 3/2008 | Larkin et al. | |
| 2008/0132893 A1 | 6/2008 | D'Amelio et al. | |
| 2008/0221391 A1 | 9/2008 | Weitzner et al. | |

| | | |
|---|---|---|
| 2009/0088774 A1 | 4/2009 | Swarup et al. |
| 2009/0324161 A1 | 12/2009 | Prisco |
| 2010/0041945 A1 | 2/2010 | Isbell, Jr. |
| 2010/0063478 A1 | 3/2010 | Selkee |
| 2010/0219388 A1 | 9/2010 | Schena |
| 2010/0313679 A1 | 12/2010 | Larkin et al. |
| 2011/0071543 A1 | 3/2011 | Prisco et al. |
| 2011/0277775 A1 | 11/2011 | Holop et al. |
| 2011/0282356 A1 | 11/2011 | Solomon et al. |
| 2011/0295269 A1 | 12/2011 | Swensgard et al. |
| 2011/0295270 A1 | 12/2011 | Giordano et al. |
| 2012/0123441 A1 | 5/2012 | Au et al. |
| 2013/0291654 A1 | 11/2013 | Blumenkranz et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0238174 A1 | 8/2014 | Ikebe |
| 2014/0257333 A1 | 9/2014 | Blumenkranz |
| 2014/0330432 A1 | 11/2014 | Simaan et al. |
| 2015/0051034 A1 | 2/2015 | Cooper et al. |
| 2015/0150635 A1 | 6/2015 | Kilroy et al. |
| 2015/0374447 A1 | 12/2015 | Blumenkranz et al. |
| 2016/0030240 A1 | 2/2016 | Gonenc et al. |
| 2017/0007345 A1 | 1/2017 | Smith et al. |
| 2017/0165017 A1 | 6/2017 | Chaplin et al. |
| 2017/0172509 A1 | 6/2017 | Hein et al. |
| 2017/0172687 A1 | 6/2017 | Smith et al. |
| 2017/0215855 A1 | 8/2017 | Nunan |
| 2017/0215944 A1 | 8/2017 | Keffeler |
| 2018/0042689 A1 | 2/2018 | Mozdzierz et al. |
| 2018/0068773 A1 | 3/2018 | Zhu et al. |
| 2018/0078249 A1 | 3/2018 | Stoy et al. |
| 2018/0206904 A1 | 7/2018 | Felder et al. |
| 2019/0069966 A1 | 3/2019 | Petersen et al. |
| 2019/0069967 A1 | 3/2019 | Crews et al. |
| 2019/0094084 A1 | 3/2019 | Swinehart et al. |
| 2019/0125354 A1 | 5/2019 | Deck et al. |
| 2019/0175188 A1 | 6/2019 | PV R |
| 2019/0175887 A1 | 6/2019 | Shameli |
| 2019/0201018 A1 | 7/2019 | Shelton, IV et al. |
| 2019/0223960 A1 | 7/2019 | Chaplin et al. |
| 2019/0223966 A1 | 7/2019 | Holop et al. |
| 2019/0239965 A1 | 8/2019 | Abbott |
| 2019/0249759 A1 | 8/2019 | Abbott |
| 2019/0336228 A1 | 11/2019 | Blumenkranz et al. |
| 2019/0388156 A1 | 12/2019 | Shameli |
| 2020/0015876 A1 | 1/2020 | Chou et al. |
| 2020/0173525 A1 | 6/2020 | Cooper et al. |
| 2020/0208711 A1 | 7/2020 | Pu et al. |
| 2020/0278265 A1 | 9/2020 | Suresh |
| 2020/0405375 A1 | 12/2020 | Shelton, IV et al. |
| 2021/0033478 A1 | 2/2021 | Shang |
| 2021/0045819 A1 | 2/2021 | Castillo et al. |
| 2021/0045825 A1 | 2/2021 | Lee et al. |
| 2021/0353352 A1 | 11/2021 | Petersen |
| 2021/0401524 A1 | 12/2021 | Suresh et al. |
| 2022/0003615 A1 | 1/2022 | Kadokura |
| 2022/0386859 A1 | 12/2022 | Holsten |
| 2023/0003596 A1 | 1/2023 | Petersen |
| 2024/0090959 A1 | 3/2024 | Deyanov |
| 2024/0148405 A1 | 5/2024 | Moreira et al. |
| 2025/0082360 A1 | 3/2025 | Moreira Ridsdale et al. |
| 2025/0164332 A1 | 5/2025 | Petersen |
| 2025/0262018 A1 | 8/2025 | Suresh et al. |

FOREIGN PATENT DOCUMENTS

| | | | |
|---|---|---|---|
| CN | 105682597 A | 6/2016 | |
| CN | 109630582 A | 4/2019 | |
| CN | 111655187 A | 9/2020 | |
| CN | 114681025 A | 7/2022 | |
| DE | 1147411 B | 4/1963 | |
| EP | 0590713 A2 | 4/1994 | |
| EP | 2362285 A2 | 8/2011 | |
| EP | 2431000 A2 | 3/2012 | |
| JP | 2000172355 A | 6/2000 | |
| KR | 100778387 B1 | 11/2007 | |
| WO | WO2004052171 A2 | 6/2004 | |
| WO | WO-2007143859 A1 | 12/2007 | |

(56)          References Cited

FOREIGN PATENT DOCUMENTS

| WO | WO-2009123891 A1 | 10/2009 |
|----|------------------|---------|
| WO | WO-2012166806 A1 | 12/2012 |
| WO | WO2014/070980 A1 | 5/2014 |
| WO | WO-2014151952 A1 | 9/2014 |
| WO | WO-2015069887 A1 | 5/2015 |
| WO | WO-2017064303 A1 | 4/2017 |
| WO | WO2017/210333 A1 | 12/2017 |
| WO | WO-2018075527 A1 | 4/2018 |
| WO | WO-2019099562 A1 | 5/2019 |
| WO | WO2019/118337 | 6/2019 |
| WO | WO-2020102774 A1 | 5/2020 |
| WO | WO-2020102776 A1 | 5/2020 |
| WO | WO-2020102778 A1 | 5/2020 |
| WO | WO-2020102780 A1 | 5/2020 |
| WO | WO-2021055276 A1 | 3/2021 |
| WO | WO-2021076765 A1 | 4/2021 |
| WO | WO-2021097386 A1 | 5/2021 |
| WO | WO-2021219396 A1 | 11/2021 |
| WO | WO-2022056213 A1 | 3/2022 |
| WO | WO-2022132885 A1 | 6/2022 |
| WO | WO-2025096793 A1 | 5/2025 |

OTHER PUBLICATIONS

Office Action for U.S. Appl. No. 17/642,892, mailed Mar. 27, 2024, 14 Pages.

Hazel D., "Comparing Strain Gage Measurements to Force Calculations in a Simple Cantilever Beam," Worcester Polytechnic Institute Major Qualifying Project, Jan. 27, 2016, 39 pages.

International Search Report and Written Opinion for Application No. PCT/US2020/050696. mailed Feb. 18, 2021, 14 pages.

International Search Report and Written Opinion for Application No. PCT/US2021/049792. mailed Jan. 25, 2022, 10 pages.

Invitation to Pay Additional Fees and International Search Authority for PCT/US202020/050696, mailed Nov. 24, 2020, 10 pages Mertmann M., et al., "Grippers for the Micro Assembly Containing Shape Memory Actuators and Sensors," Le Journal de Physique IV France, vol. 7, Institut fuer Werstoffe, Ruhr-Universitaet, Bochum, Germany, Nov. 1997, pp. C5-621-C5-626.

Vertut, J. and Coiffet, P., "Robot Technology: Teleoperation and Robotics Evolution and Development," English translation, Prentice-Hall, Inc., Inglewood Cliffs, NJ, USA 1986, vol. 3A, 332 pages.

Office Action for EP Application No. 20785869.7, mailed Dec. 18, 2024, 7 Pages.

* cited by examiner

1000

1150

1020

1210

1200

1400

1010

1300

P

1100

S

1150

5827

5829

DEVICES AND METHODS FOR COMPACT, REDUNDANT INDUCTIVE FORCE SENSOR

CROSS-REFERENCE TO RELATED APPLICATIONS

This patent application is a U.S. national stage filing under 35 U.S.C. § 371 of International Application No. PCT/US2021/049792, entitled "Devices and Methods for Compact. Redundant Inductive Force Sensor" (filed Sep. 10, 2021), which claims priority to and the filing date benefit of U.S. Provisional Patent Application No. 63/077,833, entitled "Devices and Method for Compact, Redundant Inductive Force Sensor" (filed Sep. 14, 2020), the disclosure of each of which is incorporated herein by reference in its entirety.

This patent application is related to PCT International Patent Application No. PCT/US2020/050696, entitled "COMPACT, DIFFERENTIAL, COAXIAL INDUCTIVE FORCE SENSOR" (filed Sep. 14, 2020), and U.S. Provisional Patent Application No. 62/901,729, entitled "COMPACT, DIFFERENTIAL, COAXIAL INDUCTIVE FORCE SENSOR" (filed Sep. 17, 2019), each of the disclosures of which is incorporated herein by reference in its entirety.

BACKGROUND

The embodiments described herein relate to force sensing mechanical structures, more specifically to medical devices, and still more specifically to instruments used for minimally invasive surgery. More particularly, the embodiments described herein relate to medical devices that include a force sensor unit that is coupled to a mechanical structure of the medical device and is used to measure axial forces applied to the end effector of the medical device during a surgical procedure.

Known techniques for minimally invasive medical interventions employ instruments to manipulate tissue that can be either manually controlled or controlled via hand-held or mechanically grounded teleoperated medical systems that operate with at least partial computer-assistance ("telesurgical systems"). Many known medical instruments include a therapeutic or diagnostic end effector (e.g., forceps, a cutting tool, or a cauterizing tool) mounted on an optional wrist mechanism at the distal end of a shaft. During a medical procedure, the end effector, wrist mechanism, and the distal end of the shaft are inserted into a small incision or a natural orifice of a patient to position the end effector at a work site within the patient's body. The optional wrist mechanism can be used to change the end effector's position and orientation with reference to the shaft to perform a desired procedure at the work site. In known instruments, motion of the instrument as a whole provides mechanical degrees of freedom (DOFs) for movement of the end effector and the wrist mechanisms generally provide the desired DOFs for movement of the end effector with reference to the shaft of the instrument. For example, for forceps or other grasping tools, known wrist mechanisms are able to change the pitch and yaw of the end effector with reference to the shaft. A wrist may optionally provide a roll DOF for the end effector, or the roll DOF may be implemented by rolling the shaft. An end effector may optionally have additional mechanical DOFs, such as grip or knife blade motion. In some instances, wrist and end effector mechanical DOFs may be combined. For example, U.S. Pat. No. 5,792,135 (filed May 16, 1997) discloses a mechanism in which wrist and end effector grip DOFs are combined.

To enable the desired movement of the wrist mechanism and end effector, known instruments include mechanical connectors (e.g., cables) that extend through the shaft of the instrument and that connect the distal wrist mechanism to a proximal mechanical structure used to move the connectors to operate the wrist mechanism. For telesurgical systems, the mechanical structure is typically motor driven and operably coupled to a processing system to provide a user interface for a clinical user (e.g., a surgeon) to control the instrument as a whole and the instrument's components and functions.

Force sensing surgical instruments are known and together with associated telesurgical systems produce associated haptic feedback to a clinical user during a medical procedure, which brings better immersion, realism, and intuitiveness to a clinician performing the procedure. For effective haptics rendering and accuracy, force sensors are placed on a medical instrument. One approach is to include a force sensor unit attached to and/or incorporated within the proximal mechanical structure of the medical instrument and that can be used to measure axial forces imparted on the end effector of the medical instrument. These force measurements are measured at or near the instrument shaft and are used to produce haptic feedback forces at an input to a master control device to provide to a user an indication of the forces imparted by the medical instrument to, for example, patient tissue. That is, a force imparted by an instrument on objects such as tissue or suture are indicated by a corresponding reactive force from such objects on the instrument, and the sensed reactive force is conveyed to the user as a haptic sensation.

Enhancements to force sensor systems lead to more accurate force measurements, which in turn result in more accurate haptic feedback. For example, including multiple sensors to measure a single force parameter (e.g., the axial force imparted on the end effector) can improve measurement accuracy (e.g., by producing an average measurement or by allowing for subtraction of commons modes) and allow for operation if one sensor fails. The inclusion of additional sensors, however, competes for the limited space that exists because of the mechanical structure and overall instrument size restrictions required by minimally invasive medical instruments. Force sensor systems must not only be as effective as possible, they must fit within the spatial design constrains of objects experiencing the force, such as medical instruments.

Thus, a need exists for improved force-sensing capabilities that can in turn improve haptic feedback, especially within the spatial constraints of minimally invasive surgical instruments.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

In some embodiments, an apparatus includes a mechanical structure and a force sensor unit coupled to the mechanical structure. The force sensor unit comprises a mounting bracket, a first rod, a second rod, a first magnet, a second magnet, a first coil coupled to the mounting bracket, and a second coil coupled to the mounting bracket. The first rod comprises a distal portion and a proximal portion, and a center axis of the first rod is defined between the proximal and distal portions of the first rod. The second rod comprises a distal portion and a proximal portion, and a center axis of the second rod is defined between the proximal and distal portions of the second rod. The center axis of the second rod is noncoaxial with the center axis of the first rod. The first magnet is coupled to the first rod, and the second magnet is coupled to the second rod. The first magnet translates within the first coil along the center axis of the first rod, and the second magnet translates within the second coil along the center axis of the second rod.

In some embodiments, the apparatus further comprises a shaft coupled to the mechanical structure. The shaft is operably coupled to the first rod and the second rod such that translational movement of the shaft relative to the mechanical structure moves the first rod within the first coil and moves the second rod within the second coil. In some embodiments, the shaft comprises a proximal end and a distal end, and a center axis of the shaft is defined between the proximal and distal ends of the shaft. The shaft is operably coupled to the first rod and the second rod such that the shaft is rotatable about the center axis of the shaft without moving the first rod or the second rod.

In some embodiments, the apparatus further comprises a link coupled to the shaft, with the first rod and the second rod being coupled to the link. The link comprises a roll drive receiver in which the shaft is rotatable relative to the link without moving the first rod or the second rod. In some embodiments, the shaft comprises a proximal end and a distal end, and a center axis is defined between the proximal and distal ends of the shaft. A first signal is generated by the first coil and is associated with a position of the first magnet within the first coil, and a second signal is generated by the second coil and is associated with a position of the second magnet within the second coil. The first signal from the first coil and the second signal from the second coil are associated with a linear displacement of the shaft along the center axis of the shaft. In some embodiments, the linear displacement is in proportion to a force imparted to the shaft in a direction along the center axis of the shaft.

In some embodiments, the shaft comprises a proximal end and a distal end, and a center axis of the shaft is defined between the proximal and distal ends of the shaft. The first coil and the second coil are each secured to the mounting bracket such that the center axis of the shaft is centered between the center axis of the first rod and the center axis of the second rod. In some embodiments, the center axis of the first rod and the center axis of the second rod are parallel to the center axis of the shaft. In some embodiments, the first coil has a first height, the second coil has a second height, and the first height is equal to the second height.

In some embodiments, the shaft comprises a proximal end and a distal end, and a center axis is defined between the proximal and distal ends of the shaft. The apparatus further comprises a linkage coupled to the shaft and to the mechanical structure. The linkage comprises a spring configured to be displaced in proportion to a force imparted to the shaft in a direction along the center axis of the shaft.

In some embodiments, a first signal generated by the first coil is associated with a position of the first magnet within the first coil, and a second signal generated by the second coil is associated with a position of the second magnet within the second coil. The force sensor unit comprises a microprocessor configured to receive the first and second signals. In some embodiments, the shaft comprises a proximal end and a distal end, and a center axis is defined between the proximal and distal ends of the shaft. In such embodiments, the first signal has a first frequency, the second signal has a second frequency, and the microprocessor is configured to execute instructions to determine from the first frequency and the second frequency a measure of a force on the shaft along the center axis of the shaft.

In some embodiments, a medical device comprises an instrument shaft and a medical end effector coupled to the distal end of the shaft. A mechanical structure is coupled to the proximal end of the shaft, and a force sensor unit is coupled to the mechanical structure and to the instrument shaft. The force sensor unit comprises a first coil wound about a first coil axis, a second coil wound about a second coil axis, a first rod, and a second rod. An instrument shaft axis is defined between the proximal and distal ends of the instrument shaft, and the instrument shaft axis extends between the first coil axis and the second coil axis. The first rod is operably coupled to the instrument shaft and comprises a first magnet positioned to move within the first coil along the first coil axis as the instrument shaft moves along the instrument shaft axis, and the second rod is operably coupled to the instrument shaft and comprises a second magnet positioned to move within the second coil along the second coil axis as the instrument shaft moves along the instrument shaft axis.

In some embodiments, the medical device further comprises a linkage coupled to the shaft and to the mechanical structure. The linkage comprises a spring configured to be displaced in proportion to a force imparted to the shaft in a direction along the center axis of the shaft.

In some embodiments, a first signal generated by the first coil is associated with a position of the first magnet within the first coil, and a second signal generated by the second coil is associated with a position of the second magnet within the second coil. The force sensor unit comprises a microprocessor configured to receive the first and second signals. In some embodiments, the first signal has a first frequency, the second signal has a second frequency, and the microprocessor is configured to execute instructions to determine a measurement of a force on the shaft along the center axis of the shaft from the first frequency and the second frequency. In some embodiments, the first signal from the first coil and the second signal from the second coil are associated with a linear displacement of the shaft along the center axis of the shaft.

In some embodiments, the medical device further comprises a linkage coupled to the shaft and to the mechanical structure and the linkage comprises a spring. The spring is configured to be displaced in proportion to a force imparted to the shaft in a direction along the center axis of the shaft. In some embodiments, the first center axis of the first rod and the second center axis of the second rod are parallel to the center axis of the shaft.

In some embodiments, a medical device comprise an instrument support structure, an instrument shaft, and a force sensor unit. The instrument shaft comprises a proximal end and a distal end, and an instrument shaft axis is defined between the proximal and distal ends of the instrument shaft. The force sensor unit comprises a linkage coupled between the instrument support structure and the proximal end of the instrument shaft, a first coil wound about a first coil axis, a second coil wound about a second coil axis different from the first coil axis, a first magnet at least partially within the first coil, and a second magnet at least partially within the second coil. The first coil, the second coil, the first magnet, and the second magnet are positioned between the instrument support structure and the linkage of the force sensor unit such that translation of the instrument shaft along the instrument shaft axis with reference to the instrument support structure causes relative movement between the first magnet and the first coil along the first coil axis and relative movement between the second magnet and the second coil along the second coil axis.

In some embodiments, the first coil and the second coil are fixed with reference to the instrument support structure. In some embodiments, the linkage comprises a rotational joint having an axis of rotation coaxial with the instrument shaft axis, and the instrument shaft is coupled to the linkage of the force sensor unit to rotate at the joint about the axis of rotation with reference to the instrument support structure.

In some embodiments, the medical device comprises a proximal mechanical structure, a distal end mechanism, and a connector. The distal end mechanism is coupled to the distal end of the instrument shaft and comprises a movable component. The proximal mechanical structure comprises the instrument support structure and an actuator input piece mounted to move with reference to the instrument support structure. The connector is coupled between the actuator input piece and the movable component of the distal end mechanism.

6

Figures 7A, 7B:
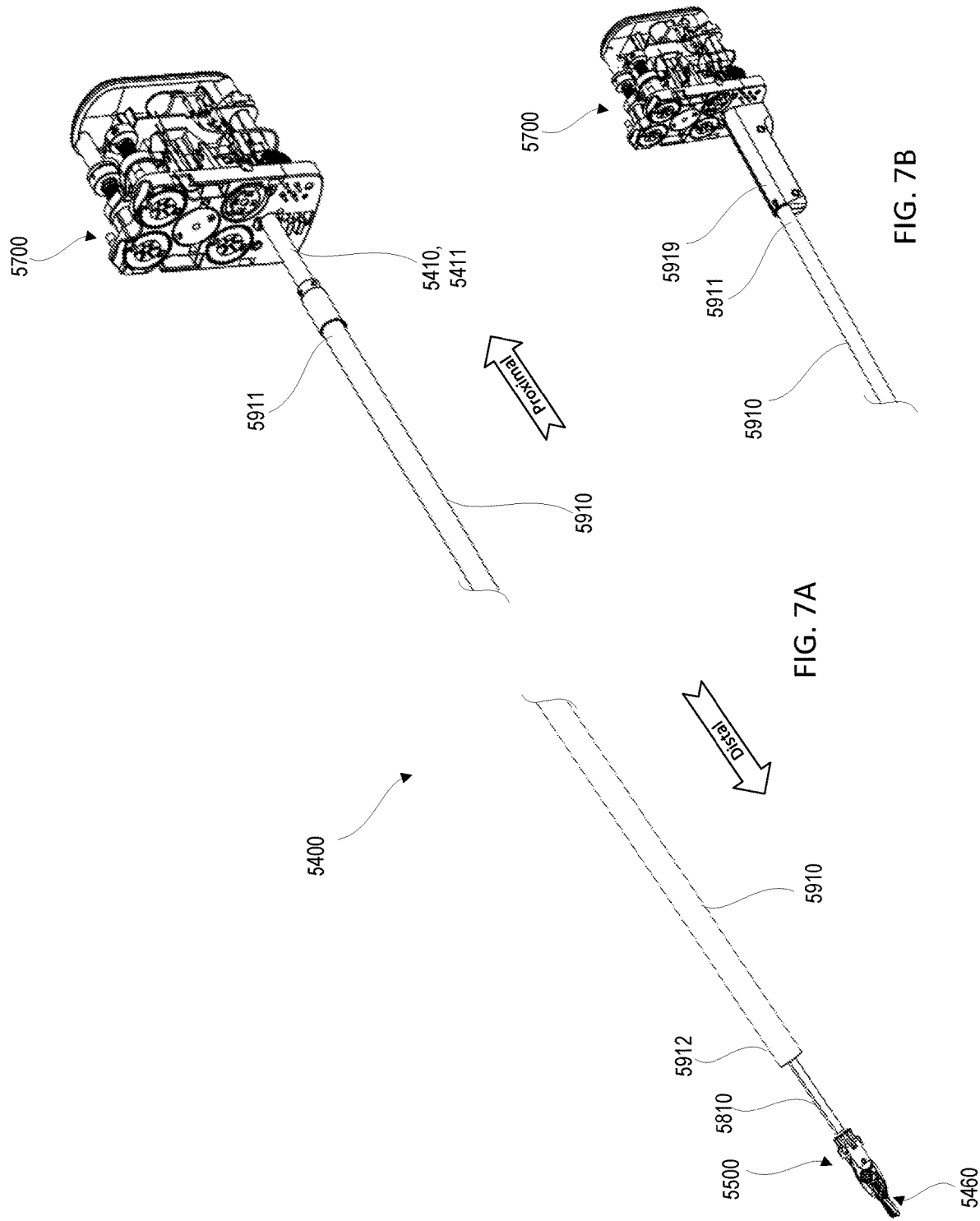
FIG. 7A is a perspective view of a medical device, according to an embodiment.
FIG. 7B is a perspective view of a proximal portion of the medical device of FIG. 7A including a locking handle coupled to the outer shaft.
Figure 15:
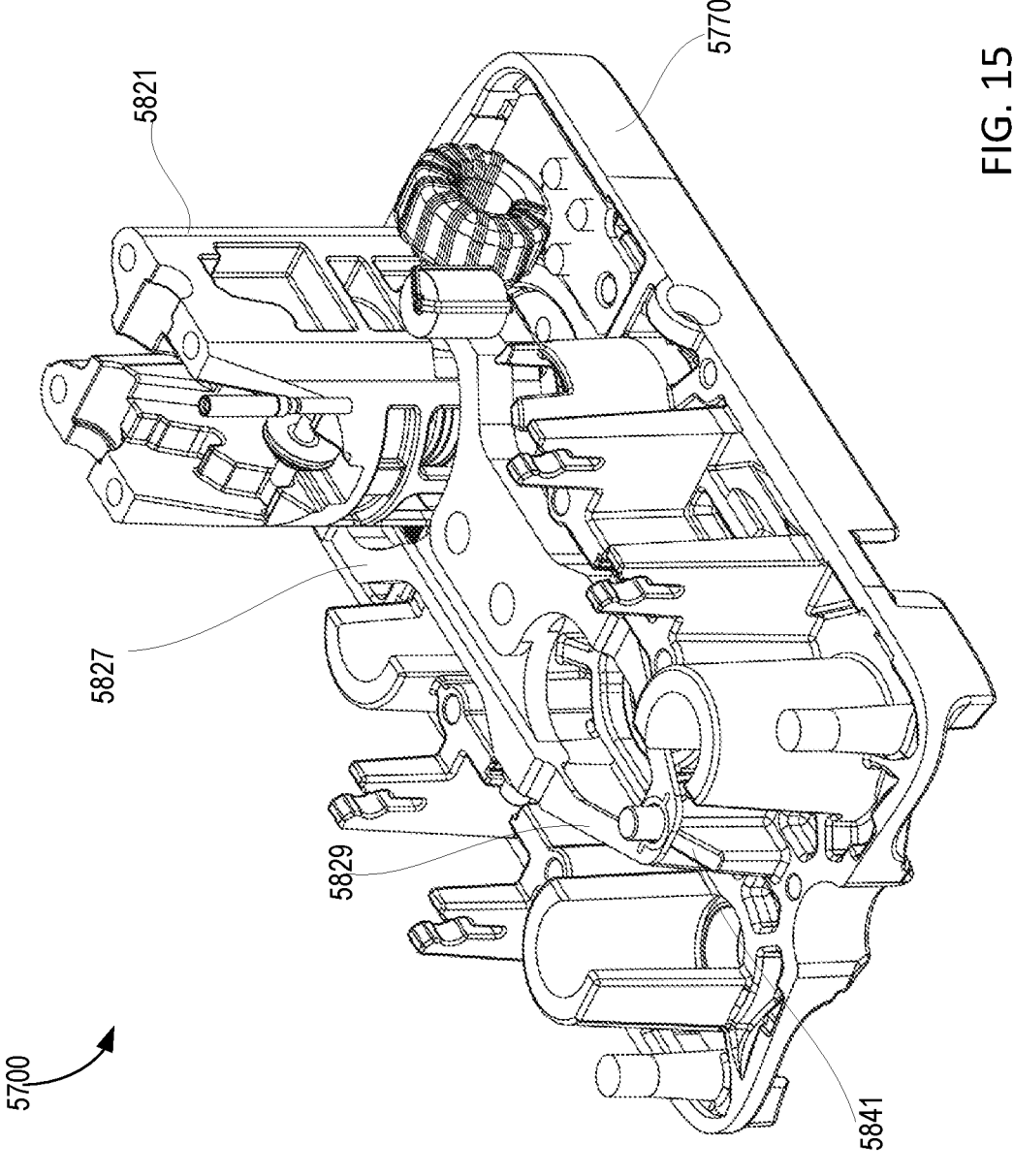
Figure 16:
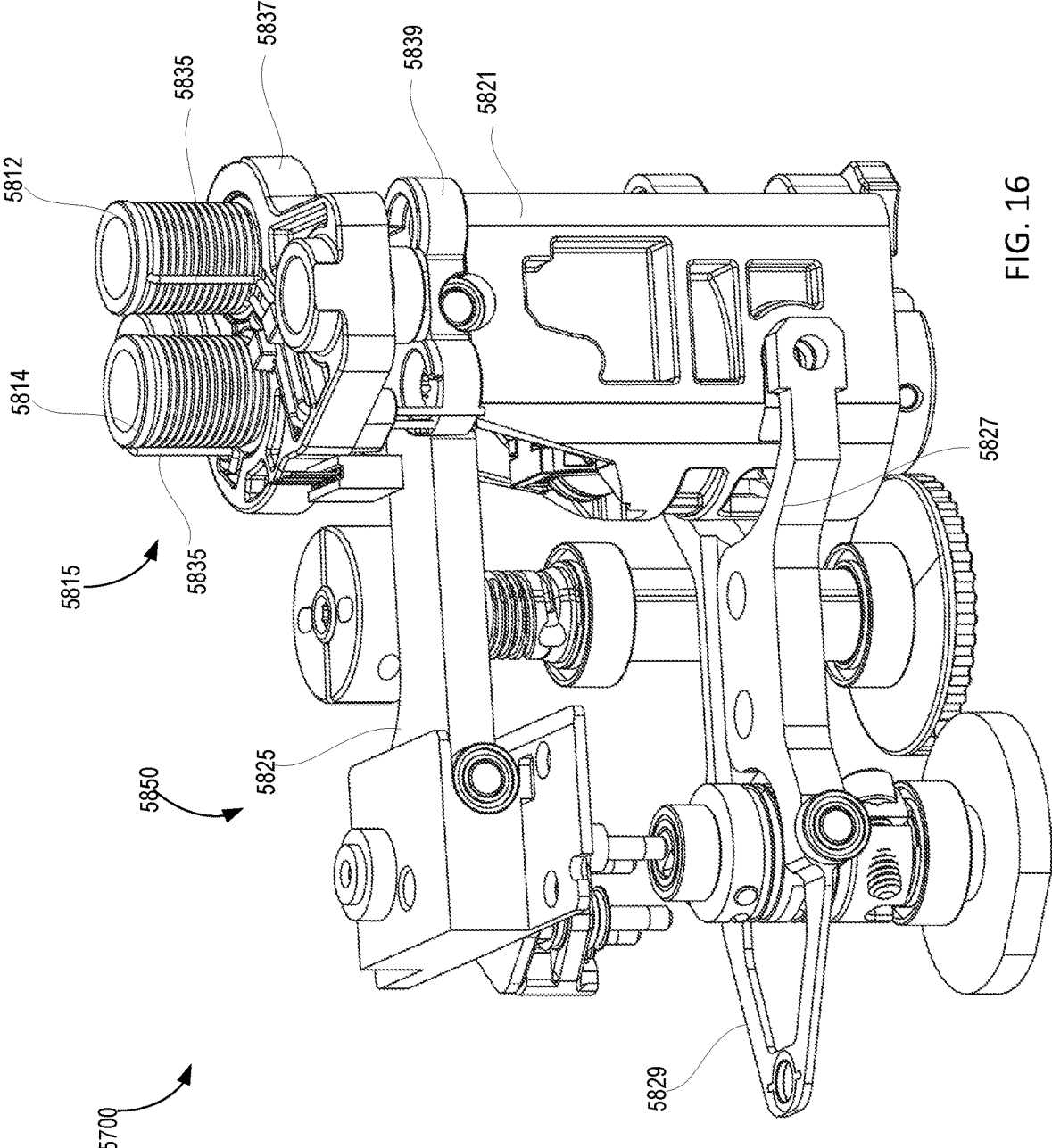

FIGS. 15 and 16 are each different perspective views of the mechanical structure of the medical device of FIG. 7A with select components removed for illustration purposes.

Figure 17:
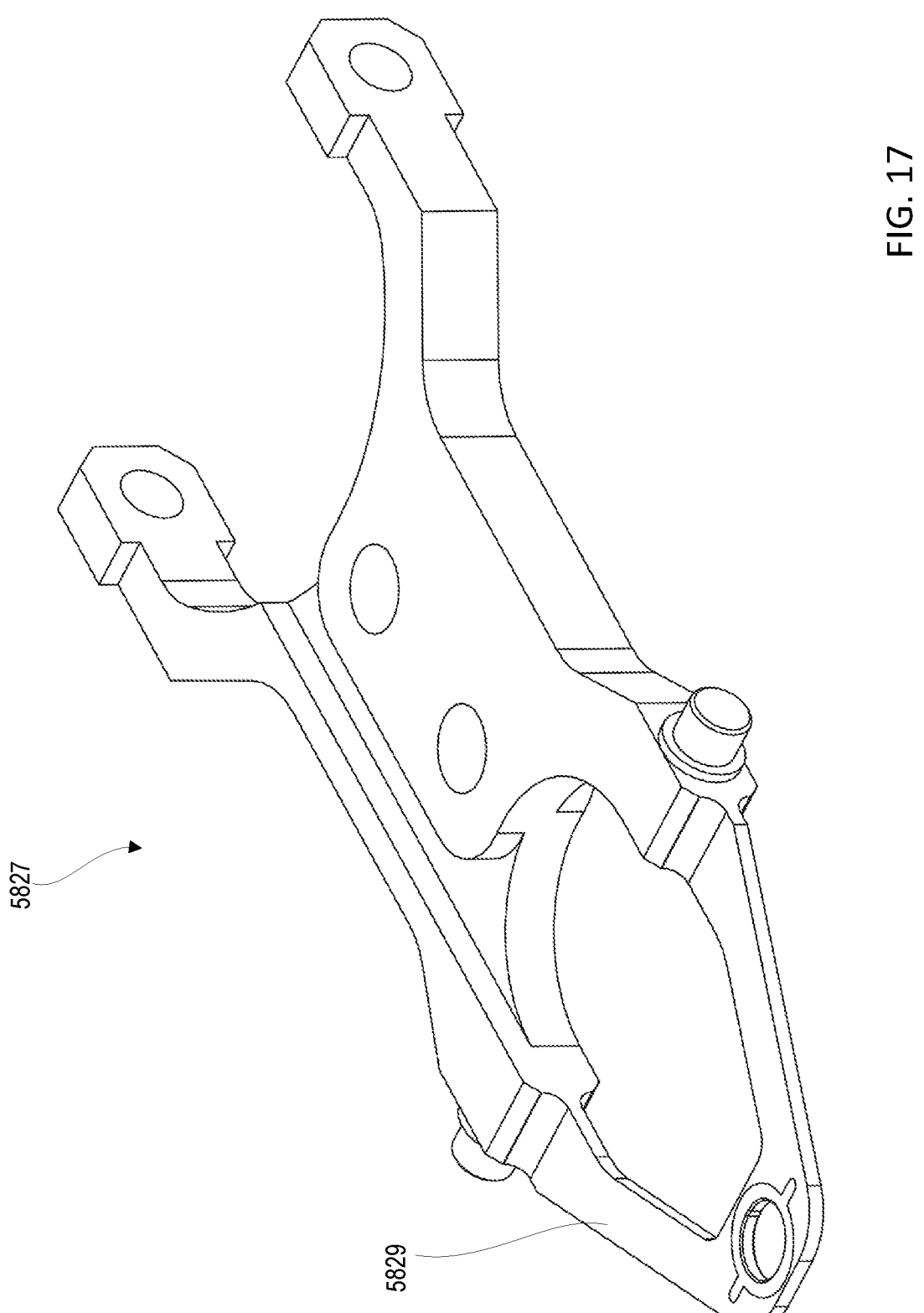

FIG. 17 is a perspective view of a link of a force sensor unit of the medical device of FIG. 7A.

Figure 18:
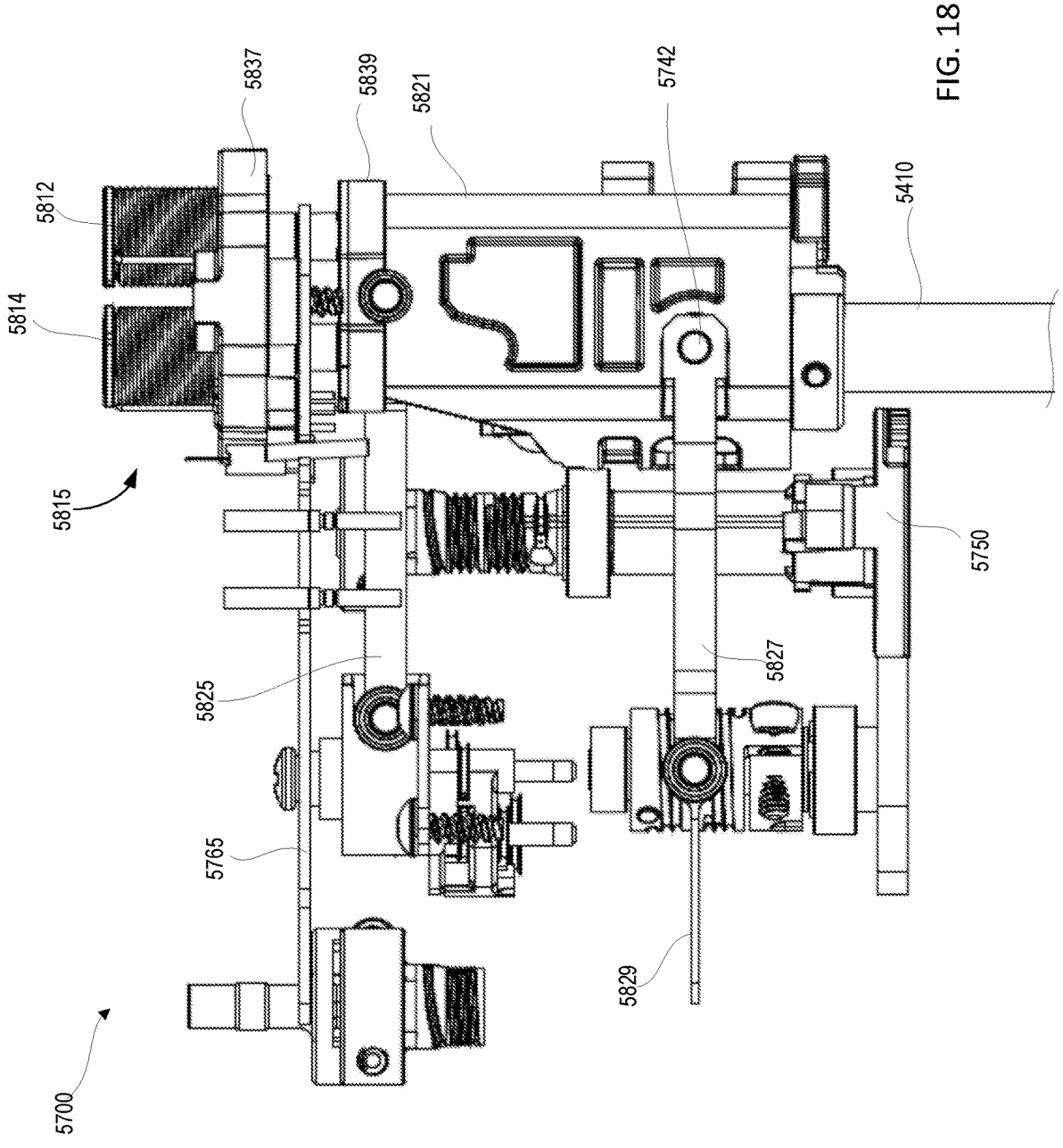

FIG. 18 is a side view of the mechanical structure of the medical device of FIG. 7A with select components removed for illustration purposes and showing the spring and shaft in a first neutral position.

Figures 19, 20:
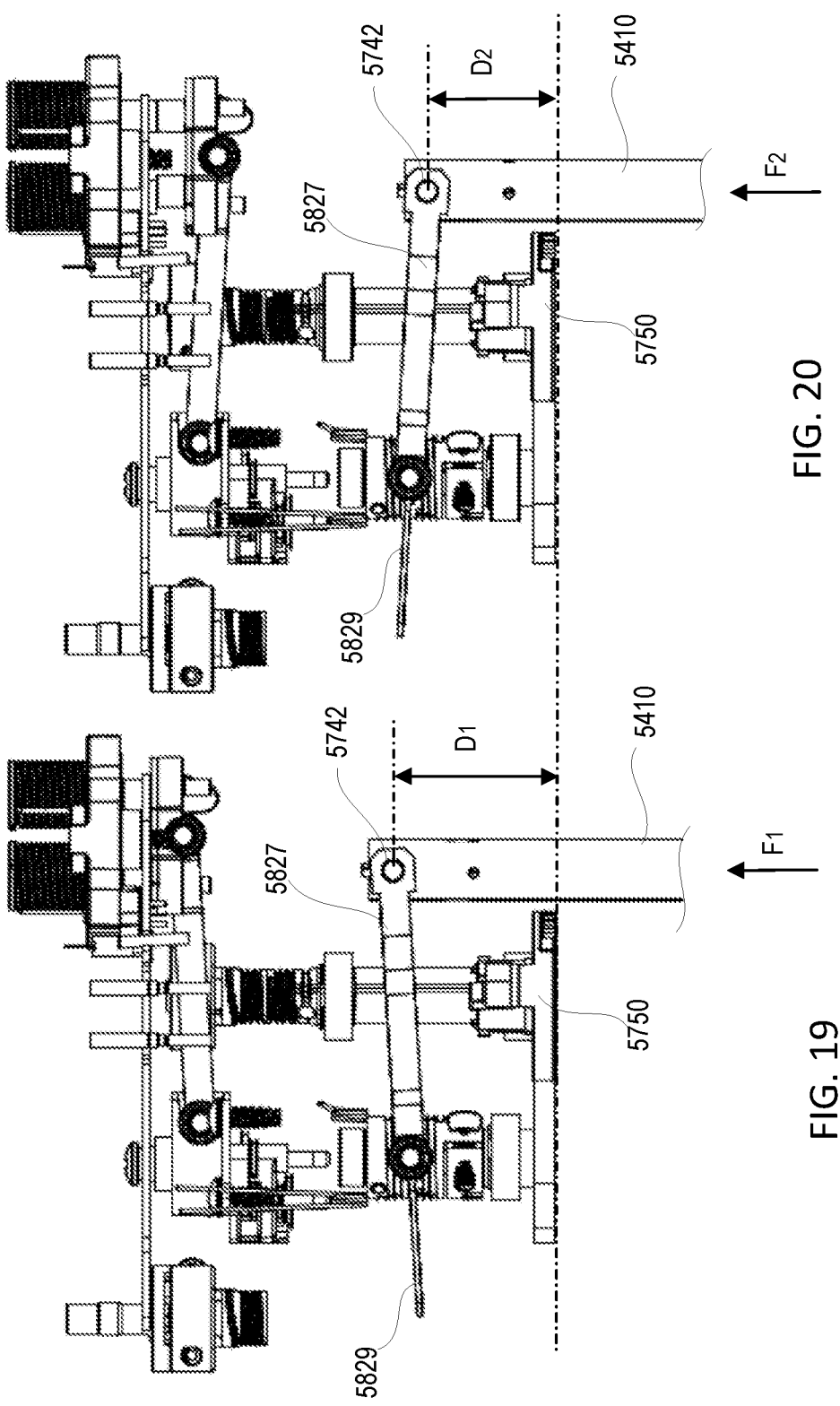

FIGS. 19 and 20 are each a side view of the mechanical structure of the medical device of FIG. 7A with select components removed for illustration purposes and showing the shaft in a second upper position (FIG. 19) and a third lower position (FIG. 20).

Figure 21:
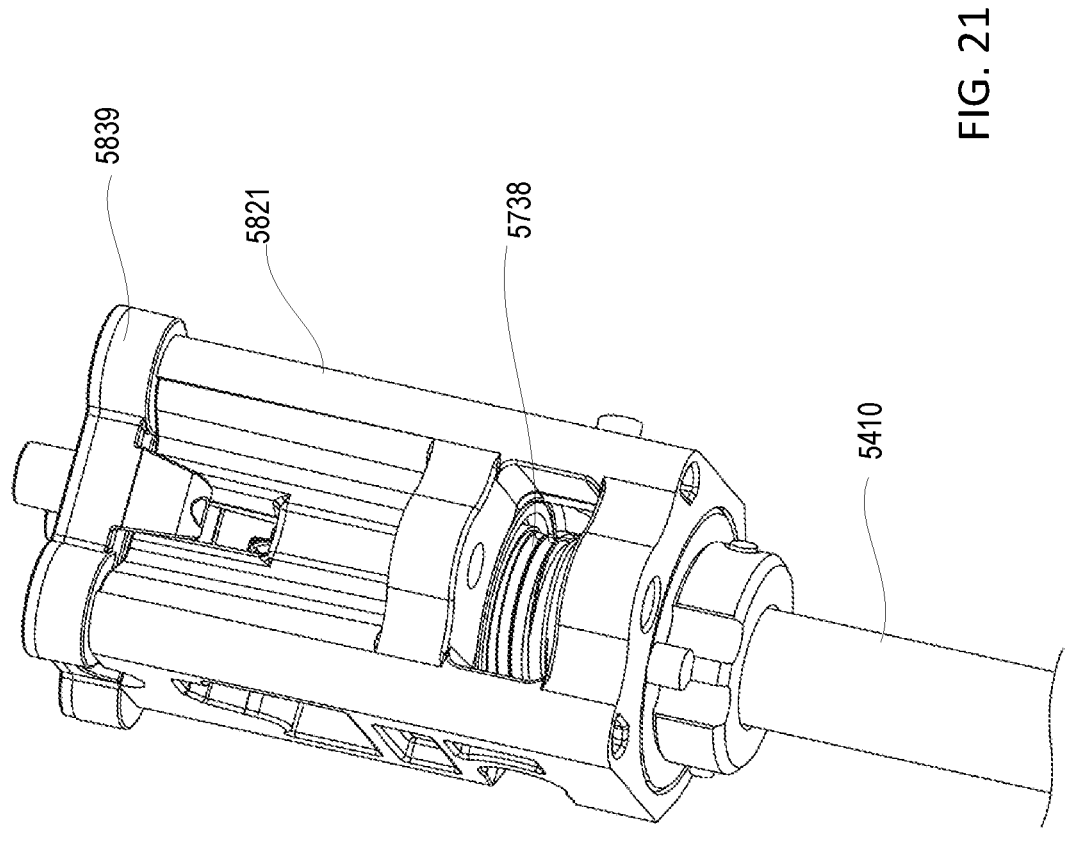

FIG. 21 is a perspective view of the shaft coupled to the roll drive receiver and roll carrier of the medical device of FIG. 7A.

Figure 22:
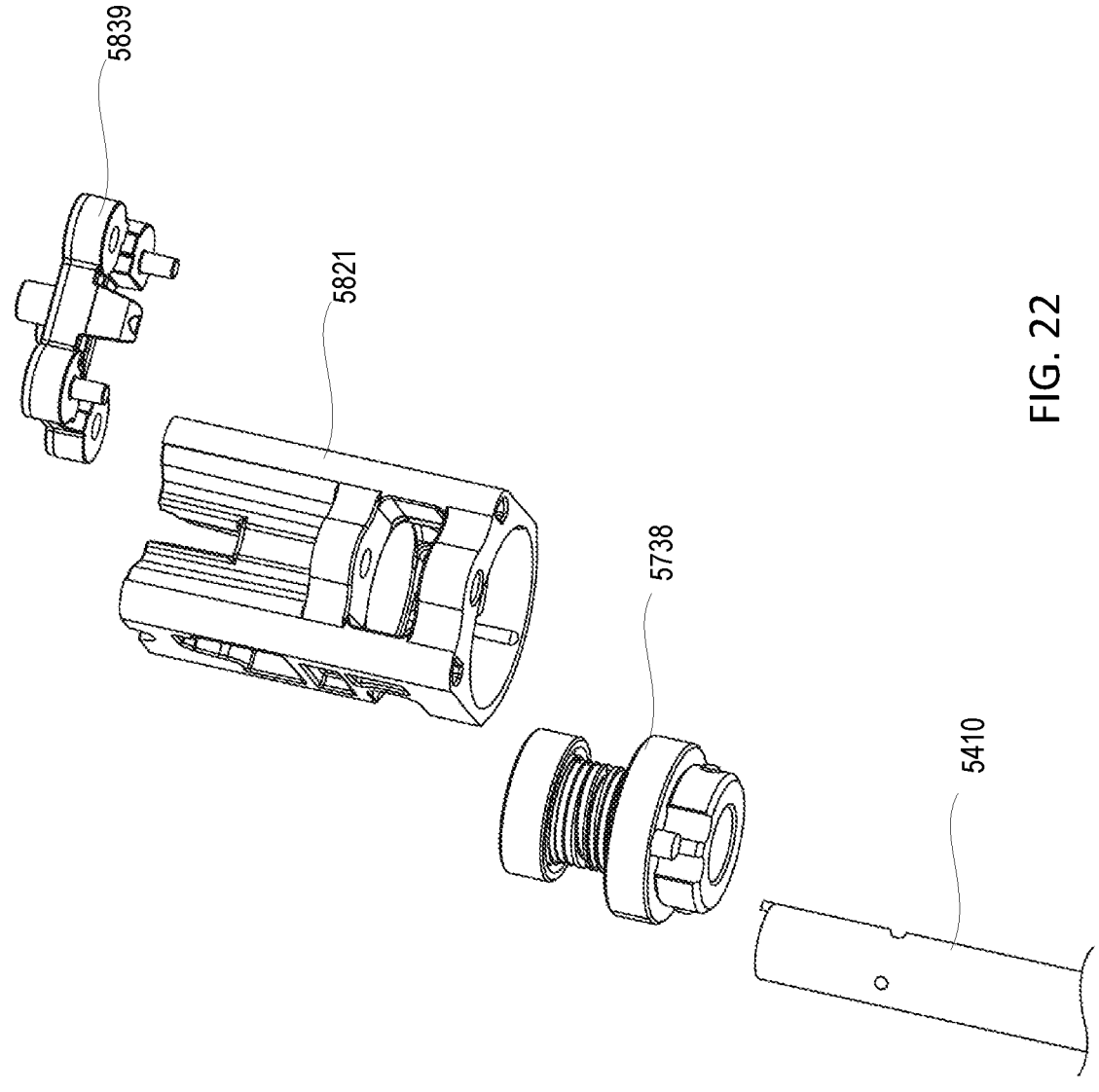

FIG. 22 is an exploded perspective view of the shaft coupled to the roll drive receiver and roll carrier of the medical device of FIG. 21.

Figure 23:
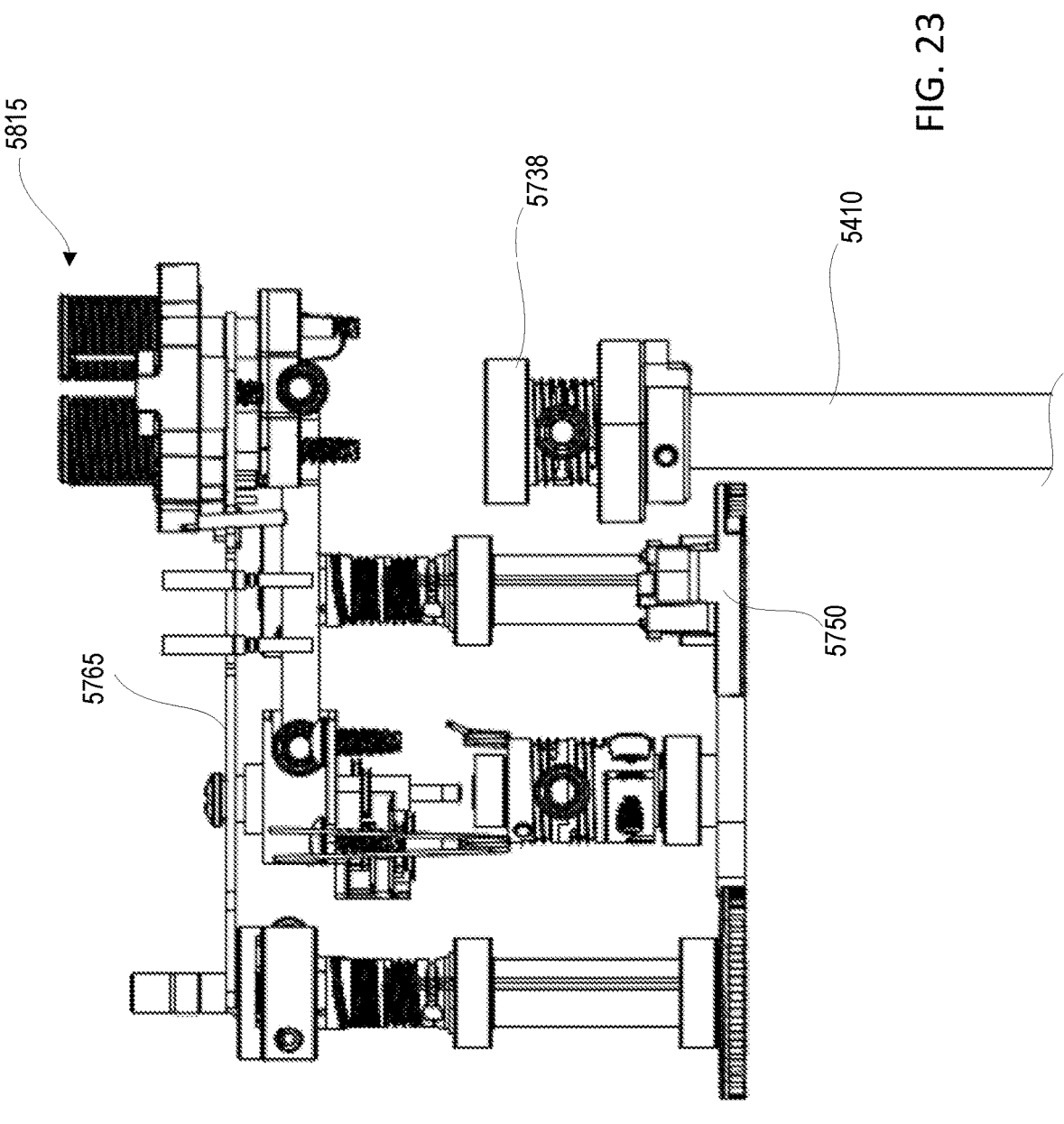

FIG. 23 is a side view of the mechanical structure of the medical device of FIG. 7A with select components removed for illustration purposes and showing the shaft coupled to the roll drive receiver.

Figure 24:
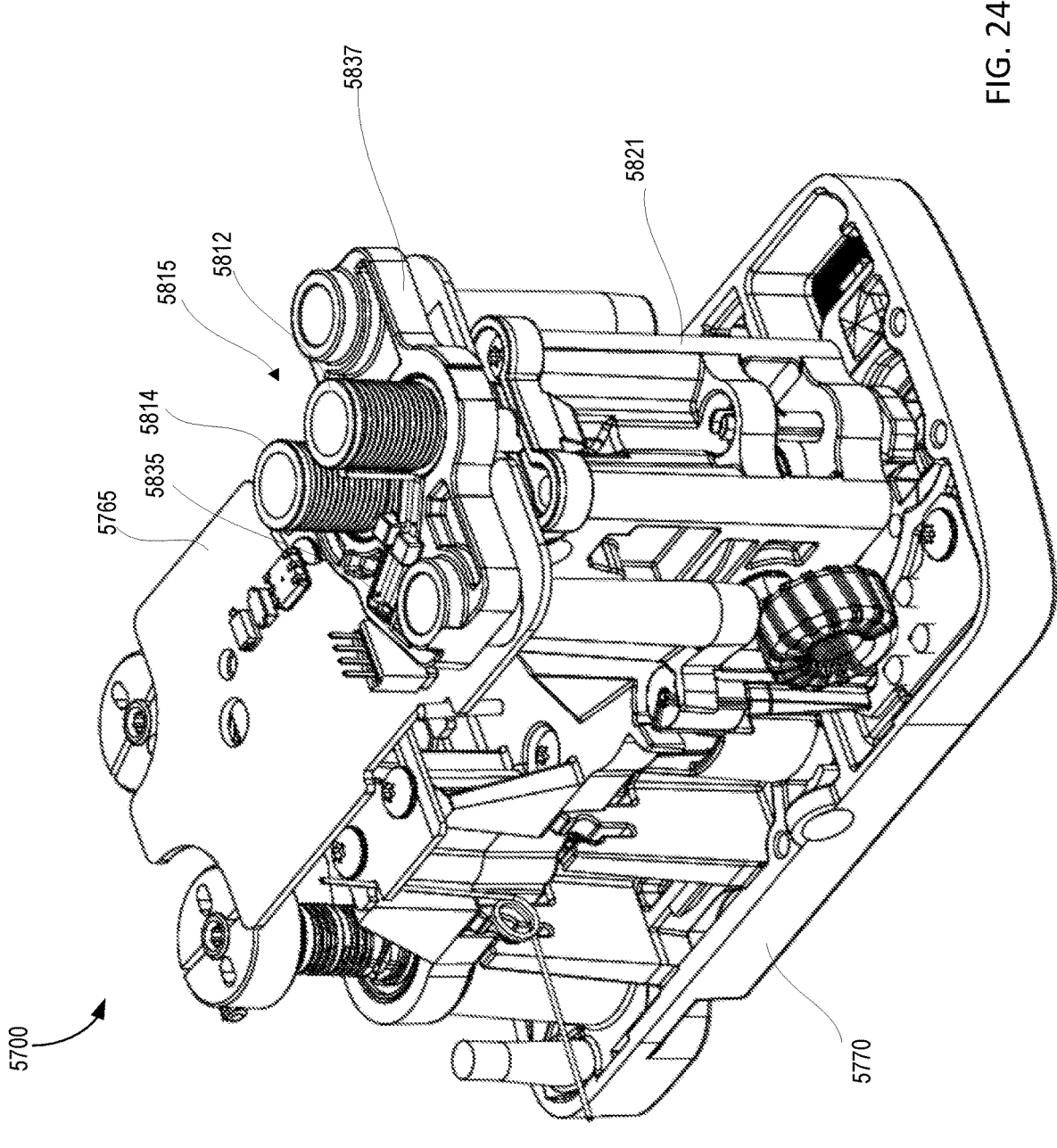

FIG. 24 is an end perspective view of the mechanical structure of the medical device of FIG. 7A with select components removed for illustration purposes.

Figure 25:
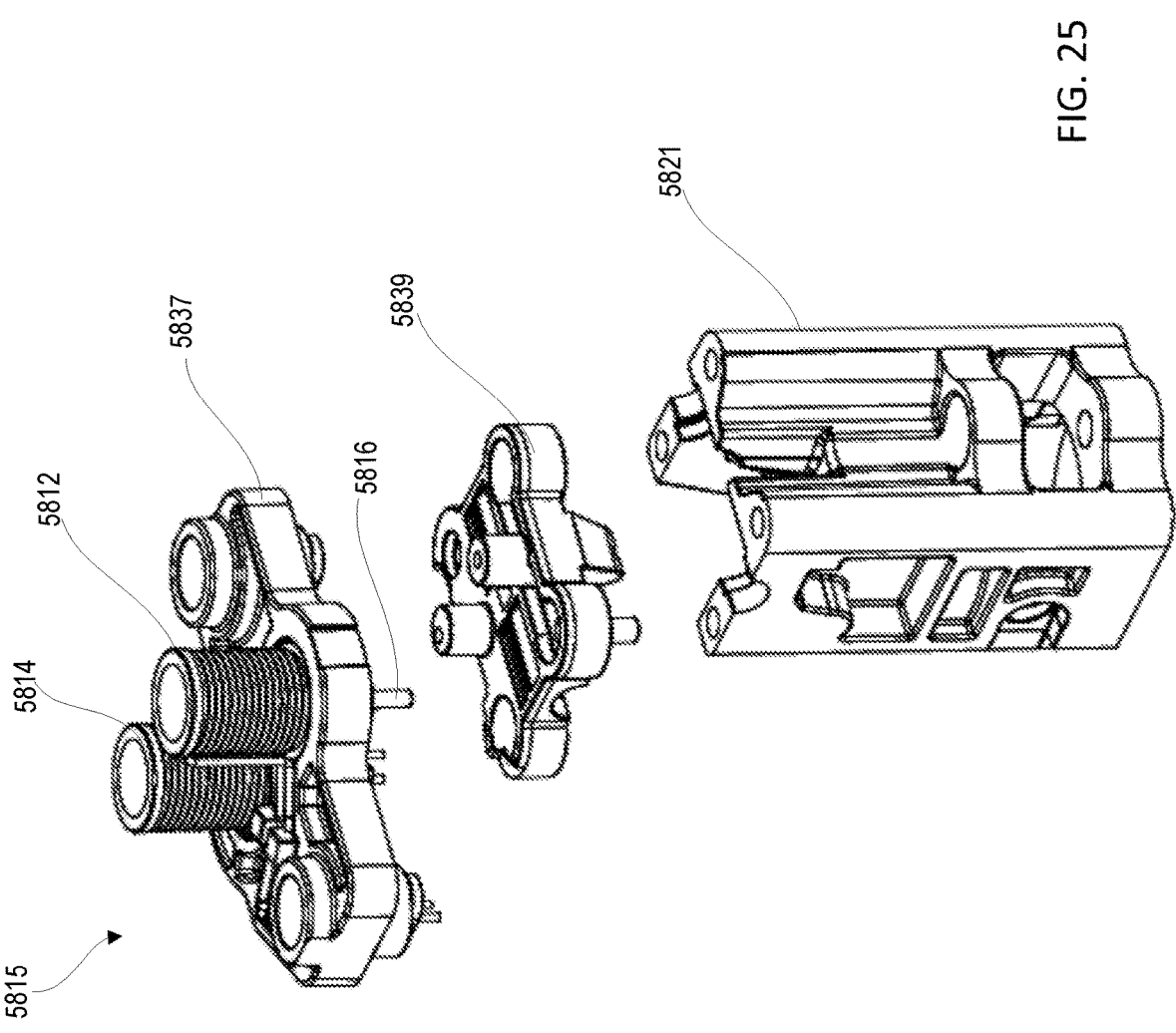

FIG. 25 is an exploded view of the coil assembly and a link of the force sensor unit of the medical device of FIG. 7A.

Figure 26:
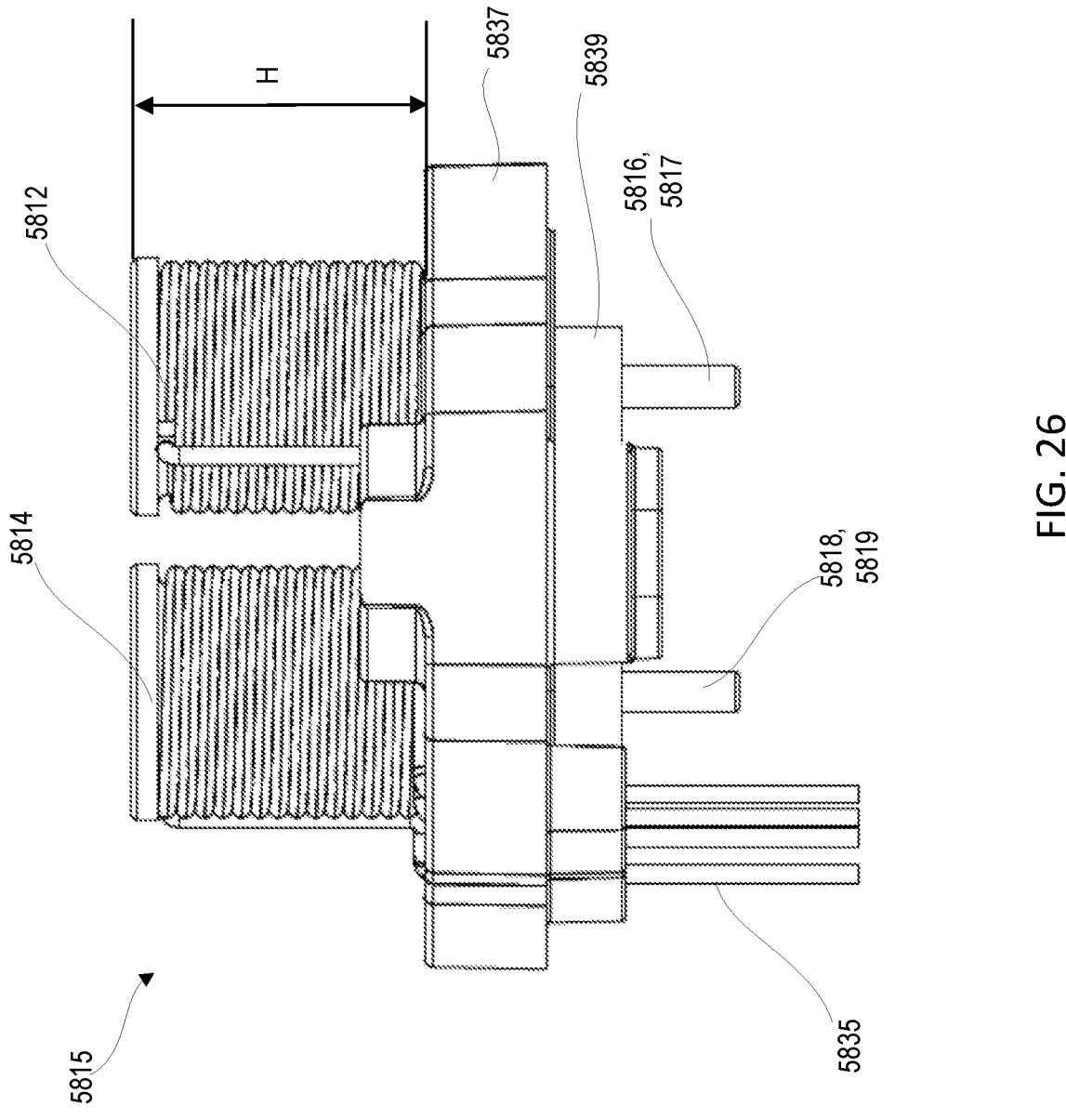
Figure 27:
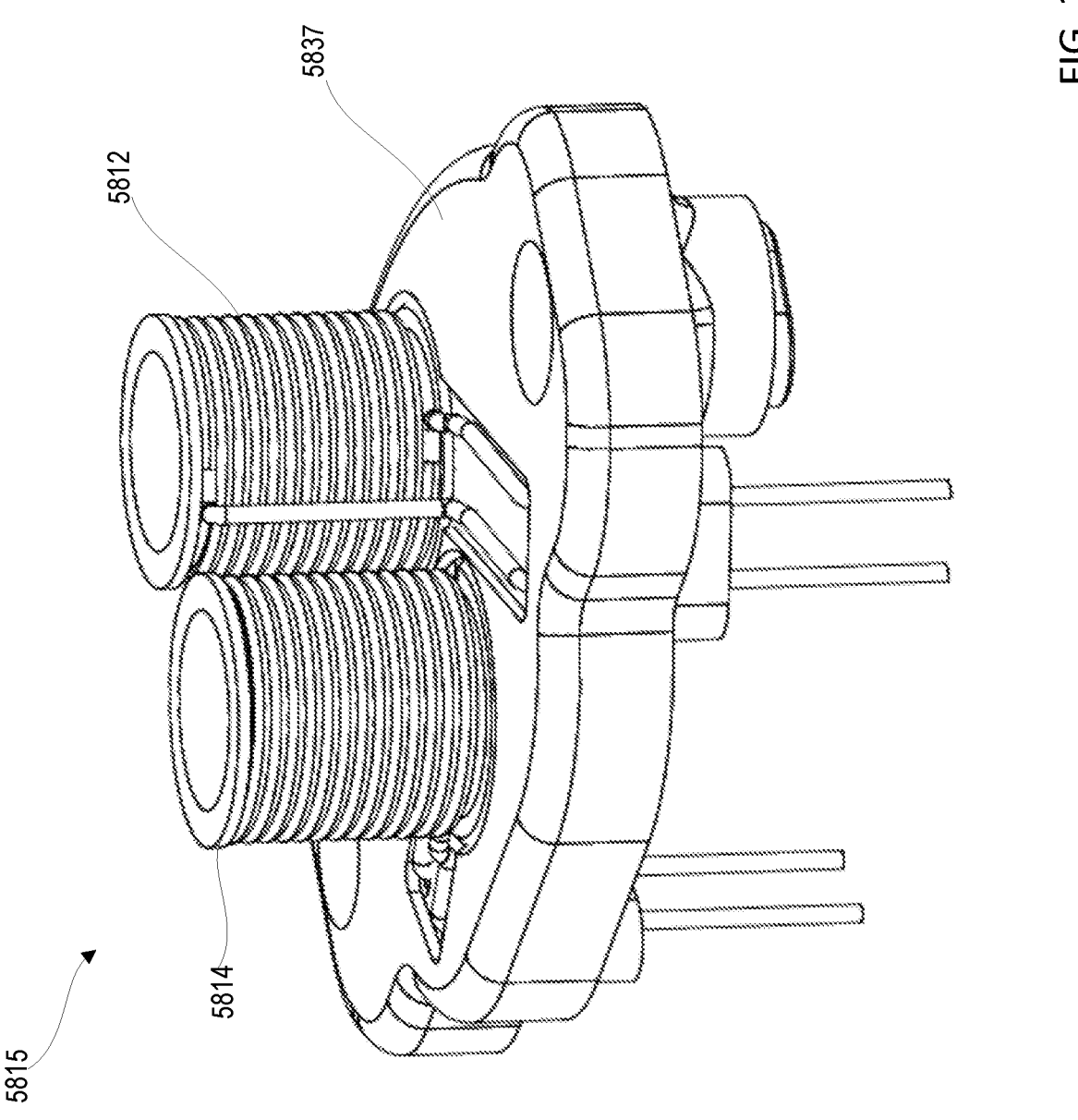

FIGS. 26 and 27 are a side view (FIG. 26) and a perspective view (FIG. 27) of the coil assembly of the force sensor unit of the medical device of FIG. 7A.

Figures 28, 29:
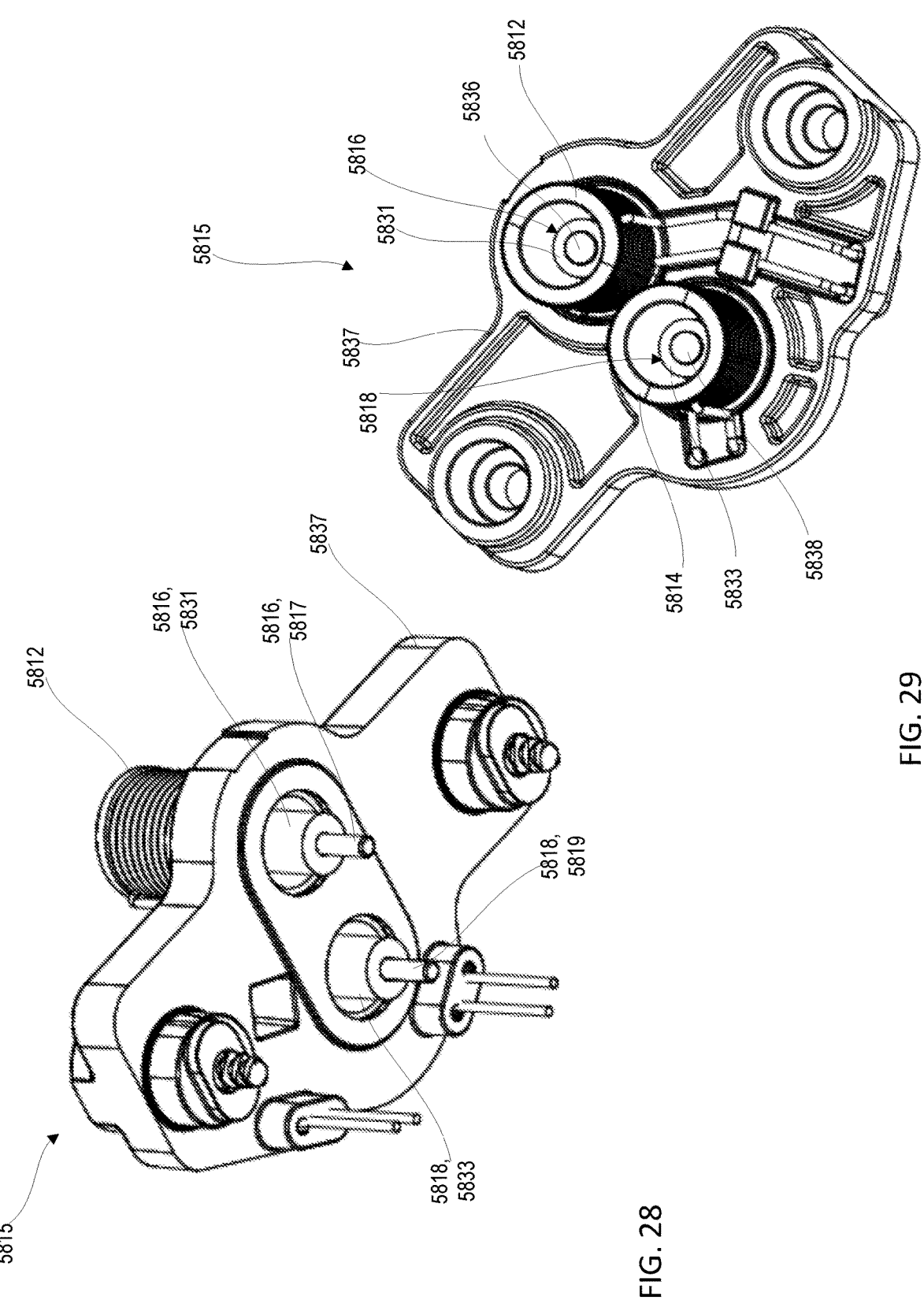

FIGS. 28 and 29 are a bottom perspective view (FIG. 28) and a top perspective view (FIG. 29) of the coil assembly of the force sensor unit of the medical device of FIG. 7A.

Figure 30:
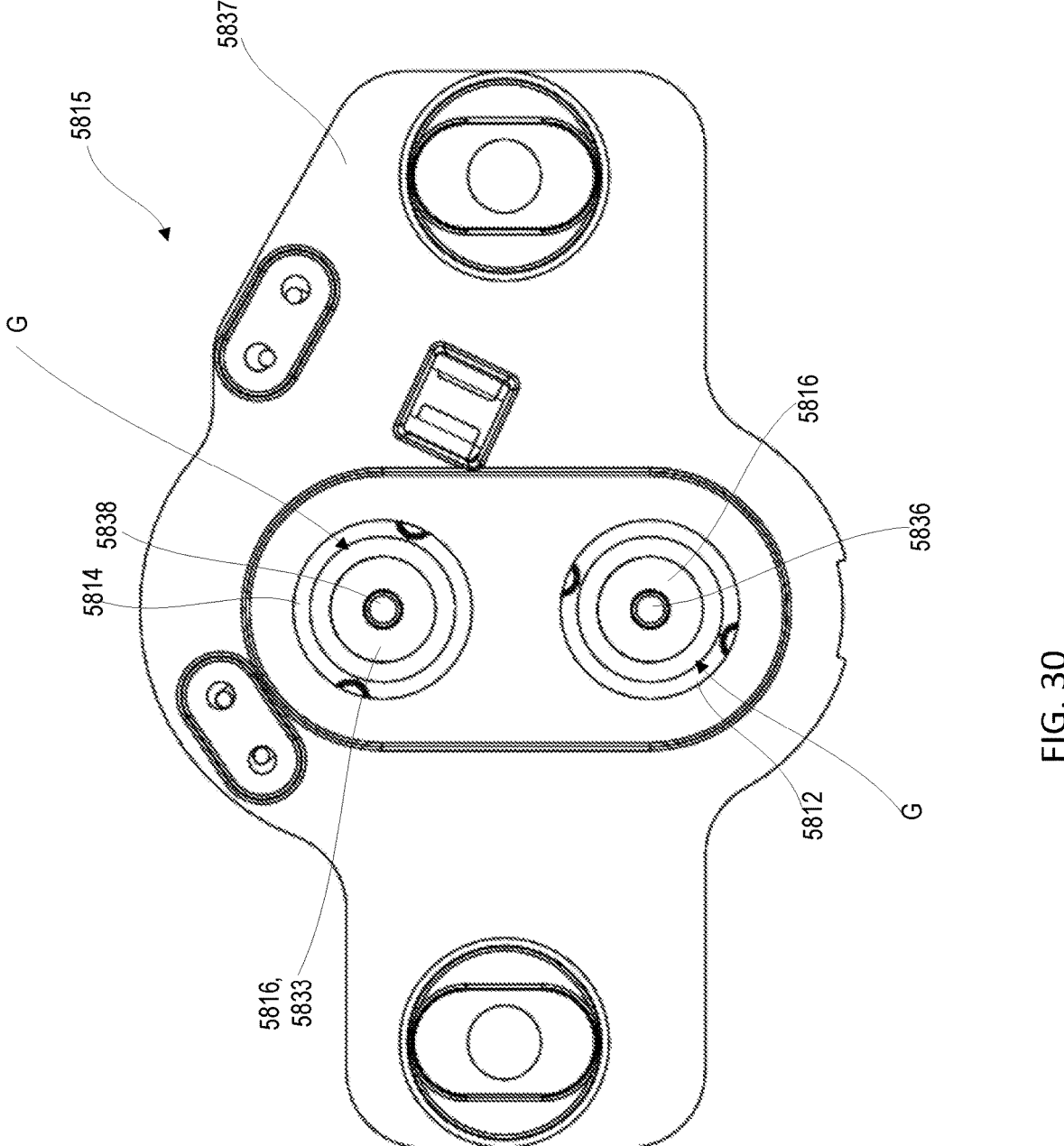

FIG. 30 is a bottom view of the coil assembly of the force sensor unit of the medical device of FIG. 7A.

Figure 31:
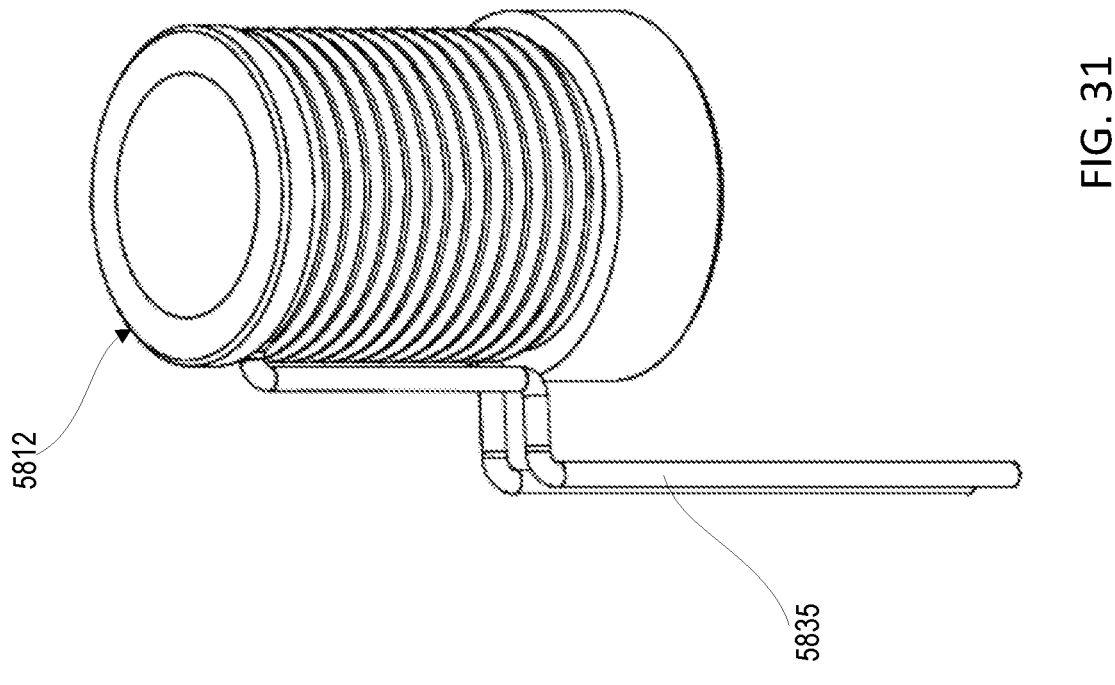

FIG. 31 is a side view of a coil of the coil assembly of the force sensor unit of the medical device of FIG. 7A.

Figure 32:
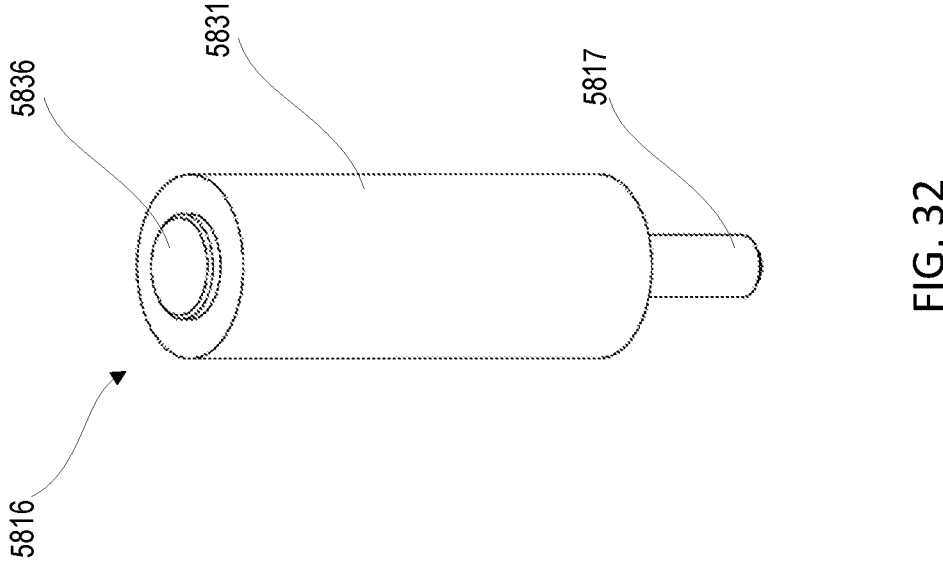

FIG. 32 is a side view of a rod of the coil assembly of the force sensor unit of the medical device of FIG. 7A.

Figure 33:
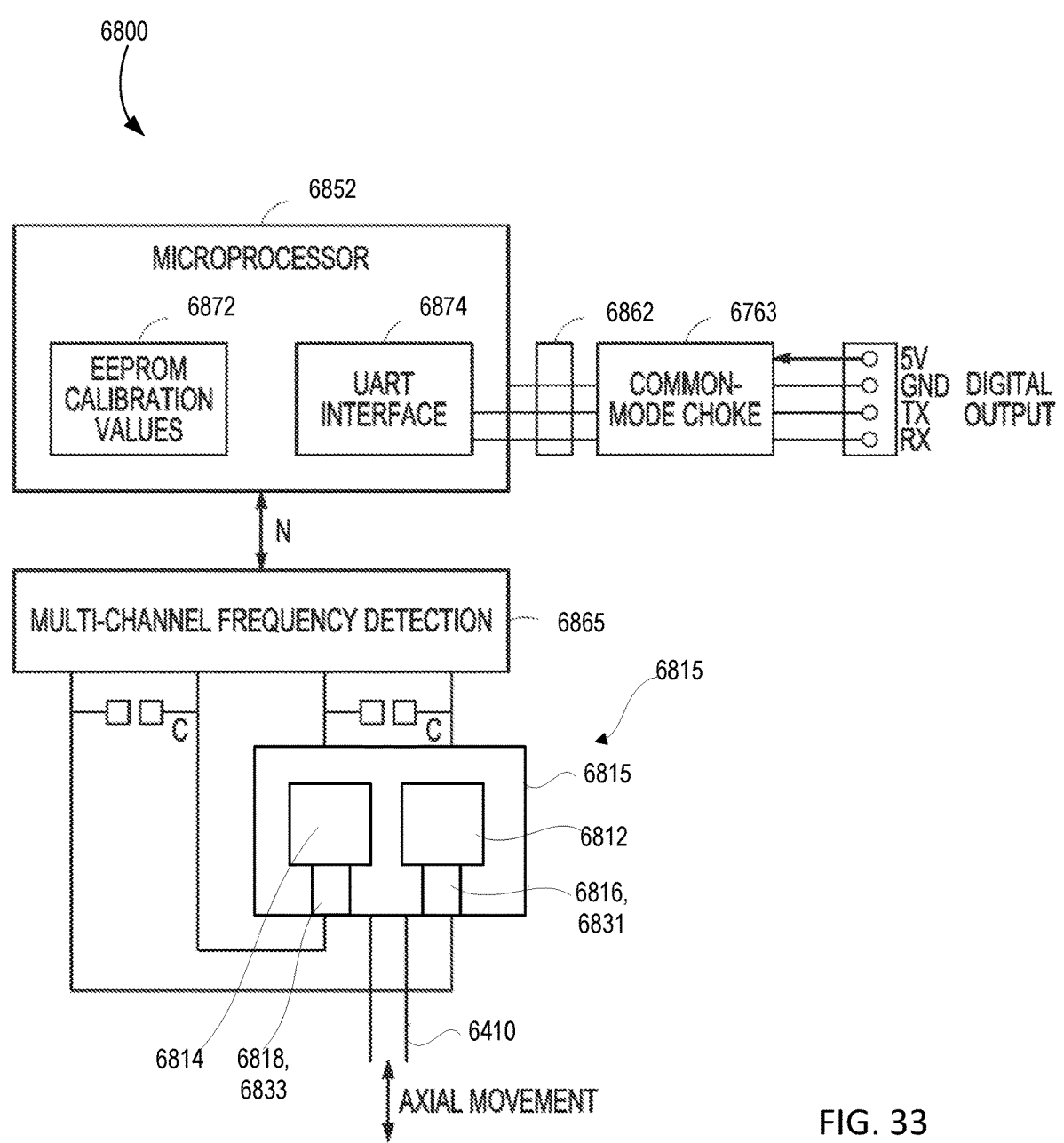

FIG. 33 is a diagrammatic illustration of a portion of a force sensor unit, according to an embodiment.

DETAILED DESCRIPTION

The embodiments described herein can advantageously be used in a wide variety of force sensor applications, such as for grasping, cutting, and manipulating operations associated with minimally invasive surgery. The embodiments described herein can also be used in a variety of non-medical applications such as, for example, teleoperated systems for search and rescue, remotely controlled submersible devices, aerial devices, and automobiles, etc. The medical instruments or devices of the present application enable motion in three or more degrees of freedom (DOFs). For example, in some embodiments, an end effector of the medical instrument can move with reference to the main body of the instrument in three mechanical DOFs, e.g., pitch, yaw, and roll (shaft roll). There may also be one or more mechanical DOFs in the end effector itself, e.g., two jaws, each rotating with reference to a clevis (2 DOFs) and a distal clevis that rotates with reference to a proximal clevis (one DOF). Thus, in some embodiments, the medical instruments or devices of the present application enable motion in six DOFs. The embodiments described herein further can be used to determine the forces exerted on (or by) a distal end portion of the instrument during use.

The medical instruments described herein include a force sensor unit that includes a compact inductive force sensor to measure forces applied to the end effector of the medical instrument axially in the z-axis direction. As described herein, two inductive coils are each wound around a polymeric cylinder and a magnet (e.g., a ferrite bead, EMI (electromagnetic interference) suppression bead, nickel-zinc bead, etc.; the term "magnet" as used herein is described in more detail below) held by a rod is movably positioned within each of the coils. As the magnets are moved axially within their respective coil, a change in inductance at each coil results. The change in inductance at each of the coils can be used to measure changes in position of the instrument shaft, which can be translated to z-axis force measurements. The embodiments described herein can provide for an enhanced linear force output (e.g., within a range of ±2.0 mm (0.080 inches)) and cancellation of temperature effects. The compact inductive force sensors described herein provide for redundancy of force measurements by using two inductive coils positioned side-by-side. This arrangement also reduces the overall height of the force sensor, thereby conserving space within the mechanical structure. Moreover, in some embodiments, the coil and magnet design (e.g., the coil length, width, and thickness of the wire, along with the dimensions of the rod and magnet) can be optimized to ensure that that rod with magnet inside the coils is centered (e.g., in some embodiments with a gap between the inner surface of the coil and the outer surface of the rod with magnet of about 1.33 mm (0.050 inches)). The embodiments described herein can also produce increased linear stroke of the force sensor. In addition, to avoid false force signals being picked up by the sensor, in some embodiments, the two inductive coils are mechanically grounded on the same rigid component of the medical instrument as a spring element, which is part of a linkage that is used to convert force to a displacement measurement (described in more detail below).

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if possesses the ability to absorb energy when it is deformed elastically, and then release the stored energy upon unloading (i.e., returning to its original state). Many "rigid" objects have a slight inherent resilient "bendiness" due to material properties, although such objects are not considered "flexible" as the term is used herein.

As used in this specification and the appended claims, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to the actuation shaft) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® Surgical System, commercialized by Intuitive Surgical, Inc. of Sunnyvale, California. Examples of such surgical systems are the da Vinci Xi® Surgical System (Model IS4000), and the da Vinci X® Surgical System (Model IS4200). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support—i.e., on devices that are either mechanically grounded or ungrounded with reference to a world reference frame.

Figure 1:
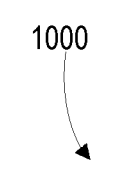
FIG. 1 is a plan view of a minimally invasive teleoperated surgery system according to an embodiment being used to perform a medical procedure such as surgery.

FIG. 1 is a plan view illustration of a computer-assisted teleoperation system. Shown is a medical device, which is a Minimally Invasive Robotic Surgical (MIRS) system 1000 (also referred to herein as a minimally invasive teleoperated surgery system), used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot), and an optional auxiliary equipment unit 1150. The manipulator unit 1200 can include an arm assembly 1300 and a tool assembly removably coupled to the arm assembly. The manipulator unit 1200 can manipulate at least one removably coupled instruments 1400 through a minimally invasive incision in the body or natural orifice of the patient P while the surgeon S views the surgical site and controls movement of the instrument 1400 through control unit 1100. An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of instruments 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 2:
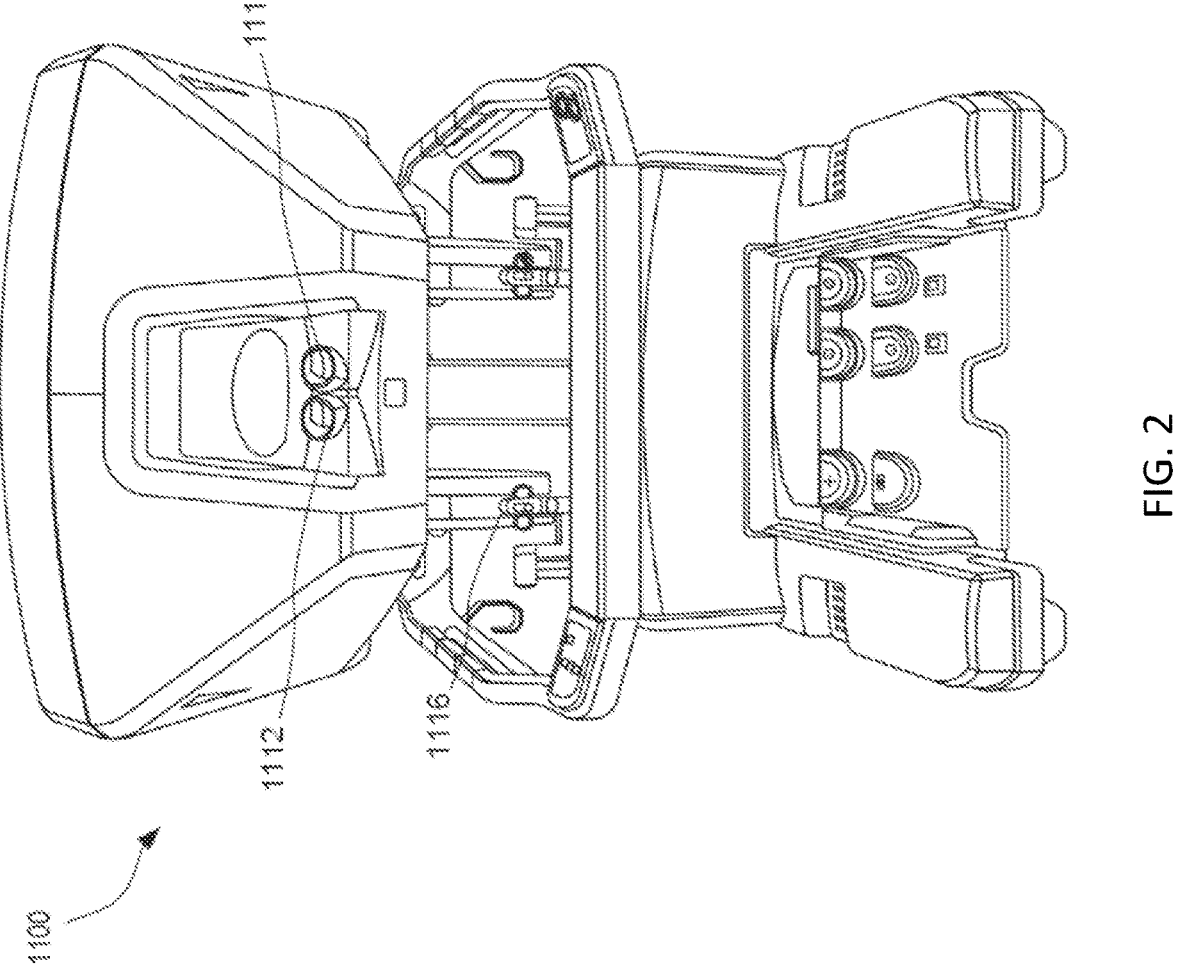
FIG. 2 is a perspective view of an optional auxiliary unit of the minimally invasive teleoperated surgery system shown in FIG. 1.

FIG. 2 is a perspective view of the control unit 1100. The user control unit 1100 includes a left eye display 1112 and a right eye display 1114 for presenting the surgeon S with a coordinated stereo view of the surgical site that enables depth perception. The user control unit 1100 further includes one or more input control devices 1116, which in turn cause the manipulator unit 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, strain and/or tactile feedback sensors (not shown) may be employed to transmit position, force, and tactile sensations from the instruments 1400 back to the surgeon's hands through the input control devices 1116.

The user control unit 1100 is shown in FIG. 1 as being in the same room as the patient so that the surgeon S can directly monitor the procedure, be physically present if necessary, and speak to an assistant directly rather than over the telephone or other communication medium. In other embodiments however, the user control unit 1100 and the surgeon S can be in a different room, a completely different building, or other remote location from the patient allowing for remote surgical procedures.

Figure 3:
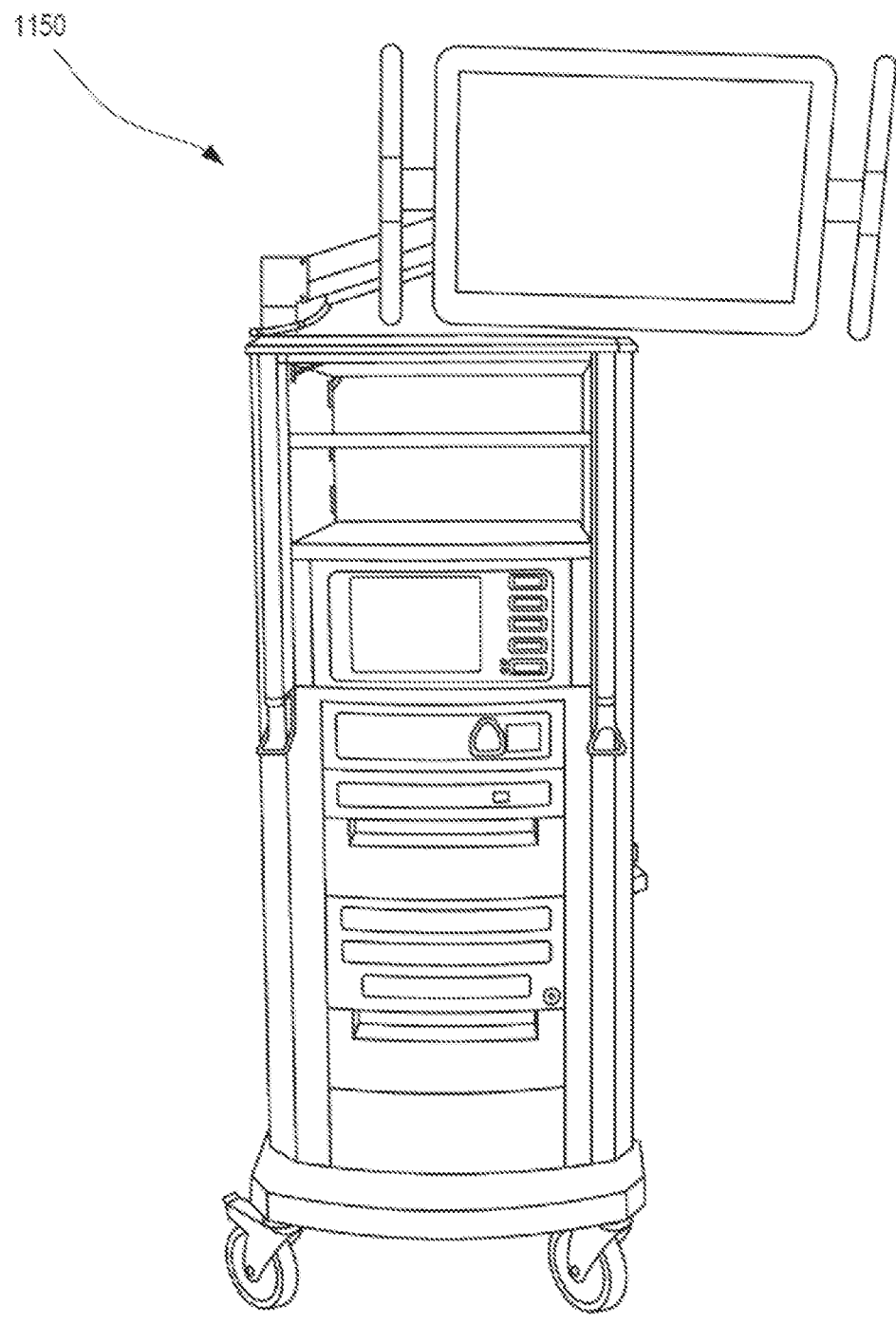
FIG. 3 is a perspective view of a user control console of the minimally invasive teleoperated surgery system shown in FIG. 1.

FIG. 3 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
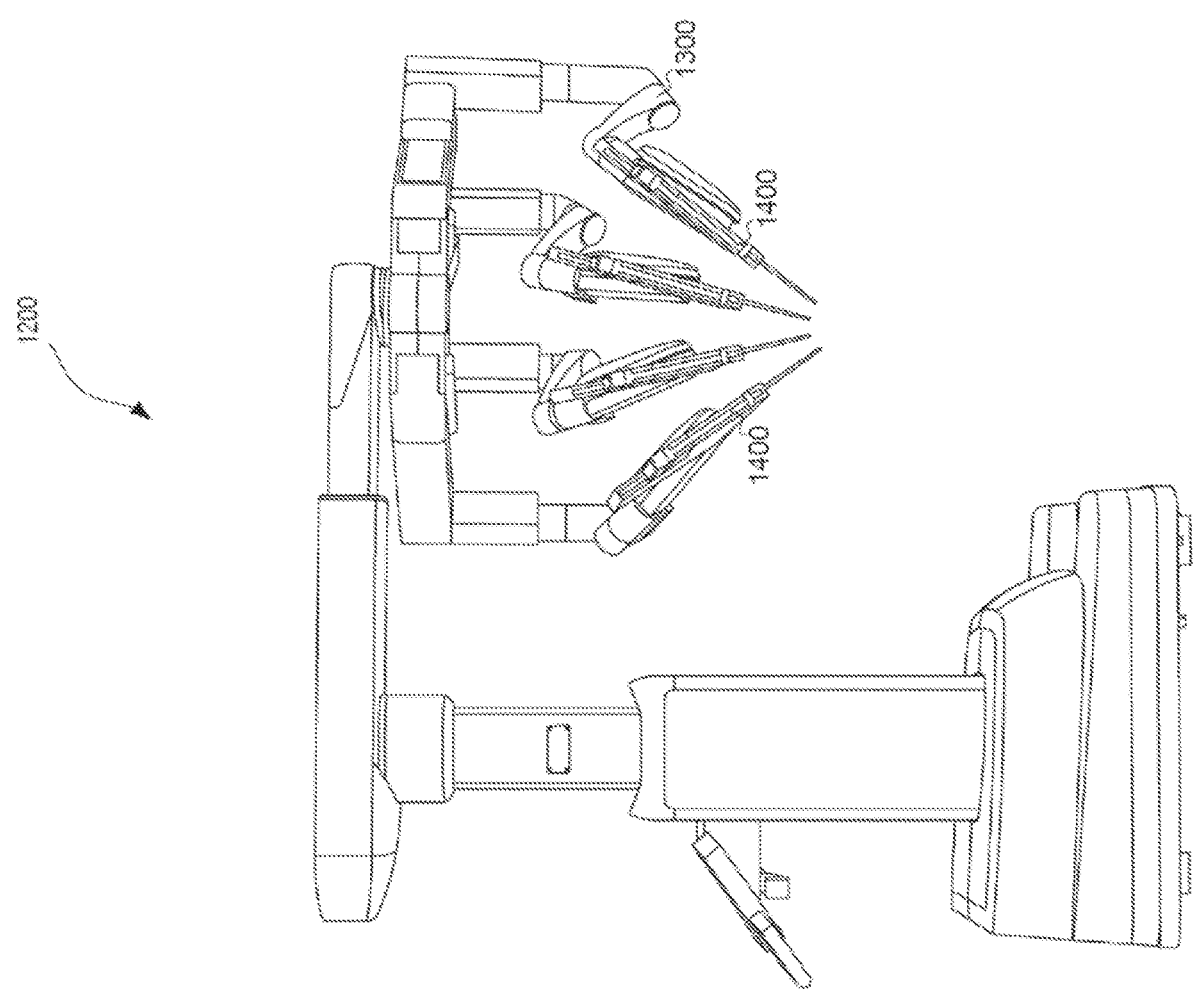
FIG. 4 is a front view of a manipulator unit, including a plurality of instruments, of the minimally invasive teleoperated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having a number of joints. Moreover, the instruments 1400 and the imaging device are positioned and manipulated through incisions or natural orifices in the patient P in a manner such that a software and/or kinematic remote center of motion is maintained at the incision or orifice. In this manner, the incision size can be minimized.

Figure 5:
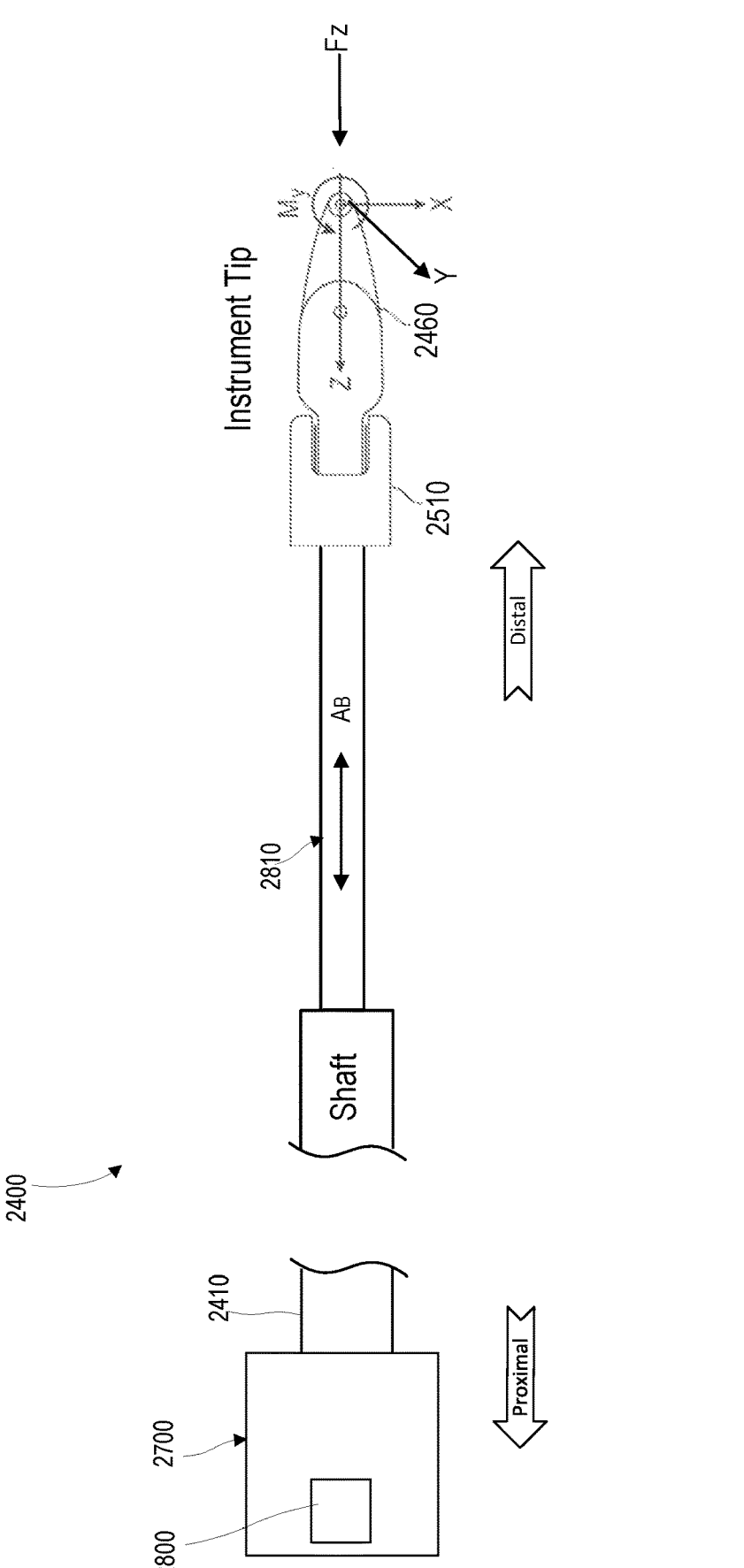
FIG. 5 is a diagrammatic illustration of a medical device including a force sensor unit, according to an embodiment.

FIG. 5 is a schematic illustration of a medical device 2400, according to an embodiment. In some embodiments, the medical device 2400 or any of the components therein are optionally parts of a surgical system that performs surgical procedures, and which can include a manipulator unit, a series of kinematic linkages, a series of cannulas, or the like. The medical device 2400 (and any of the instruments described herein) can be used in any suitable surgical system, such as the MIRS system 1000 shown and described above. The medical device 2400 includes a mechanical structure 2700, a force sensor unit 2800 coupled to or included within the mechanical structure 2700, a shaft 2410 coupled to the mechanical structure 2700, a beam 2810 coupled to the shaft 2410, and an end effector 2460 coupled at a distal end portion of the beam 2810. The end effector 2460 can include, for example, articulatable jaws or another suitable surgical tool that is coupled to a link 2510. In some embodiments, the link 2510 can be included within a wrist assembly having multiple articulating links. The shaft 2410 includes a distal end portion that is coupled to a proximal end portion of the beam 2810. In some embodiments, the distal end portion of the shaft 2410 is coupled to the proximal end portion 2822 of the beam 2810 via another coupling component (such as an anchor or coupler, not shown). The shaft 2410 is also movably coupled at a proximal end portion to the mechanical structure 2700. The mechanical structure 2700 can include components configured to move one or more components of the surgical instrument, such as, for example, the end effector 2460. The mechanical structure 2700 can be similar to the mechanical structure 5700 described in more detail below with reference to medical device 5400.

Generally, during a medical procedure, the end effector 2460 contacts anatomical tissue, which may result in x, y, or z direction forces being imparted on the end effector 2460 and that may result in moment forces such as a moment $M_Y$ about a y-direction axis as shown in FIG. 5. In some embodiments, one or more strain sensors (not shown), which can be strain gauges, can be coupled to the beam 2810 to measure strain in the beam 2810. The measured beam strain can be used to determine forces imparted on the end effector 2460 in the x- and y-axis directions. These x- and y-axis forces are transverse (e.g., perpendicular) to the z-axis (which is parallel or collinear with a center axis $A_B$ of the beam).

The force sensor unit 2800 (and any of the force sensor units described herein) can be used to measure the axial force(s) (i.e., in the direction of the z-axis parallel to the beam center axis $A_B$) imparted on the end effector 2460. For example, an axial force $F_z$ imparted to the end effector 2460 in a direction of the z-axis can cause axial displacement of the shaft 2410 in a direction along a center axis of the shaft (substantially parallel to the beam center axis $A_B$). The axial force $F_z$ may be in the proximal direction (e.g., a reactive force resulting from pushing against tissue with the end effector) or it may be in the distal direction (e.g., a reactive force resulting from pulling tissue grasped with the end effector). As described herein, the shaft 2410 can be coupled to the mechanical structure 2700 via a biasing mechanism (e.g., a linkage or a spring-loaded coupling, not shown) such that the amount of travel of the shaft 2410 relative to the mechanical structure 2700 can be correlated to the magnitude of the axial force $F_z$ imparted to the end effector 2460. In this manner, measuring the distance through which the shaft 2410 moves relative to the mechanical structure 2700 can be used to determine the axial force $F_z$.

The force sensor unit 2800 can include any suitable components to isolate the axial movement of the shaft 2410 (i.e., to constrain the shaft such that the measured movement is caused only by the axial force $F_z$ and not the transverse forces along the x- and y-axes), limit frictional force opposing movement of the shaft 2410 (which can cause errors in determining the axial force $F_z$), and provide redundancy in measuring the movement of the shaft 2410. For example, in some embodiments, the force sensor unit 2800 can include a coil assembly, a linkage, and a microprocessor (each not shown in FIG. 5). The linkage can be any suitable mechanism that movably couples the shaft 2410 to the mechanical structure 2700 in a manner such that the amount of shaft movement can be correlated to the applied axial force $F_z$. For example, the linkage (and any of the linkages described herein) can include four links coupled together within or to the mechanical structure 2700. The linkage includes a first link coupled to the shaft 2410, and a second link that includes or is coupled to a spring, as described in more detail below with reference to the linkage 4850 or 5850 described below. The four links of the linkage maintain connector tension (e.g., connectors used to move the end effector and wrist assembly described in more detail below) within the medical device, and provide for linear movement of the shaft 2410 when forces are applied axially at the distal end of the medical device 2400. The linkage also constrains the movement in the z-axis and isolates forces in the z-axis. As described below, the force sensor unit 2800 measures the z-axis movement of the shaft, which is converted from a position measurement to a force measurement. The amount of travel of the shaft 2410 for a given amount of axial force $F_z$ depends in part on the stiffness of the spring included within the linkage. Thus, the force sensor unit 2800, including the linkage and any springs therein, is calibrated to provide the desired range of motion of the shaft 2410 over the expected range of axial force.

As described herein, the coil assembly (not shown) of the force sensor unit 2800 measures the displacement of the shaft along the z-axis, which is then converted to the force measurement. The coil assembly can include two inductive coils each wound around a cylinder formed from a nonconductive material, such as, for example, PEEK. The two coils can be positioned side-by side to each other and coupled to, or within, the mechanical structure 2700. Within each of the coils is a rod that is movable within an interior of the coil and is coupled to the shaft 2410 of the medical device 2400. The rods can, for example, include a core with a magnet coupled to the core that moves with the rod within the respective coil. The core can be, for example, a glass core, a stainless steel core or a core formed with another suitable material. The magnet and any of the magnets described herein, can be, for example, a ferrite bead, an EMI suppression bead, a nickel-zinc bead, or any other suitable material. Thus, it should be understood that the term "magnet" as used herein can refer to any component or material of the core, or coupled to the core, that can be used to provide a signal indicative of the position of the core within the coil as the rod and core move within the corresponding coil. The rods are operably coupled to the shaft 2410 such that when the shaft 2410 moves axially due to forces imparted on a distal end of the medical device 2400, the rods move with the shaft 2410 and within the coils. As the rods move within the inductive coils, the inductance at each of the coils changes, which can be used to measure changes in position of the instrument shaft. As described above, the change in position of the shaft 2410 can be translated to a z-axis force measurement.

During use of the medical device 2400, as force is imparted on the shaft 2410 in a z direction, the shaft 2410 will travel along the z-axis, which in turn causes the rods to move along the z-axis. As the rods move within the respective coils, each of the coils generate a signal associated with a position of the magnets of the rods within the respective coil. The microprocessor receives the signals from the coils. For example, in some embodiments, each of the coils generate a signal associated with a linear displacement of the shaft along the center axis of the shaft (e.g., along the z-axis). In some embodiments, the signals from the coils can include a first signal from the first coil having a first frequency, and a second signal from the second coil having a second frequency. The microprocessor is configured to execute instructions to determine from the first frequency and the second frequency a measure of a force on the shaft along the center axis of the shaft. Further details regarding the operation and interaction of the microprocessor are described below with reference to FIG. 33.

Figure 6A:
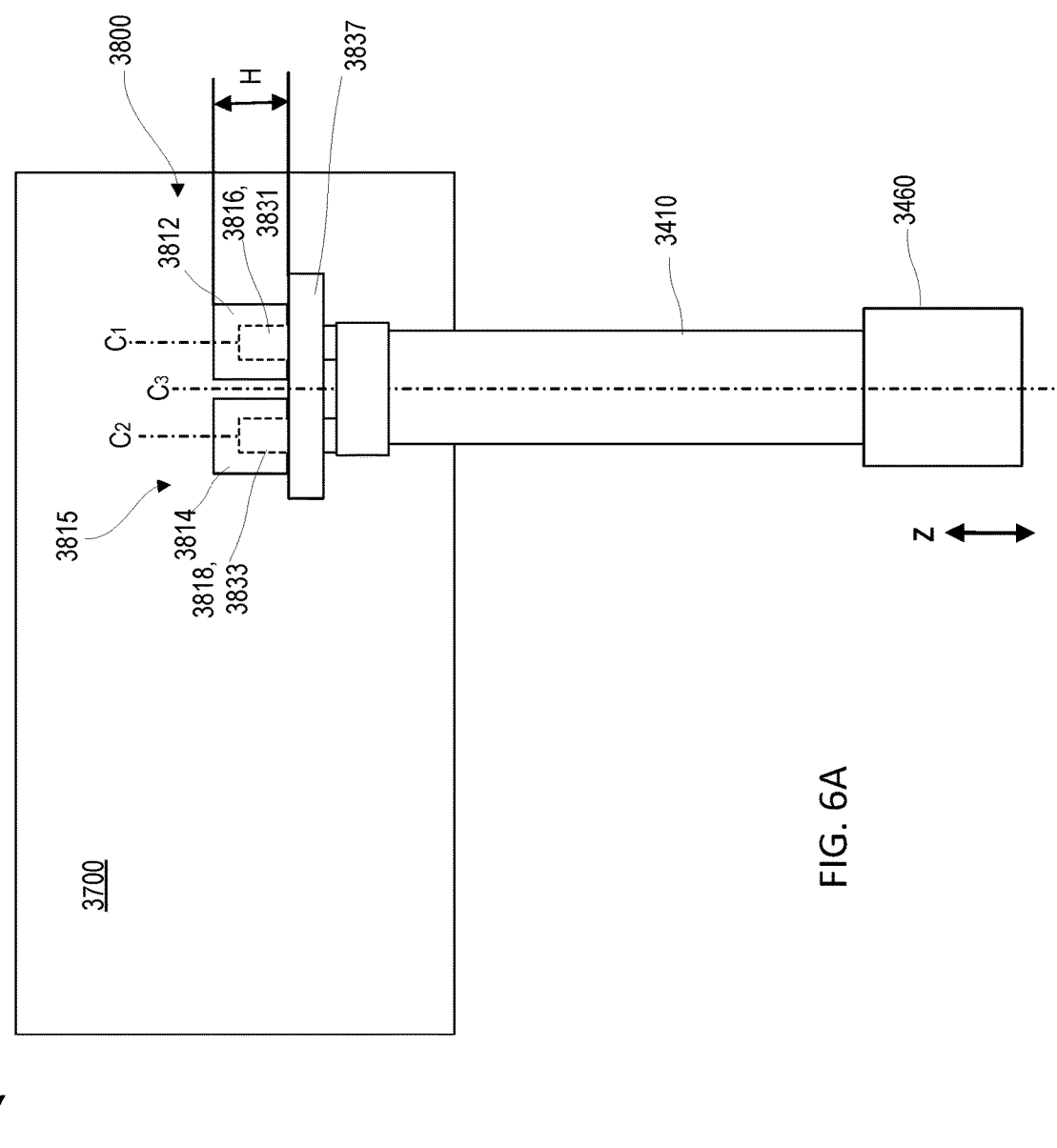
FIG. 6A is a diagrammatic illustration of a portion of a medical device, according to an embodiment.

FIG. 6A is a schematic illustration of another embodiment of a medical device having a force sensor unit that uses an inductive coil as a force sensor. In some embodiments, the medical device 3400 or any of the components therein are optionally parts of a surgical system that performs surgical procedures, and which can include a manipulator unit, a series of kinematic linkages, a series of cannulas, or the like. The medical device 3400 (and any of the instruments described herein) can be used in any suitable surgical system, such as the MIRS system 1000 shown and described above. The medical device 3400 includes a mechanical structure 3700, a force sensor unit 3800, a shaft 3410 coupled to the mechanical structure 3700 and to the force sensor unit 3800, and an end effector 3460 coupled at a distal end portion of the medical device 3400. As described above, the end effector 3460 can include, for example, articulatable jaws or another suitable surgical tool and can be coupled to a link (not shown). In some embodiments, the link can be included within a wrist assembly having multiple articulating links.

The shaft 3410 defines a center axis $C_3$ and includes a distal end portion that is coupled to the end effector 3460. In some embodiments, the distal end portion of the shaft 3410 is coupled to the end effector by a beam that can be used to measure transverse force applied thereto (e.g., similar to the beam 2810). In other embodiments, the shaft 3410 can be directly coupled to a link, wrist joint (not shown), or the end effector 3460. The shaft 3410 is movably coupled at a proximal end portion to the mechanical structure 3700. Thus, axial forces applied to the end effector 3460 will produce movement of the shaft 3410 relative to the mechanical structure 3700, which can be measured using the force sensor unit 3800, as described herein. The mechanical structure 3700 can include components configured to move one or more components of the surgical instrument, such as, for example, the end effector 3460. The mechanical structure 3700 can be similar to the mechanical structure 5700 described in more detail below with reference to medical instrument 5400.

The force sensor unit 3800 includes a coil assembly 3815 that includes a first coil 3812, a second coil 3814, a first rod 3816, a second rod 3818, a first magnet 3831, a second magnet 3833 and a mounting bracket 3837. The first coil 3812 and the second coil 3814 are each inductive coils wound around a cylinder formed from a nonconductive material, such as, for example, PEEK. The first coil 3812 and the second coil 3814 are each secured to the mounting bracket 3837 (which is coupled to or included within the mechanical structure 3700) and are positioned in a side-by-side relation to each other. Similarly stated, the first coil 3812 and the second coil 3814 are mounted within the mechanical structure 3700 in a non-coaxial arrangement. The coils 3812 and 3814 extend from the mounting bracket a distance or height H as shown in FIG. 6A. The non-coaxial arrangement of the coils reduces the overall height of the force sensor unit 3800, thereby conserving space within the mechanical structure 3700. Although the two coils are shown as extending from the mounting bracket 3837 by the same distance, in other embodiments, the height of the first coil 3812 can be different from the height of the second coil 3814.

The first rod 3816 is coupled to the shaft 3410 and is movably disposed within the first coil 3812. Specifically, the first rod 3816 defines a center axis $C_1$ along which the first rod 3816 (and the first magnet 3831) translate within the first coil 3812. The second rod 3818 is coupled to the shaft 3410 and is movably disposed within the second coil 3814. The second rod 3818 defines a center axis $C_2$ along which the second rod 3818 (and the second magnet 3833) translate within the second coil 3814. As shown, the center axis $C_2$ of the second rod 3818 is noncoaxial with the center axis $C_1$ of the first rod 3816. The first rod 3816 and the second rod 3818 can each include a core formed with, for example, a glass material or stainless steel, with a magnet coupled thereto. As described above for previous embodiments, the core can be, for example, a glass core, a stainless steel core or a core formed with another suitable material. The magnets 3831 and 3833 can be, for example, a ferrite bead, an EMI suppression bead, a nickel-zinc bead, or any other suitable material or any component or material of the core, or coupled to the core, that can be used to provide a signal indicative of the position of the core within the respective coils 3812 and 3814, as the rods 3816 and 3818 and cores move within the respective coils. More specifically, the first magnet 3831 is coupled to the first rod 3816 and the second magnet is coupled to the second rod 3818, such that the first magnet 3831 moves with the first rod 3816 and the second magnet 3833 moves with the second rod 3818. As described above, the first and second rods 3816 and 3818 are coupled to the shaft 3410, such that when the shaft 3410 moves axially due to forces imparted on a distal end of the medical device 3400 (e.g., at the end effector 3460), the rods 3816 and 3818 move with the shaft 3410 and within the coils 3812 and 3814, respectively. As the rods 3816 and 3818 and magnets 3831 and 3833 move within the inductive coils 3812 and 3814, the inductance at each of the coils changes, which can be used to measure changes in position of the shaft 3410. The change in position of the shaft 3410 can be translated to z-axis force measurements.

As shown, the first rod 3816 (with magnet 3831 coupled thereto) is positioned substantially centered within the first coil 3812. Thus, the center axis $C_1$ of the first rod 3816 is coaxial with a center axis of the first coil 3812. The clearance between an outer surface of the first rod 3816 and an inner surface of the first coil 3812 can be of any suitable value to allow for tolerance errors in the placement of the rods and reduce the likelihood of contact between the first rod 316 and the first coil 3812. This is desirable because inner friction between the rods and the coil can lead to false force readings in the z-axis. Similarly, the second rod 3818 (with magnet 3833 coupled thereto) is positioned substantially centered within the second coil 3814. Thus, the center axis $C_2$ of the second rod 3818 is coaxial with a center axis of the second coil 3814. As described for the first coil 3812 and the first rod 3814, the clearance between an outer surface of the second rod 3818 and an inner surface of the second coil 3814 can be of any suitable value. In some embodiments, the clearance for each of the coil/rod pairs can be about 1.3 mm (0.050 inches).

In some embodiments, the center axis $C_3$ of the shaft 3410 is between the center axis $C_1$ of the first rod 3816 and the center axis $C_2$ of the second rod 3818, as shown in FIG. 6A. In some embodiments, the center axis $C_3$ of the shaft 3410 is parallel to the center axes $C_1$ and $C_2$ of the first rod 3816 and the second rod 3816, respectively. In some embodiments, the center axis $C_3$ of the shaft 3410 is centered between the center axis $C_2$ of the first rod 3816 and the center axis $C_2$ of the second rod 3818.

In some embodiments, the medical device 3400 can also include a linkage and a microprocessor (each not shown in FIG. 6A) as described above for medical device 2400. The linkage can be any suitable mechanism that movably couples the shaft 3410 to the mechanical structure 3700 in a manner such that the amount of shaft movement can be correlated to the applied axial force $F_z$. For example, the linkage (and any of the linkages described herein) can include four links coupled together within or to the mechanical structure 3700. The linkage can include a first link coupled to the shaft 3410 and a second link that includes or is coupled to a spring, as described in more detail below with reference to specific embodiments. The four links of the linkage maintain connector tension within the medical device 3400, and the linkage provides for linear movement of the shaft 3410 when forces are applied axially at the distal end of the medical device 3400. The linkage can also constrain the movement to be in the z-axis (the slight lateral movement of the shaft at small z-axis displacements involved with z-axis force sensing is negligible) and isolates forces in the z-axis. As described above, the force sensor unit 3800 measures the change in the inductance within the coils due to the z-axis movement of the shaft (i.e., along the center axis $C_3$ of the shaft 3410), which is converted from position to force.

The amount of travel of the shaft 3410 for a given amount of axial force $F_z$ depends in part on the stiffness of the spring included within the linkage. Thus, as described above for previous embodiments, the force sensor unit 3800, including the linkage and any springs therein, is calibrated to provide the desired range of motion of the shaft 3410 over the expected range of axial force. The spring can translate the applied axial forces into a displacement signal. As described above, the link with the spring and the coil assembly 3815 can be grounded to the same rigid component of the mechanical structure 3700 such that false force signals due to a difference in deflection in different grounding components can be avoided.

During use of the medical device 3400, as force is imparted on the shaft 3410 in a z-axis direction, the shaft 3410 will travel along the z-axis, which in turn causes the rods 3816 and 3816 to translate along the z-axis (along their respective center axes; again, any lateral motion is negligible at shaft displacements associated with z-axis force sensing). As the rods 3816 and 3818 move within the respective coils (3812 and 3814), each of the coils 3812 and 3816 generate a signal associated with a position of the magnets 3831 and 3833 within the respective coil 3812 and 3814. Thus, each of the coils generates a signal associated with a linear displacement of the shaft along the center axis $C_3$ of the shaft 3410 (i.e., along the z-axis). The microprocessor (not shown) receives these signals from the coils 3812 and 3814. In some embodiments, the signals from the coils can include a first signal from the first coil having a first frequency, and a second signal from the second coil having a second frequency. The microprocessor is configured to execute instructions to determine from the first frequency and the second frequency a magnitude of a force on the shaft 3410 along the center axis $C_3$ of the shaft 3410.

In some embodiments, the first coil 3812 and the second coil 3814 have the same configuration (e.g., coil diameter, number of windings, type of wire, coil height, etc.). The side-by-side positioning and the identical configuration of the coils 3812 and 3814 provides a fully redundant inductive force sensor that can also fit within the constrained space of the mechanical structure 3700. Parameters that contribute to the ability to achieve a redundant force sensor configuration are the coil length (or height), width, and thickness of the coil wire, and the dimensions of the rods such that an optimal size of the coils can be achieved and the linear range of the rods within the coils can be increased. The coils 3812 and 3814 have identical dimensions (e.g., height, wire diameter, width, material), are wound separately, and are coupled to the coil mounting bracket 3837 such that they are disposed at the same height H within the medial device 3400. In this manner, each coil 3812 and 3814 provides a separate signal, which can be tracked and compared simultaneously. Because the coils 3812 and 3814 have identical dimensional and material parameters, the coils 3812 and 3814 can have a similar temperature response to their environment.

In addition to providing for full redundancy, the coaxial arrangement of the coils also allows for improved centering of the rods within the coils. Thus, the force sensor unit 3800 can measure force linearly within a desired (increased) travel range of the rods 3816 and 3818. Including a higher linear range of measurement can allow for the inclusion of a linkage spring (not shown) having lower stiffness, which thereby allows the shaft 3410 to move through a greater distance when an axial force is applied to the end effector 3460. In this manner, the force sensor unit 3800 provides a high dynamic range (i.e., the ability to accurately measure displacement of the shaft 3410, and thus the axial force, over a wide range of values). In addition to providing a longer linear range of travel of the rods, positioning the two coils 3812 and 3814 in an adjacent configuration allows for reducing the height H of the coils 3812 and 3814, while still maintaining the desired inductance (which can be, for example, in the range of 0-2 µH).

Figure 6B:
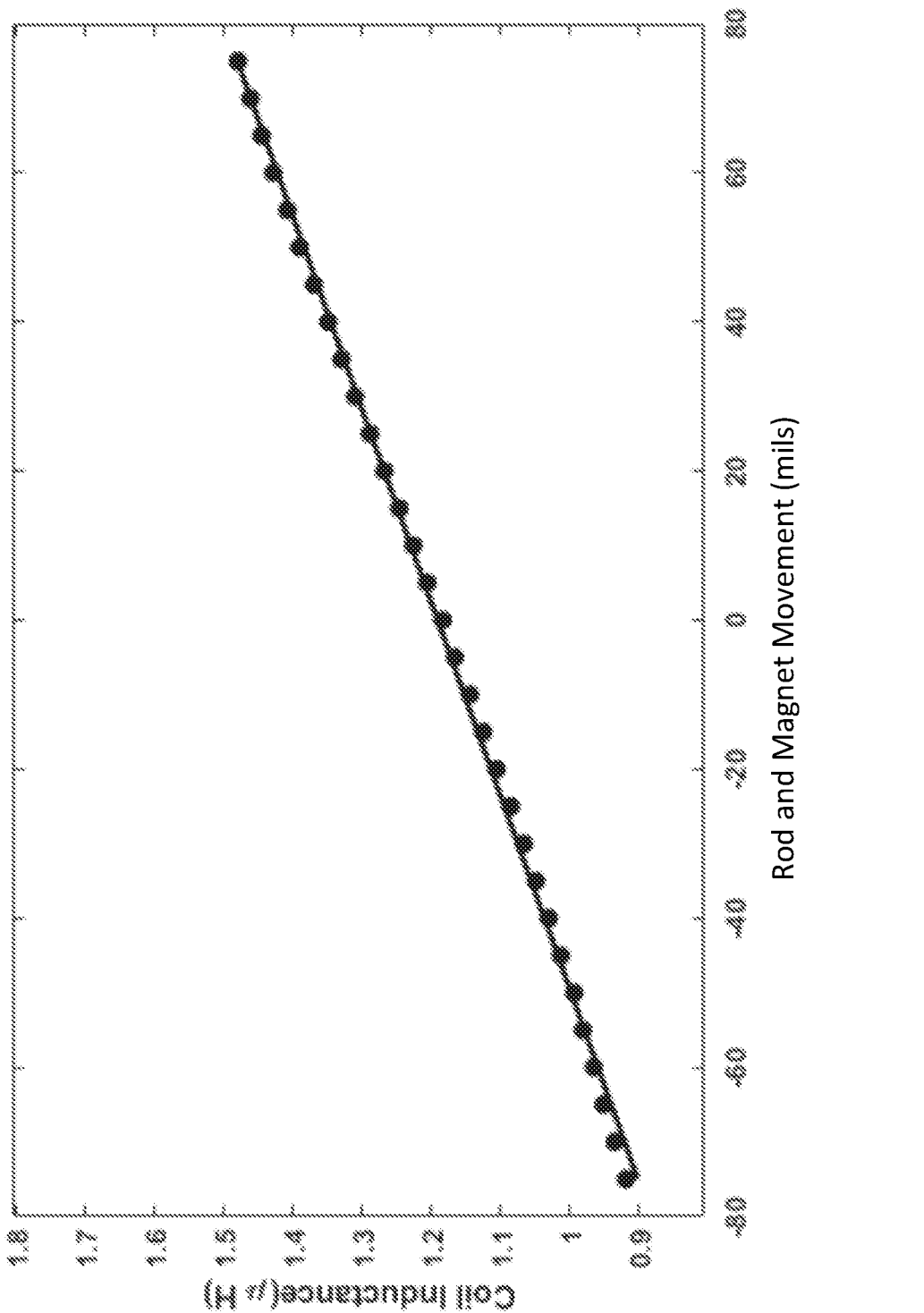
FIG. 6B is a graph illustrating coil inductance versus linear range of rods within a force sensor unit of a medical device, according to an embodiment.

In some embodiments, the force sensor unit 3800 can linearly measure displacement of the shaft 3410 over a range, for example, of ±2 mm (0.080 inches). The range of displacement of the shaft 3410 can vary based on factors, such as, for example, the particular configuration, the stiffness of the shaft 3410, etc. Similarly stated, in some embodiments, the force sensor unit 3800 can produce a linear relationship between the coil inductance and the movement of the rods 3816 and 3818 inside the coils 3812 and 3814 over a range of ±2 mm (0.080 inches). This is achieved, in part, by coupling the rods 3816 and 3818 within the coils 3812 and 3814, respectively, such that a gap between an outer surface of the rods 3816 and 3818 and an inner surface of the coils 3812 and 3814 is about 1.3 mm (0.050 inches) as described above. This linear performance is shown in FIG. 6B, which is a graph illustrating the coil inductance and corresponding rod (i.e., ferrite bead) movement along the z-axis. The configuration of the coils and rods, provides for inductance of the coils to be optimized to be linear with a rod stroke of ±2 mm (0.080 inches), as shown in the graph of FIG. 6B. The linearity was represented with an error of less than 1 percent. This longer travel range allows for the use of a spring in the four-bar linkage mechanism that can be less stiff, which can improve system stability and dynamic range (as discussed above). This configuration is also more tolerant to shifts in the rod position due to thermal expansion, vibration, and shock.

Figure 6C:
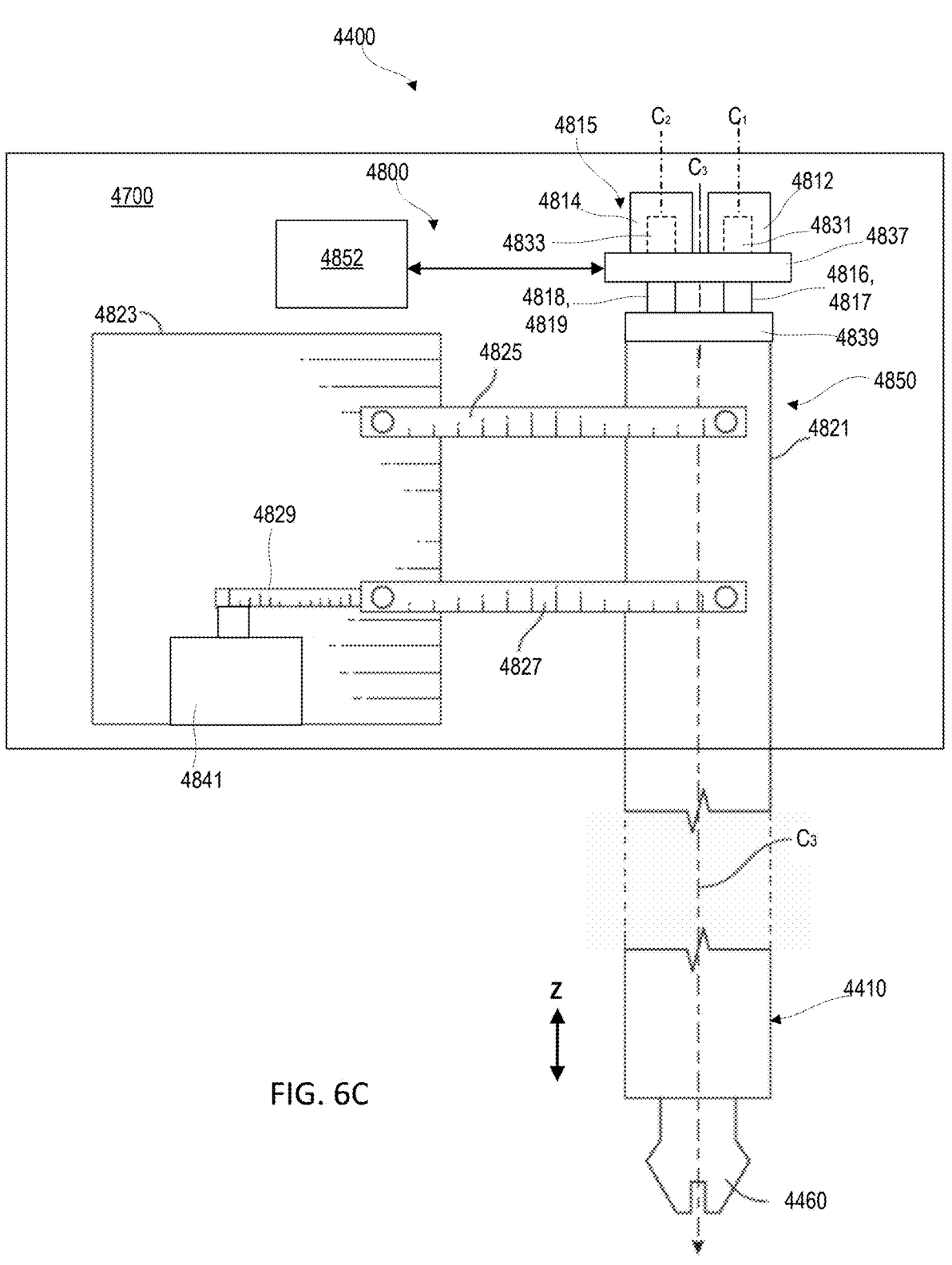
FIG. 6C is a diagrammatic illustration of a portion of a medical device, according to an embodiment.

FIG. 6C is a schematic illustration of another embodiment of a medical device having a force sensor unit 4800 that uses two coaxially-arranged inductive coils to measurement movement of the shaft 4410, thereby acting as a force sensor. In some embodiments, the medical device 4400 or any of the components therein are optionally parts of a surgical system that performs surgical procedures, and which can include a manipulator unit, a series of kinematic linkages, a series of cannulas, or the like. The medical device 4400 (and any of the instruments described herein) can be used in any suitable surgical system, such as the MIRS system 1000 shown and described above. The medical device 4400 includes a mechanical structure 4700, a force sensor unit 4800, a shaft 4410 coupled to the mechanical structure 4700 and to the force sensor unit 4800, and an end effector 4460 coupled at a distal end portion of the medical device 4400. As described above, the end effector 4460 can include, for example, articulatable jaws or another suitable surgical tool and can be coupled to a link (not shown). In some embodiments, the link can be included within a wrist assembly having multiple articulating links. The shaft 4410 can be coupled at a proximal end portion to the mechanical structure that can be configured to move one or more components of the surgical instrument, such as, for example, the end effector 4460. The mechanical structure can be similar to the mechanical structure 5700 described in more detail below with reference to medical instrument 5400.

The force sensor unit 4800 includes a coil assembly 4815, a linkage 4850 and a microprocessor 4852. The coil assembly 4815 includes a first coil 4812, a second coil 4814, a first rod 4816, a second rod 4818, a first magnet 4831, a second magnet 4833 and a mounting bracket 4837. The first coil 4812 and the second coil 4814 are each inductive coils wound around a cylinder formed from a nonconductive material, such as, for example, PEEK, positioned side-by side to each other (as shown in FIG. 6C) and coupled to, or within, the mechanical structure in a non-coaxial arrangement. The non-coaxial arrangement of the coils reduces the overall height of the force sensor unit 4800, thereby con-serving space within the mechanical structure 4700. Although the two coils are shown as extending from the mounting bracket 4837 by the same distance, in other embodiments, the height of the first coil 4812 can be different from the height of the second coil 4814.

The first rod 4816 is coupled to the shaft 4410 and movably disposed within the first coil 4812. Specifically, the first rod 4816 defines a center axis $C_1$ along which the first rod 4816 (and the first magnet 4831) translate within the first coil 4812. The second rod 4818 is coupled to the shaft 4410 and movably disposed within the second coil 4814. The second rod 4818 defines a center axis $C_2$ along which the second rod 4818 (and the second magnet 4833) translate within the second coil 4814. As shown, the center axis $C_2$ of the second rod 4818 is noncoaxial with the center axis $C_1$ of the first rod 4816. The first rod 4816 includes a support portion 4817 and the second rod 4818 includes a support portion 4819 each of which is coupled to the shaft 4410. The first rod 4816 and the second rod 4818 can each include a core with a magnet coupled thereto. As described above for previous embodiments, the cores can be, for example, a glass core, a stainless steel core or a core formed with another suitable material. The magnets 4831 and 4833 can be, for example, a ferrite bead, an EMI suppression bead, a Nickel-zinc bead, or any other suitable material or any component or material coupled to the core that can be used to provide a signal indicative of the position of the core within the respective coils 4812 and 4814, as the rods 4816 and 4818 and cores move within the respective coils 4812 and 4814. The first magnet 4831 is coupled to the first rod 4816 and the second magnet 4833 is coupled to the second rod 4818, such that the first magnet 4831 moves with the first rod 4816 and the second magnet 4833 moves with the second rod 4818. As described above, the first and second rods 4816 and 4818 are coupled to the shaft 4410, such that when the shaft 4410 moves axially due to forces imparted on a distal end of the medical device 4400 (e.g., at the end effector 4460), the rods 4816 and 4818 move with the shaft 4410 and within the coils 4812 and 4814, respectively. As the rods 4816 and 4818 and magnets 4831 and 4833 move within the inductive coils 4812 and 4814, the inductance at each of the coils changes, which can be used to measure changes in position of the shaft 4410. The change in position of the shaft 4410 can be translated to z-axis force measure-ments.

The first rod 4816 (with magnet 4831 coupled thereto) is positioned substantially centered within the first coil 4812. Thus, the center axis $C_1$ of the first rod 4816 is coaxial with a center axis of the first coil 4812. The clearance between an outer surface of the first rod 4816 and an inner surface of the first coil 4812 can be, for example, about 1.3 mm (0.050 inches). Similarly, the second rod 4818 (with magnet 4833 coupled thereto) is positioned substantially centered within the second coil 4814. Thus, the center axis $C_2$ of the second rod 4818 is coaxial with a center axis of the second coil 4814. The clearance between an outer surface of the second rod 4818 and an inner surface of the second coil 4814 can be, for example, about 1.3 mm (0.050 inches). As described above, this gap allows for tolerance errors in the placement of the rods and reduces the incidences of friction. This is desirable because inner friction between the rods and the coil can lead to false force readings in the z-axis.

The first coil 4812 and the second coil 4814 are each secured to the mounting bracket 4837 and are positioned in a side-by-side relation to each other. The mounting bracket 4837 is coupled to or included within the mechanical structure 4700. In some embodiments, a center axis $C_3$ of the shaft 4410 is between the center axis $C_1$ of the first rod 4816 and the center axis $C_2$ of the second rod 4818 as shown in FIG. 6C. In some embodiments, the center axis $C_3$ of the shaft 4410 is parallel to the center axes $C_1$ and $C_2$ of the first rod 4816 and the second rod 4816, respectively. In some embodiments, the center axis $C_3$ of the shaft 4410 is centered between the center axis $C_2$ of the first rod 4816 and the center axis $C_2$ of the second rod 818.

The shaft 4410 is coupled to the mechanical structure 4700 via the linkage 4850 such that the amount of travel of the shaft 4410 relative to the mechanical structure 4700 can be correlated to the magnitude of the axial force imparted to the end effector 4460. In this manner, measuring the distance through which the shaft 4410 moves relative to the mechani-cal structure 4700 can be used to determine the axial force. As described herein, the linkage 4850 isolates the axial movement of the shaft 4410 (i.e., constrains the shaft movement such that the measured movement is caused only by the axial force and not by the transverse forces along the X and Y axes), limits frictional force opposing movement of the shaft 4410, and provides suitable structure for the coaxially arranged coils as described above. As shown, the linkage 4850 includes four links coupled together within or to the mechanical structure 4700. More specifically, the linkage 4850 includes a first link 4821 coupled to the shaft 4410 and to the coil assembly 4815, a second link 4827 that is coupled to the first link 4821 and is coupled to a support mount 4841. The second link 4827 includes (or is coupled to) a spring element 4829 that is coupled to or supported by the support mount 4841, as shown in FIG. 6B. The linkage 4850 also includes a third link 4825 coupled to the first link 4821, and a fourth link 4823 coupled to the second link 4827 and the third link 4827. The fourth link 4823 is stationary and acts as a local mechanical ground for the other three links, which move when the shaft 4410 is moved along its axis $C_3$. The four links of the linkage 4850 can maintain connector tension within the medical device 4400, and provide for linear movement of the shaft 4410 when forces are applied axially at the distal end of the medical device 4400. The linkage 4850 can also constrain the movement in the z-axis and isolates forces in the z-axis. As described above, the force sensor unit 4800 measures the change in the inductance within the coils that results from the z-axis movement of the shaft (i.e., along the center axis $C_3$ of the shaft 3410), which is converted from position value to a magnitude of the axial force.

The support portion 4817 and the support portion 4819 of the rods 4816 and 4818 each extend through an opening in the mounting bracket 4837 and are coupled to the first link 4821, and thus they are coupled to the shaft 4410. For example, in some embodiments, the support portions 4817 and 4819 can be press fit to the first link 4821. In some embodiments, as shown in FIG. 6C, the support portions 4817 and 4819 are coupled (e.g., press fit or by another suitable coupling method) to a bracket 4839, which is coupled to the first link 4821.

The amount of travel of the shaft 4410 in response to an axial force depends in part on the stiffness of the spring 4829 of the second link 4827. For example, if the spring 4829 is very stiff, the shaft 4410 will only move a short distance when an axial force is applied to the end effector 4460. Conversely, if the spring 4829 is less stiff, the same axial force will produce greater movement of the shaft 4410. Thus, the spring 4829 can be selected to have the desired stiffness such that the total travel of the shaft 4410 over the expected range of axial forces to be applied will be within the dynamic range of the force sensor unit 4800.

As described above, in some embodiments, the second link 4827 (with the spring 4829) and the coil assembly 4815 can be grounded to the same rigid component of the mechanical structure 4700. This arrangement reduces the likelihood of erroneous force signals due to a difference in deflection of the components of the force sensor unit 4800, which could be caused by different grounding of the components.

During use of the medical device 4400, as force is imparted on the shaft 4410 in a z-axis direction, the shaft 4410 will travel along the z-axis, which in turn causes the rods 4816 and 4816 to translate along the z-axis (along their respective center axes). As the rods 4816 and 4818 (and magnets 4831 and 4833) move within the respective coils (4812 and 4814), each of the coils 4812 and 4816 generate a signal associated with a position of the magnets 4831 and 4833 within the respective coil 4812 and 4814. The microprocessor 4852 receives these signals from the coils 4812 and 4814. As described above, in some embodiments, each of the coils 4812 and 4814 generate a signal associated with a linear displacement of the shaft along the center axis $C_3$ of the shaft 4410 (e.g., along the z-axis). In some embodiments, the signals from the coils can include a first signal from the first coil 4812 having a first frequency, and a second signal from the second coil 4814 having a second frequency. The microprocessor 4852 is configured to execute instructions to determine from the first frequency and the second frequency a magnitude of a force on the shaft 4410 along the center axis $C_3$ of the shaft 4410.

As described above, the side-by-side positioning and the same configuration of the coils 4812 and 4814 (e.g., coil diameter, number of windings, type of wire, coil height, etc.) provides a fully redundant inductive force sensor that can also fit within the constrained space of the mechanical structure 4700, and can measure force linearly within a suitable travel range of the rods 4816 and 4818. In some embodiment the linear range is within ±2 mm (0.080 inches) inside the coils 4812 and 4814. This is achieved, in part, by coupling the rods 4816 and 4818 within the coils 4812 and 4814, respectively, such that a clearance gap between an outer surface of the rods 4816 and 4818 and an inner surface of the coils 4812 and 4814 is of a suitable amount. In some embodiments, the clearance gap can be about 1.33 mm (0.050 inches) as described above. Other parameters that contribute to the ability to achieve a redundant force sensor configuration are the coil length (or height), width, and thickness of the coil wire and the dimensions of the rods such that an optimal size of the coils can be achieved and the linear range of the rods within the coils can be increased. In addition to providing a longer linear range of travel of the rods, positioning the two coils 4812 and 4814 in an adjacent configuration allows for reducing the height H of the coils 4812 and 4814 and maintaining an inductance in the range of 0-2 µH. The coils 4812 and 4814 have identical dimensions (e.g., height, wire diameter, width, material) and are wound separately, and are coupled to the coil mounting bracket such that they are disposed at the same height H within the medial device 4400. In this manner, each coil 4812 and 4814 provides a separate signal, which can be tracked and compared simultaneously. Because the coils 4812 and 4814 having identical dimensional and material parameters, the coils 4812 and 4814 can have a similar temperature response to their environment. Thus, by determining the displacement based on two signals, the effect of temperature can be subtracted out.

FIGS. 7A-32 are various views of a medical device 5400 and its components, according to an embodiment. In some embodiments, the medical device 5400 or any of the components therein are optionally parts of a surgical system that performs surgical procedures, and which can include a manipulator unit, a series of kinematic linkages, a series of cannulas, or the like. The medical device 5400 (and any of the instruments described herein) can be used in any suitable surgical system, such as the MIRS system 1000 shown and described above. The medical device 5400 includes a mechanical structure 5700 at a proximal end portion of the medical device 5400, an outer shaft 5910, a shaft 5410 (which functions as an inner shaft in this embodiment), a force sensor unit 5800, and a distal end mechanism which includes a wrist assembly 5500, and an end effector 5460. Although not shown, the instrument 5400 can also include one or more connectors that couple the mechanical structure 5700 to the wrist assembly 5500 and end effector 5460, and function as tension members to actuate the end effector 5460. In some embodiments, the connectors can be a cable, a band or the like. The instrument 5400 is configured such that select movements of the connectors produces rotation of the wrist assembly 5500 (i.e., pitch rotation) about a first axis of rotation $A_1$ (see FIG. 8) (which functions as a pitch axis; the term pitch is arbitrary), yaw rotation of the end effector 5460 about a second axis of rotation $A_2$ (see FIG. 8) (which functions as the yaw axis; the term yaw is arbitrary), a cutting rotation of the tool members of the end effector 5460 about the second axis of rotation $A_2$, or any combination of these movements. Changing the pitch or yaw of the instrument 5400 can be performed by manipulating the connectors in a similar manner as described, for example, in U.S. Pat. No. 8,821,480 B2 (filed Jul. 16, 2008), entitled "Four-Cable Wrist with Solid Surface Cable Channels," which is incorporated herein by reference in its entirety. Thus, the specific movement of each of the connectors to accomplish the desired motion is not described below.

The shaft 5410 includes a proximal end 5411 that is coupled to the mechanical structure 5700, and a distal end 5412 (see FIG. 8) that is coupled to a beam 5810 via an anchor 5925. The beam 5810 can include or have coupled thereto one or more strain sensors (not shown) to measure forces imparted on the surgical instrument in the x and y directions during a surgical procedure. Thus, the beam 5810 can be a part of a force sensor unit similar those shown and described in co-pending U.S. Provisional Patent Application No. 63/026,321 (filed May 18, 2020), entitled "Devices and Methods for Stress/Strain Isolation on a Force Sensor Unit," the disclosure of which is incorporated herein by reference in its entirety. Although a beam 5810 with x-y sensors is shown and described in this embodiment, in other embodiments, a beam 5810 and x-y sensors may not be included. The proximal end of the shaft 5410 is coupled to the mechanical structure 5700 in a manner that allows movement of the shaft 5410 along a center axis $C_3$ of the shaft 5410 (shown in FIG. 8) relative to the mechanical structure 5700. More specifically, in this embodiment, the shaft 5410 extends through an opening 5764 (see FIG. 9) in a base 5770 of the mechanical structure 5700 and is coupled to a first link 5821 of a linkage 5850 that allows for the shaft 5410 to translate in the z-axis direction and also rotate, as described in more detail below. Allowing the shaft 5410 to float (i.e., remain in an energy-neutral but displaceable position) with reference to mechanical structure 5700 in the z direction facilitates measurement of forces along the z-axis, as described herein. The shaft 5410 also defines a lumen (not shown) and/or multiple passageways through which the connectors and other components (e.g., electrical wires, ground wires, or the like) can be routed from the mechanical structure 5700 to the wrist assembly 5500. The anchor 5925 can be received at least partially within the lumen of the shaft 5410 and can be fixedly coupled to the shaft 5410 via an adhesive bond, a weld, or any other permanent coupling mechanism (i.e., a coupling mechanism that is not intended to be removed during normal use).

The outer shaft 5910 can be any suitable elongated shaft that can be disposed over the shaft 5410 and includes a proximal end 5911 that can be coupled to the mechanical structure 5700 and a distal end 5912. The outer shaft 5910 defines a lumen between the proximal end 5911 and the distal end 5912. The shaft 5410 extends within the lumen of the outer shaft 5910 and can move relative to the outer shaft 5910. For example, the shaft 5410 can rotate relative to the outer shaft 5910 and/or can translate longitudinally in a direction parallel to the center axis $C_3$ of the shaft 5410 (i.e., the z direction). In this embodiment, the proximal end 5911 of the outer shaft 5910 is coupled to a locking handle 5919 that is fixedly coupled to the mechanical structure 5700, as shown in FIG. 7B. The locking handle 5919 can be used to move the outer shaft 5410 relative to the shaft 5410 and lock the outer shaft 5910 in a position along the z-axis direction relative to the shaft 5410. In this manner, the outer shaft 5910 can be retracted (i.e., moved proximally) relative to the shaft 5410 to expose the beam 5810 to facilitate cleaning of the beam 5810 or any sensors coupled thereto. In some embodiments, the locking handle 5919 can be constructed the same as or similar to, and function the same as or similar to the outer shaft mounting tube assembly 970 shown and described in U.S. Provisional Patent Application No. 62/916,716 (filed Oct. 17, 2019), entitled "Surgical Tool with Nested Shafts," the disclosure of which is incorporated herein by reference in its entirety. In other embodiments, the outer shaft 5910 or portions thereof can move relative to the mechanical structure 5700 (e.g., the outer shaft 5910 can be a telescoping shaft).

Figure 8:
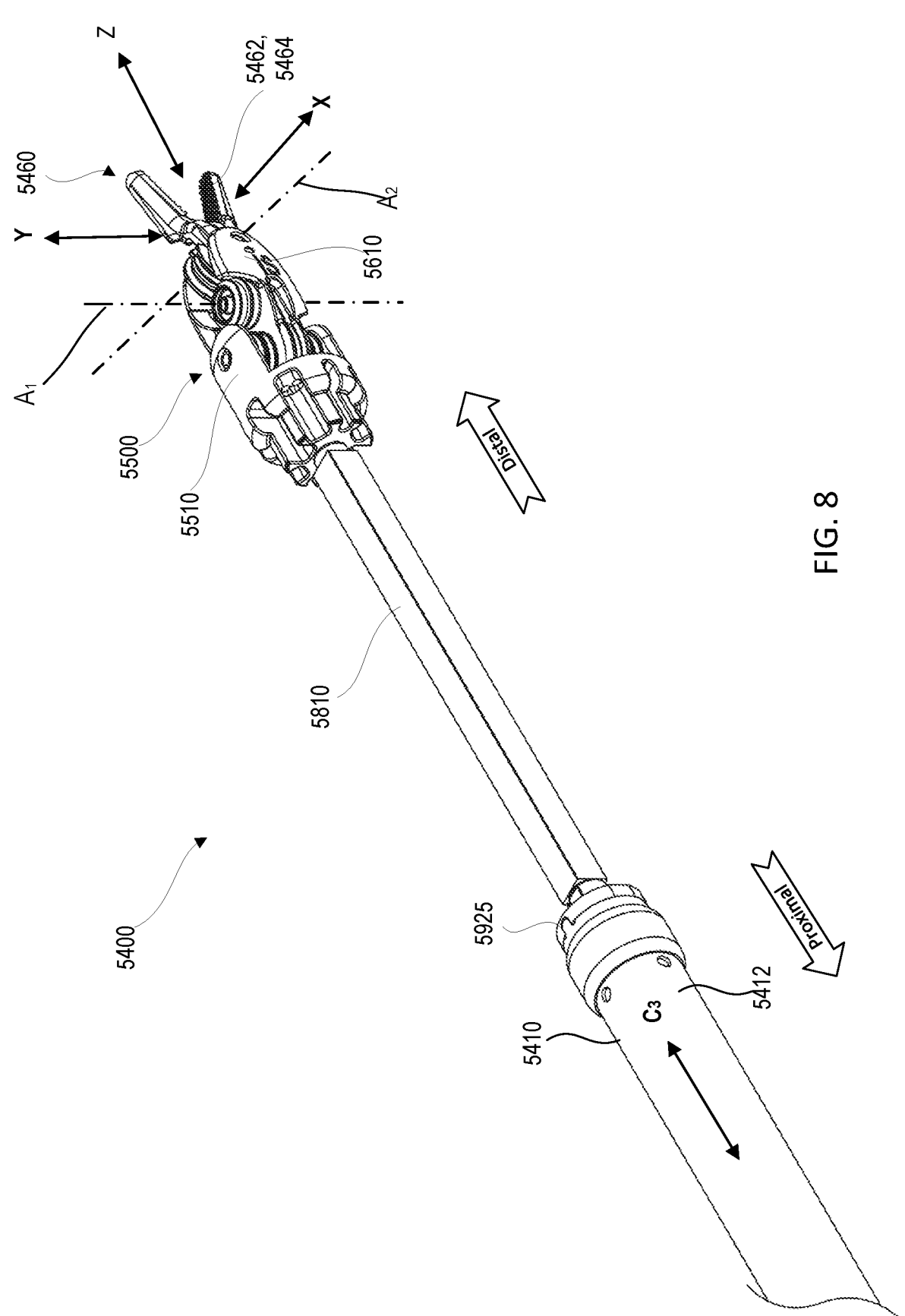
FIG. 8 is an enlarged perspective view of a distal end portion of the medical device of FIG. 7A.
Figure 9:
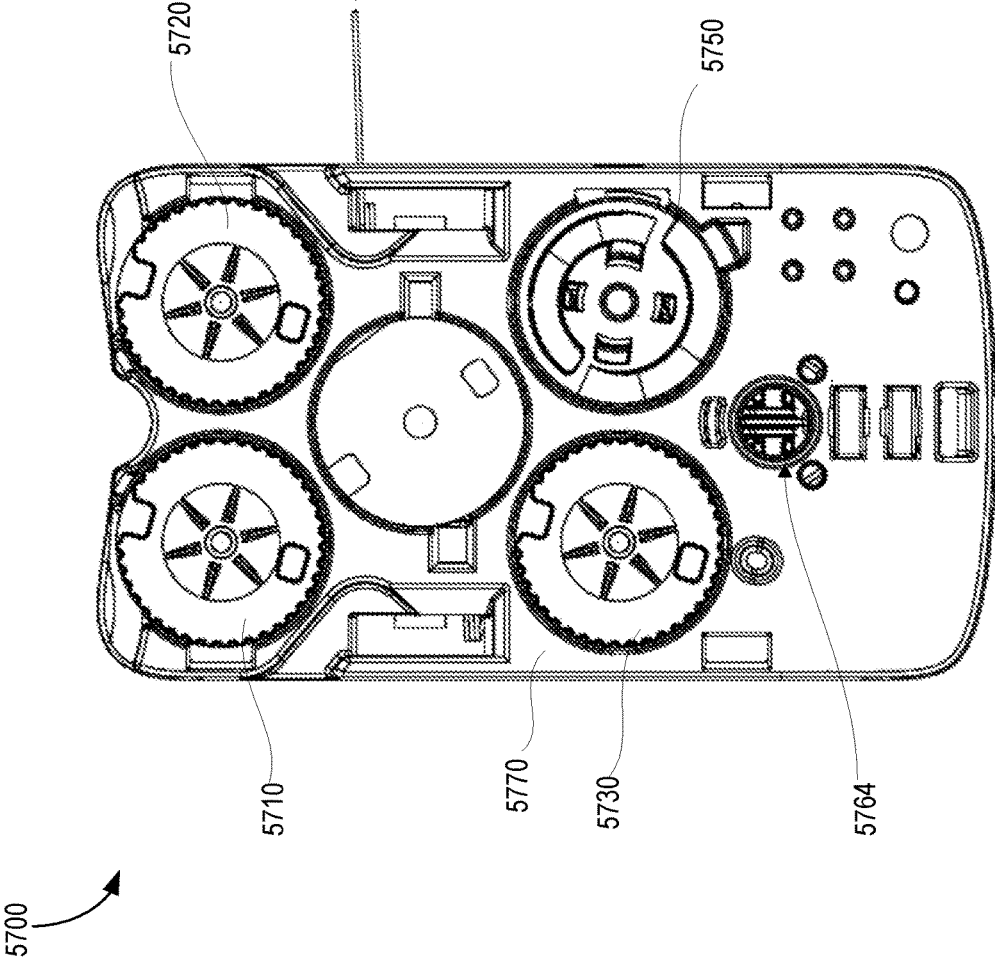
FIG. 9 is a bottom view of the mechanical structure of the medical device of FIG. 7A.
Figure 10:
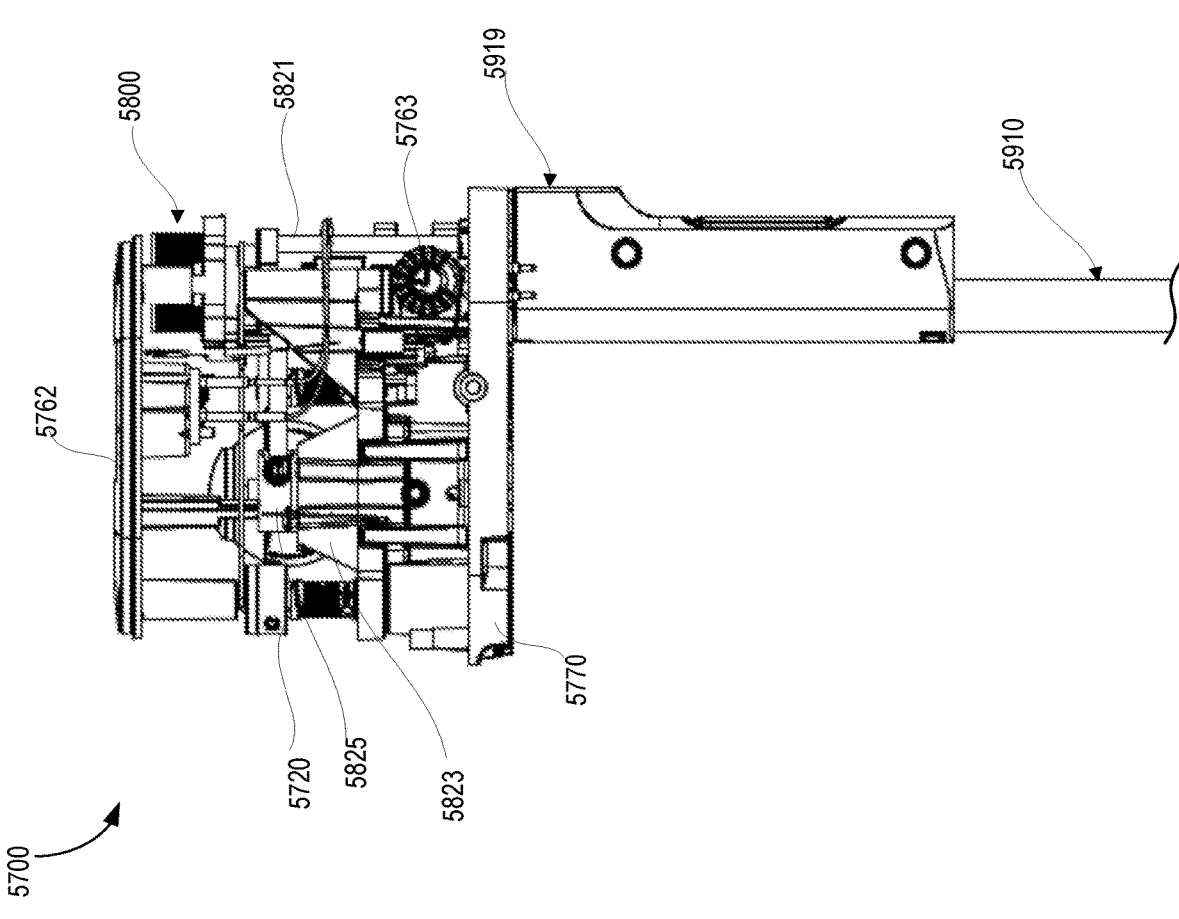
FIG. 10 is a side view of a proximal portion of the medical device of FIG. 7B.
Figure 11:
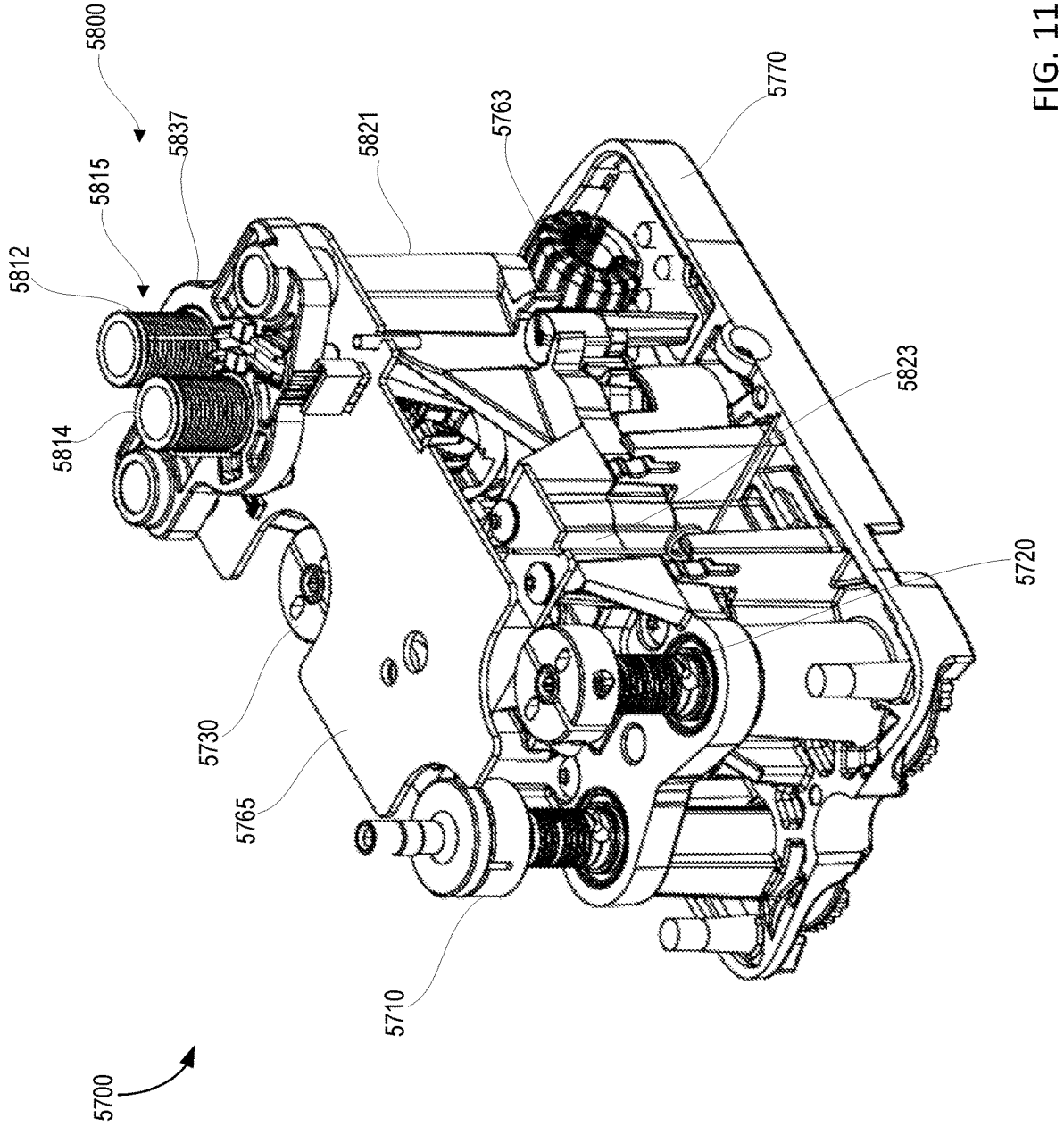
FIG. 11 is a perspective view of the mechanical structure of the medical device of FIG. 7A with select components removed for illustration purposes.

Referring to FIG. 8, the wrist assembly 5500 includes a proximal first link 5510 and a distal second link 5610. The first link 5510 includes a distal portion that is coupled to a proximal portion of the second ink 5610 at a joint such that the second link 5610 can rotate relative to the first link 5510 about a first axis of rotation $A_1$ (which functions as the pitch axis, the term pitch is arbitrary). The proximal first link 5510 includes a proximal portion that is coupled to the beam 5810 as described in more detail herein.

A distal end of the distal second link 5610 is coupled to the end effector 5460 such that the end effector 5460 can rotate about a second axis of rotation $A_2$ (see FIG. 8) (which functions as the yaw axis). The end effector 5460 can include at least one tool member 5462 having a contact portion 5464 configured to engage or manipulate a target tissue during a surgical procedure. For example, in some embodiments, the contact portion 5464 can include an engagement surface that functions as a gripper, cutter, tissue manipulator, or the like. In other embodiments, the contact portion 5464 can be an energized tool member that is used for cauterization or electrosurgical procedures. The end effector 5460 is operatively coupled to the mechanical structure 5700 such that the tool member 5462 rotates relative to shaft 5410 about the first axis of rotation $A_1$. In this manner, the contact portion 5464 of the tool member 5462 can be actuated to engage or manipulate a target tissue during a surgical procedure. The tool member 5462 (or any of the tool members described herein) can be any suitable medical tool member. Moreover, although only one tool member 5462 is identified, as shown, the instrument 5400 can include two tool members that cooperatively perform gripping or shearing functions. In other embodiments, an end effector can include more than two tool members.

The mechanical structure 5700 includes components to produce movement of the connectors (not shown) to produce the desired movement (pitch, yaw, or grip) at the wrist assembly 5500. Specifically, the mechanical structure 5700 includes components and controls to move some of the connectors in a proximal direction (i.e., to pull in certain connectors) while simultaneously allowing the distal movement (i.e., releasing; paying out) of other of the connectors in equal lengths. In this manner, the mechanical structure 5700 can maintain the desired tension within the connectors, and in some embodiments, can ensure that the lengths of the connectors are conserved (i.e., moved in equal amounts) during the entire range of motion of the wrist assembly 5500. In other embodiments, however, conservation of the lengths of the connectors is not required.

In some embodiments, the mechanical structure 5700 can include one or more mechanisms that produce translation (linear motion) of a portion of the connectors. Such a mechanisms can include, for example, a gimbal, a lever, or any other suitable mechanism to directly pull (or release) an end portion of any of the connectors. For example, in some embodiments, the mechanical structure 5700 can include any of the mechanical structures (referred to as backend assemblies or actuators) or components described in U.S. Patent Application Pub. No. US 20157/0047454 $A_1$ (filed Aug. 15, 2014), entitled "Lever Actuated Gimbal Plate," or U.S. Pat. No. 6,817,974 B2 (filed Jun. 28, 2001), entitled "Surgical Tool Having Positively Positionable Tendon-Actuated Multi-Disk Wrist Joint," each of which is incorporated herein by reference in its entirety.

As shown in FIGS. 9-12, the mechanical structure 5700 includes three capstans 5720, 5730, and 5740 (which function as actuator input pieces), and a roll driver 5750, which each function as operation input pieces. The capstans 5720, 5730, 5740 are motor-driven rollers that rotate (wind) a portion of the connectors (not shown) to produce the desired connector movement, and therefore the desired movement of the wrist assembly 5500 and end effector 5460. As described below, the roll driver 5750 is a motor-driven member that produces rotation (referred to as "roll") of the shaft 5410. In some embodiments, the mechanical structure 5700 can be constructed the same as or similar to the mechanical structures (referred to as backend assemblies or actuators) or components therein described in U.S. Pat. No. 9,204,923 B2 (filed Jul. 16, 2008), entitled "Medical Instrument Electronically Energized Using Drive Cables," which is incorporated herein by reference in its entirety. The mechanical structure 5700 also includes an instrument support structure that includes the base 5770 and a top plate 5762, a circuit board 5765 and a common-mode choke 5763 (discussed in more detail below with reference to FIG. 33). In other embodiments, various support structures optionally may be used, such as a chassis, a frame, a bed, a unitized surrounding outer body of the mechanical structure, and the like.

Figure 13:
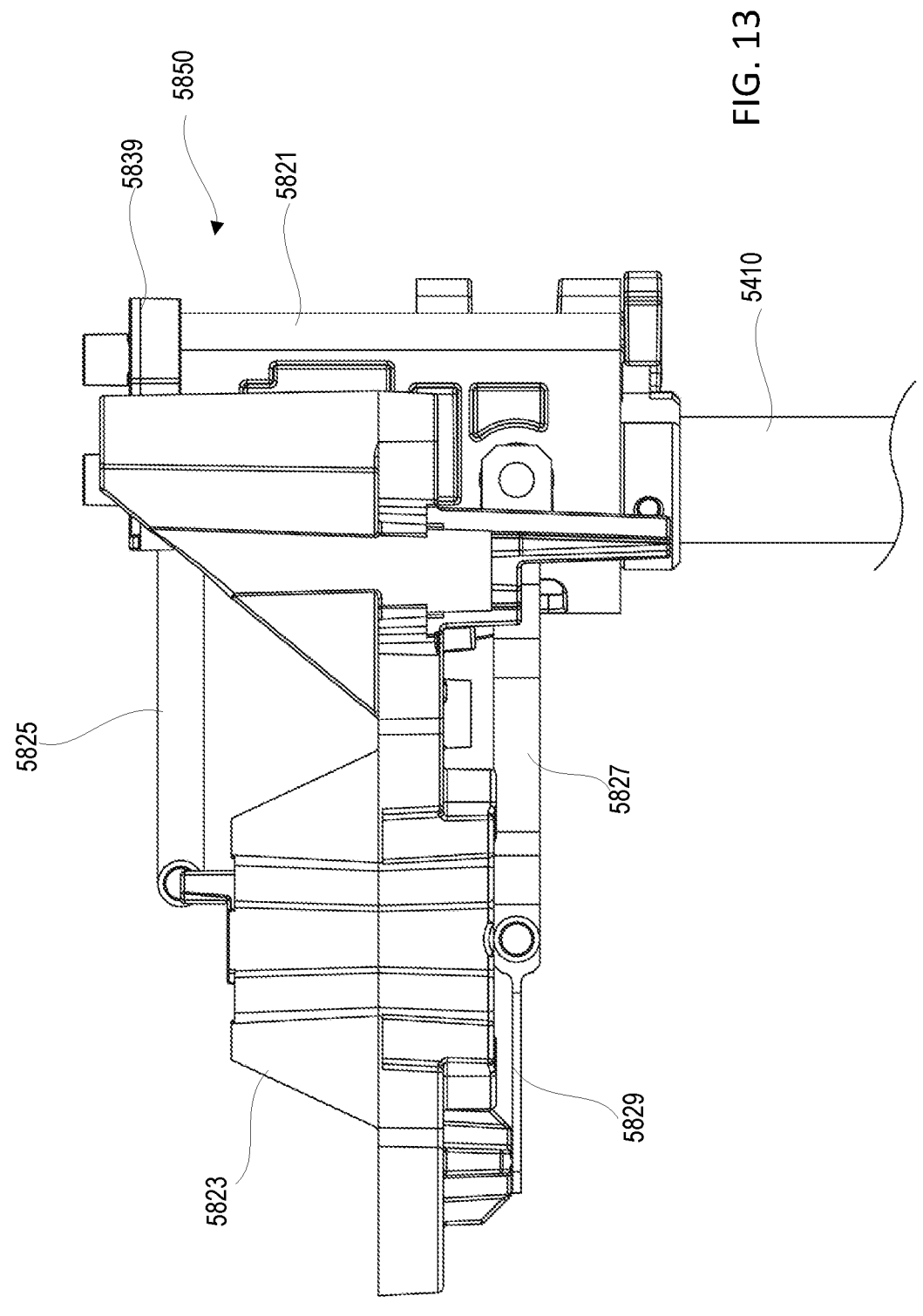
FIG. 13 is a side view of a linkage and shaft of the medical device of FIG. 7A with select components removed for illustration purposes.
Figure 14:
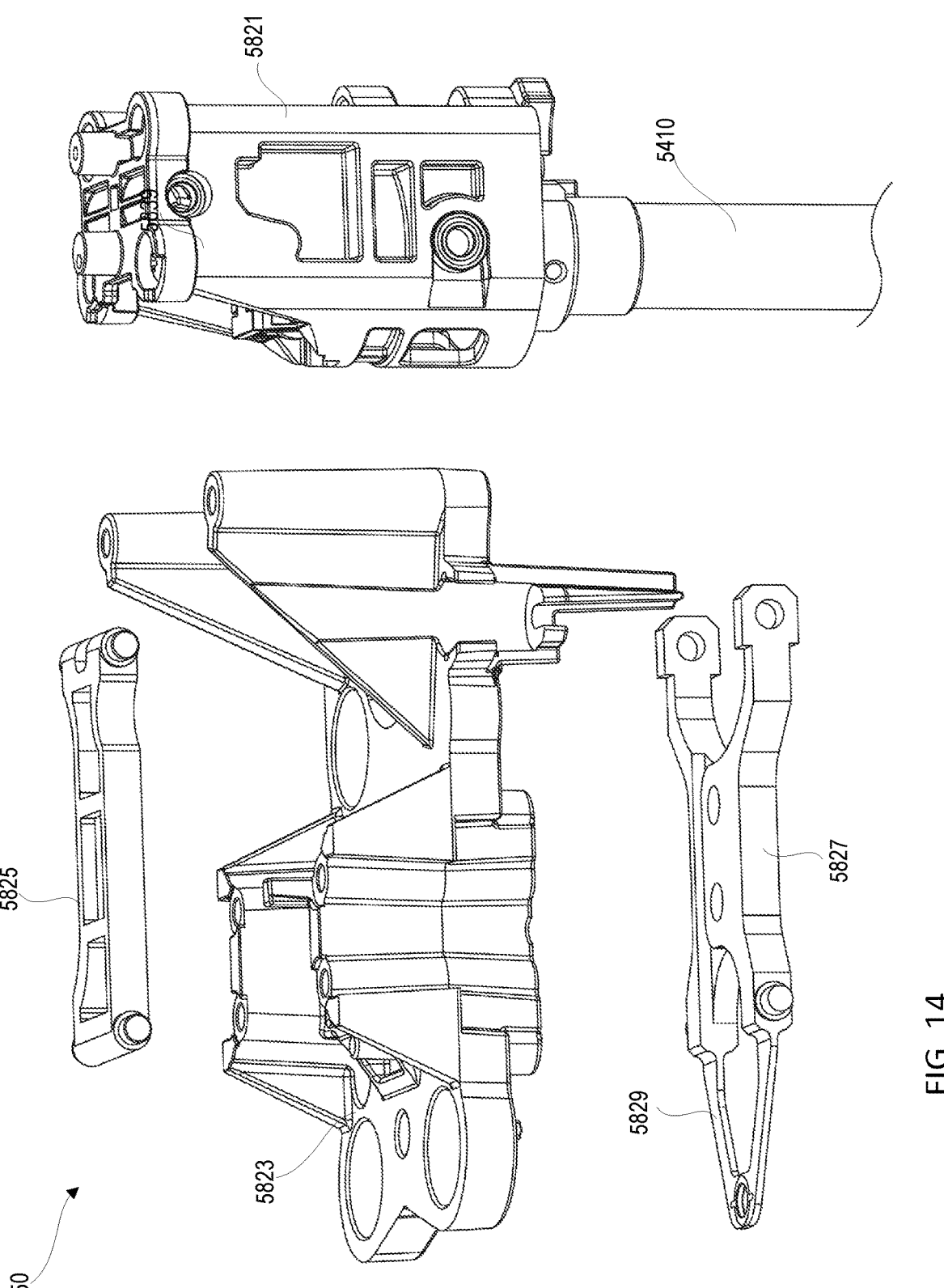
FIG. 14 is a partially exploded view of the linkage and shaft of FIG. 13.

The mechanical structure 5700 surrounds (or is coupled to) the force sensor unit 5800, which includes a coil assembly 5815, a linkage 5850 (which functions as a movable four-bar linkage) and a microprocessor (see example microprocessor in FIG. 33). The linkage 5850 includes four links coupled to the mechanical structure 5700. More specifically, as best shown in FIGS. 13 and 14, the linkage 5850 includes a first link 5821 (which functions to support the shaft and allow it to roll; a "roll carrier") coupled to the shaft 5410, a second link 5827 coupled to the first link 5821 and coupled to a support mount 5841 (see, e.g., FIG. 15). A bracket 5839 is coupled to an end of the first link 5821 and is used to couple the rods of the coil assembly 5815 to the first link 5821, as described in more detail below. The second link 5827 includes a spring element 5829 that is coupled to or supported by the support mount 5841, as shown in FIG. 15. The linkage 5850 also includes a third link 5825 coupled to the first link 5821 and a fourth link 5823 coupled to the second link 5827 and the third link 5825. The fourth link 5823 is stationary and acts as a local mechanical ground for the other three links, which move when the shaft 5410 is moved along its axis C-A. The four links of the linkage 5850 can maintain connector tension within the medical device 5400, and provide for linear movement of the shaft 5410 when forces are applied axially at the distal end of the medical device 5400. The linkage 5850 can also constrain the movement in the z-axis and isolates forces in the z-axis.

The shaft 5410 is coupled to the mechanical structure 5700 via the linkage 5850 such that the amount of travel of the shaft 5410 relative to the mechanical structure 5700 can be correlated to the magnitude of the axial force imparted to the end effector 5460. In this manner, measuring the distance through which the shaft 5410 moves relative to the mechanical structure 5700 can be used to determine the axial force (e.g., the force in the z direction) applied the distal end of the shaft 5410 (e.g., at the end effector 5460). As described herein, the linkage 5850 isolates the axial movement of the shaft 5410 (i.e., constrains the shaft movement such that the measured movement is caused only by the axial force, and not the transverse forces along the x- and y-axes), limits frictional force opposing movement of the shaft 5410, and provides suitable structure for the coaxially arranged coils as described below.

More specifically, the shaft 5410 is coupled to the first link 5821 of the linkage 5850 via a roll drive receiver 5738 (see, e.g., FIGS. 21-22), such that when the shaft 5410 moves along the z-axis direction, the first link 5821 moves along the z-axis direction with the shaft 5410. Said another way, the shaft 5410 is coupled to the first link 5821 in a manner that restricts movement of the shaft 5410 relative to the first link 5821 along the z-axis. The roll drive receiver 5738, however, allows for the shaft 5410 to also rotate relative to the first link 5821 (e.g., the first link 5821 does not rotate when the shaft 5410 rotates about the z-axis). The roll drive receiver 5738 can be actuated by a cable (band, cord or other suitable connector (not shown)) coupled to a roll driver 5750 and wound about a portion of the roll drive receiver 5738. This arrangement allows the shaft 5410 to move about the z-axis relative to the mechanical structure 5700 (which allows measurement of the axial force) while also allowing the shaft 5410 to be rotated about the z-axis.

The spring 5829 of the second link 5827 can be formed with a material that is more flexible than a remaining portion of the second link 5827, thereby producing a spring with a desired stiffness. The amount of travel of the shaft 5410 in the z-axis direction depends in part on the stiffness of the spring 5829 of the second link 5827. For example, if the spring 5829 is very stiff, the shaft 5410 will only move a short distance when an axial force is applied to the end effector 5460. Conversely, if the spring 5829 is less stiff, the same axial force will produce greater movement of the shaft 5410. Thus, the spring 5829 can be selected to have the desired stiffness such that the total travel of the shaft 5410 over the expected range of axial forces to be applied will be within the dynamic range of the force sensor unit 5800.

Although the spring 5829 is shown as being a leaf spring, in other embodiments the linkage 5850 can include any suitable type of spring (e.g., a coil spring or a torsion spring).

FIG. 18 illustrates a position of the second link 5827 when the second link 5827 and shaft 5410 are in a neutral position (e.g., unactuated). During use of the medical device 5400 when the shaft is moved along the z-axis direction, the first link 5821 will move with the shaft 5410, and the second link 5827, being coupled to the first link 5821, will pivot about a pivot joint 5742. For example, FIG. 19 illustrates the shaft 5410 translated proximally in the z-axis direction, and FIG. 20 illustrates the shaft 5410 translated distally in the z-axis direction (the first link 5821 is removed for illustration purposes). As shown in FIG. 19, the second link 5827 is angled downward, and the pivot joint 5742 is at a distance D1 from a reference line L. In this FIG. 19 configuration (proximal movement of the shaft 5410), the shaft 5410 is exposed to a first force F1. As shown in FIG. 20, the second link 5827 is angled upward, and the pivot joint 5742 is at a distance D2 from the reference line L, which is less than the distance D1. In this FIG. 20 configuration (distal movement of the shaft 5410), the shaft is exposed to a second force F2, which is less than the first force F1. By measuring the distances D1 and D2, the magnitude of the first force F1 and the second force F2 can be determined.

As shown in FIGS. 26-29, the coil assembly 5815 includes a first coil 5812, a second coil 5814, a first rod 5816, a second rod 5818, a first magnet 5831, a second magnet 5833, and a mounting bracket 5837. The mounting bracket 5837 is secured within the mechanical structure 5700 and is electrically coupled to the circuit board 5765 via wiring 5835. The first coil 5812 and the second coil 5814 are each mounted within the mounting bracket 5837 and positioned side-by-side to each other. The first coil 5812 and the second coil 5814 are each inductive coils and are each wound around a cylinder of an electrically nonconductive material, such as, for example, PEEK. The first coil 5812 and the second coil 5814 are made with identical characteristics, such as coil length, coil width, and thickness of the coil wire.

As shown in FIG. 25, the first rod 5816 is coupled to the bracket 5839 and is movably located at least partially within the first coil 5812. Similarly, the second rod 5818 is coupled to the bracket 5839 and is movably located at least partially within the second coil 5814. More specifically, as shown in FIGS. 26-32, the first rod 5816 includes a support portion 5817 and the second rod 5818 includes a support portion 5819 each of which is coupled to the first link 5821 via the bracket 5839. For example, the support portion 5817 and the support portion 5819 of the rods 5816 and 5818 each extend through an opening in the mounting bracket 5837 and are coupled to the bracket 5839, thus coupling the rods 5816 and 5818 to the first link 5821 and to the shaft 5410. For example, in some embodiments, the support portions 5817 and 5819 can be press fit to the bracket 5839. In alternative embodiments, the support portions 5817 and 5819 can be coupled to the bracket 5839 by another suitable coupling method, such as an adhesive or welding.

Figure 12:
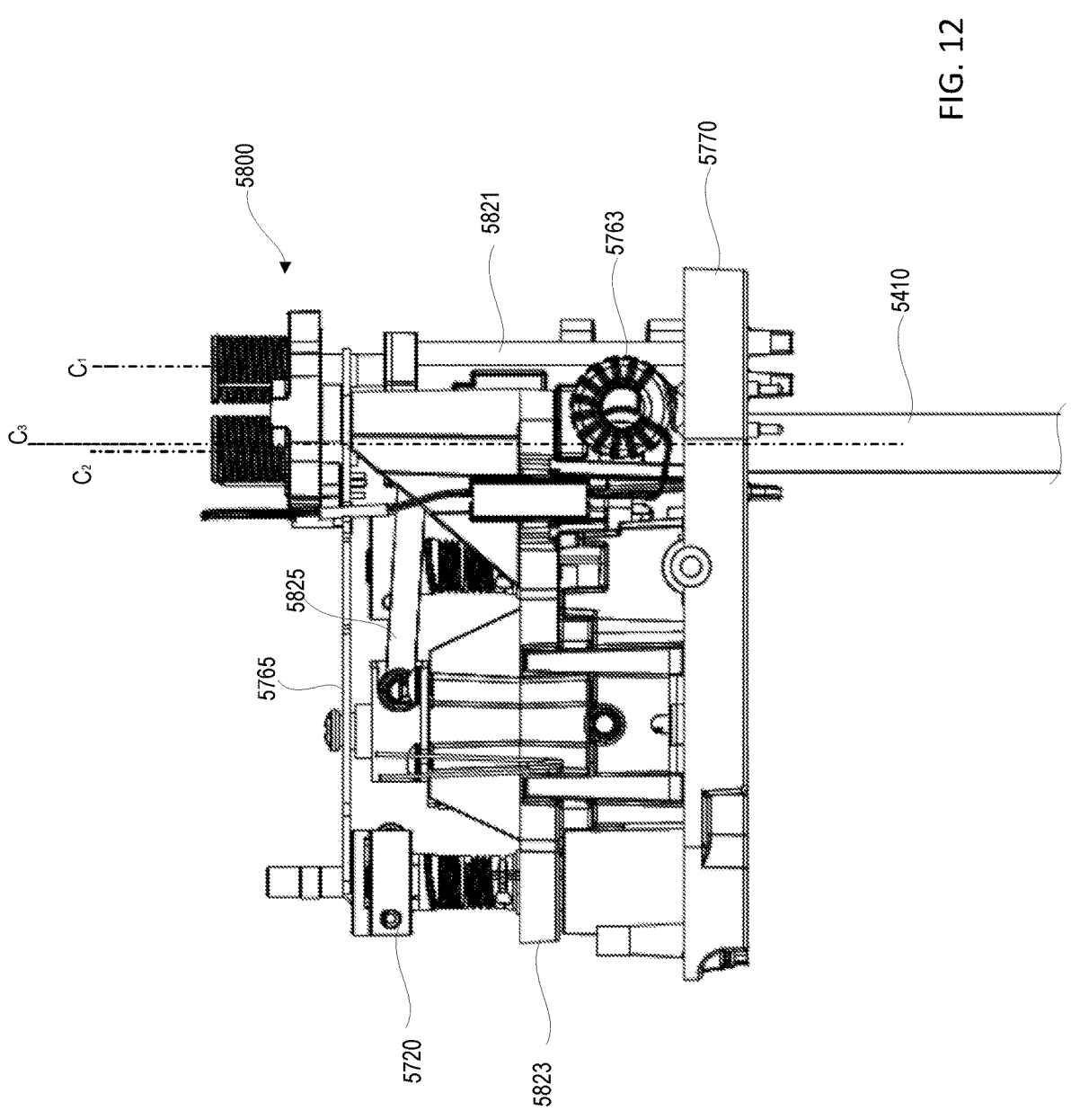
FIG. 12 is a side view of the mechanical structure and shaft of the medical device of FIG. 7A with select components removed for illustration purposes.

Thus, because the first link 5821 is fixedly coupled to the shaft 5410 in the z axis, the first rod 5816 and the second rod 5818 are each fixedly coupled to the shaft 5410 and can move in the z-axis direction with the shaft 5410 and first link 5821. In some embodiments, the coil assembly 5815 is coupled to the mechanical structure 5700 such that a center axis $C_3$ of the shaft 5410 is between a center axis $C_1$ of the first rod 5816 and a center axis $C_2$ of the second rod 5818 as shown in FIG. 12. In some embodiments, the center axis $C_3$ of the shaft 5410 is parallel to the center axes $C_1$ and $C_2$ of the first rod 5816 and the second rod 5816, respectively. In some embodiments, the center axis $C_3$ of the shaft 5410 is centered between the center axis $C_2$ of the first rod 5816 and the center axis $C_2$ of the second rod 5818.

As shown in FIG. 29, the first rod 5816 includes a core 5836, and the second rod 5818 includes a core 5838. The first magnet 5831 is coupled to the core 5836 of the first rod 5816, and the second magnet 5833 is coupled to the core 5838 of the second rod 5818, such that the first magnet 5831 moves with the first rod 5816, and the second magnet 5833 moves with the second rod 5818. For example, as described above, the first and second rods 5816 and 5818 are coupled to the shaft 5410, such that when the shaft 5410 moves axially due to forces imparted on a distal end of the medical device 5400 (e.g., at the end effector 5460), the rods 5816 and 5818 move with the shaft 5410 within the coils 5812 and 5814, respectively. As the rods 5816 and 5818 and magnets 5831 and 5833 move within the inductive coils 5812 and 5814, this movement causes a change in inductance at the coils, which can be used to measure changes in position of the shaft 5410, which can be converted to z-axis force measurements. As described above for previous embodiments, the cores 5836 and 5838 can each be, for example, a glass core, a stainless steel core, or a core formed with another suitable material. The magnets 5831 and 5833 can each be, for example, a ferrite bead, an EMI suppression bead, a nickel-zinc bead, or any other suitable material or any component or material coupled to the respective cores that can be used to provide a signal indicative of the position of the cores within the respective coils 5812 and 5814 as the rods 5816 and 5818 and cores move within the respective coils 5812 and 5814.

The first rod 5816 (with magnet 5831) is positioned substantially centered within the first coil 5812 with a clearance gap G (see the bottom view of the coil assembly in FIG. 30) between an outer surface of the first rod 5816 and an inner surface of the first coil 5812. Similarly, the second rod 5818 (with magnet 5833) is positioned substantially centered within the second coil 5814 with a clearance gap G between an outer surface of the second rod 5818 and an inner surface of the second coil 5814. In some embodiments, the clearance gap G is about 1.33 mm (0.050 inches). As described above, this gap allows for tolerance errors in the placement of the rods and reduces the likelihood of frictional losses between the rods and the coils. This is desirable because inner friction between the rods and the coil can lead to false force readings in the z-axis direction.

During use of the medical device 5400, as force is imparted on the shaft 5410 in a z direction, the shaft 5410 will travel along the z-axis, which in turn causes the rods 5816 and 5816 to translate along the z-axis (along their respective center axes). As the rods 5816 and 5818 (and magnets 5831 and 5833) move within the respective coils, 5812 and 5814, each of the coils 5812 and 5816 generate a signal associated with a position of the magnets 5831 and 5833 within the respective coil 5812 and 5814. The microprocessor (which can be similar to the microprocessor 6852 shown in FIG. 33) receives these signals from the coils 5812 and 5814. As described above, each of the coils 5812 and 5814 generates a separate signal associated with a linear displacement of the shaft 5410 along the center axis $C_3$ of the shaft 5410 (e.g., along the z-axis). In some embodiments, the signals from the coils can include a first signal from the first coil 5812 having a first frequency, and a second signal from the second coil 5814 having a second frequency. The microprocessor is configured to execute instructions to determine from the first frequency and the second frequency a measure of a force on the shaft 5410 along the center axis $C_3$ of the shaft 5410.

As described above, the force sensor unit 5800 measures the change in the inductance within the coils due to the z-axis movement of the shaft (i.e., along the center axis $C_3$ of the shaft 4410), which is converted from position measurement to a force measurement. As described above, the second link 5827 with the spring 5829 and the coil assembly 5815 are mechanically grounded to the same rigid component of the mechanical structure 5700 (e.g., the base 5770) such that false force signals due to a difference in deflection in different grounding components can be avoided.

As also described above, the side-by-side (non-coaxial) positioning and the identical configuration of the coils 5812 and 5814 provides a fully redundant inductive force sensor that can measure force linearly within a suitable travel range of the rods 5816 and 5818. In some embodiments, the linear range of this arrangement can be between ±2 mm (0.080 inches) inside the coils 5812 and 5814. In other embodiments, this range can vary depending on, for example, the geometry of the coil and other properties such as the material of the wire and magnet. This is achieved, in part, by coupling the rods 5816 and 5818 within the coils 5812 and 5814, respectively, such that the gap G between an outer surface of the rods 5816 and 5818 and an inner surface of the coils 5812 and 5814 is a suitable amount. In some embodiments, the gap G is about 1.33 mm (0.050 inches), as described above. Other parameters that contribute to the ability to achieve a redundant force sensor configuration are the coil length (height), coil width, and thickness of the coil wire and the dimensions of the rods such that an optimal size of the coils can be achieved and the linear range of the rods within the coils can be increased. In addition to providing a longer linear range of travel of the rods, positioning the two coils 5812 and 5814 in an adjacent side-by-side configuration provides for the coils to fit within the constrained space of the mechanical structure 5700. For example, the coils 5812 and 5814 can have a reduced height H (see FIG. 26), while maintaining an inductance in the range of 0-2 μH. The coils 5812 and 5814 have identical dimensions (e.g., height, wire diameter, width, material) and are wound separately, and they are coupled to the mounting bracket 5837 such that they are positioned at the same height H with reference to the mounting bracket 5837 within the medial device 4400. Each coil 5812 and 5814 provides a separate signal, which can be tracked and compared simultaneously. Due to the coils 5812 and 5814 having identical dimensional and material parameters, the coils 5812 and 5814 have a similar temperature response to their environment. In some cases, a significant difference in the inductance of the coils can serve as a metric for drift.

FIG. 33 is a block diagram of a portion of an embodiment of a force sensor unit 6800 that can be implemented to measure axial force applied to an instrument shaft (e.g., shaft 5410). The force sensor unit 6800 can be implemented as an inductive z-axis force sensor unit as described above for any of the previous embodiments (including the force sensor unit 5800). As described above, an axial force on the instrument shaft results in an axial movement of the instrument shaft 6410, which can be detected by the force sensor unit 6800. The force sensor unit 6800 can include a coil assembly 6815 as described herein that includes a pair of coils 6812 and 6814 with a rod 6816 and rod 6818 movably positioned within the coils 6812 and 6814, respectively. The rod 6816 can have a magnet 6831 coupled thereto and the rod 6818 can have a magnet 6833 coupled thereto.

The coil 6812 can be coupled to a multi-channel frequency detection block 6865 by a capacitor C that can form an inductor/capacitor (LC) circuit with the coil 6812 with an inductance contribution based on the distance the rod 6816 and magnet 6831 move within the coil 6812. The coil 6814 can be coupled to the multi-channel frequency detection block 6865 by a capacitor C that can form an LC circuit with the coil 6814 with an inductance contribution based on the distance the rod 6818 and magnet 6833 move within the coil 6814. The LC circuits associated with the coils 6812 and 6814 can be implemented with different capacitances in implementations where such differences are taken into account.

The multi-channel frequency detection block 6865 can be implemented as a precision, dual inductance sensor that measures the inductance. With the capacitor C forming an LC circuit with the coil 6812 input to the multi-channel frequency detection block 6865, the multi-channel frequency detection block 6865 can output a first signal associated with a frequency of this circuit, for example a ratio of the frequency with a known reference frequency. With the capacitor C forming an LC circuit with the coil 6814 input to the multi-channel frequency detection 6865, the multi-channel frequency detection block 6865 can output a second signal associated with a frequency of this circuit, for example a ratio of the frequency with a known reference frequency. The multi-channel frequency detection block 6865 can output N digital signals to a microprocessor 6852. For two LC circuits, the multi-channel frequency detection block 6865 can output two digital signals to the microprocessor 6870.

The microprocessor 6852 can include or have access to an EEPROM 6872, or other storage device, that can include calibration values for implementation of the magnet 6831 within the coil 6812 and the magnet 6833 within the coil 6814. In a measurement of axial force on the instrument shaft, the calibration values can be accessed to determine a distance moved for each magnet 6831 and 6833 based on the frequencies received from the multi-channel frequency detection block 6865. The difference in frequencies can be stored in the EEPROM 6872 as a difference of inductance as a function of distances. This difference of distances can be correlated with a reference position and the difference in inductances. With a distance selected from a measured difference in inductances, the distance can be used with a spring constant stored in the EEPROM 6872, where the spring constant is a property of a spring (e.g., spring 5829 described above) by which the instrument shaft 6410 is coupled to a support structure on which the force sensor unit 6800 can be deployed.

The force sensor unit 6800 can include other optional components. For example, the microprocessor 6852 can include a Universal Asynchronous Receiver/Transmitter (UART) interface 6874 or other communication interface to transmit (TX) a digital output and receive (RX) a digital signal. The received signal can be used to update calibration values in the EEPROM 6872 of the microprocessor 6852. A common-mode choke 6763 (such as common-mode choke 5863) can be used to reduce interference with other electronic circuit boards of the support structure on which the force sensor unit 6800 is deployed. Optionally, the force sensor unit 6800 can include a magnetic structure 6862 between the common-mode choke 6763 and the microprocessor 6852. The magnetic structure 6862 can be inserted to help with electromagnetic interference (EMI) radiation reduction. The magnetic structure 6862 can be realized as a ferrite bead. Other magnetic material formats can be implemented for the magnetic structure 6862, as described above.

A machine-readable storage device may include any non-transitory mechanism for storing information in a form readable by a machine, for example, a computer or a microprocessor tasked to perform specific functions. For example, a machine-readable storage device may include read-only memory (ROM), random-access memory (RAM), magnetic disk storage media, optical storage media, flash-memory devices, and other storage devices and media. In various embodiments of a medical device with a force sensor unit described herein, a non-transitory machine-readable medium can comprise instructions, which when executed by one or more processors, can cause a system to perform operations that include without limitation: (i) receiving a first signal generated by a first coil associated with a position of a first magnet with reference to the first coil, (ii) receiving a second signal generated by a second coil associated with a position of a second magnet with reference to a second coil, and where the first signal from the first coil and the second signal from the second coil are associated with a linear displacement of the shaft along the center axis of the shaft. The force sensor unit can comprise a microprocessor coupled to receive the first and second signals. In various embodiments, a non-transitory machine-readable medium can comprise instructions, which when executed by one or more processors cause a system to perform operations comprising methods of performing functions associated with the various embodiments described herein.

While various embodiments have been described above, it should be understood that they have been presented by way of example only and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a telesurgical system that performs minimally invasive surgical procedures, and which can include a manipulator unit, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the components of a surgical instrument as described herein can be constructed from any material, such as medical grade stainless steel, nickel alloys, titanium alloys or the like. Further, any of the links, tool members, beams, shafts, connectors, cables, or other components described herein can be constructed from multiple pieces that are later joined together. For example, in some embodiments, a link can be constructed by joining together separately constructed components. In other embodiments however, any of the links, tool members, beams, shafts, connectors, cables, or components described herein can be monolithically constructed.

Although the instruments are generally shown as having an axis of rotation of the tool members (e.g., axis $A_2$) that is normal to an axis of rotation of the wrist member (e.g., axis $A_1$), in other embodiments any of the instruments described herein can include a tool member axis of rotation that is offset from the axis of rotation of the wrist assembly by any suitable angle. Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. A medical device, comprising:
a mechanical structure and a force sensor unit coupled to the mechanical structure;
a shaft coupled to the mechanical structure, the shaft having a proximal end and a distal end;
wherein the force sensor unit comprises a mounting bracket, a first rod, a second rod, a first magnet, a second magnet, a first coil coupled to the mounting bracket, and a second coil coupled to the mounting bracket, the mounting bracket disposed proximal of the proximal end of the shaft;
wherein the first rod comprises a distal portion and a proximal portion, and a center axis of the first rod is defined between the proximal portion and the distal portion of the first rod;
wherein the second rod comprises a distal portion and a proximal portion, a center axis of the second rod is defined between the proximal portion and the distal portion of the second rod, and the center axis of the second rod is noncoaxial with the center axis of the first rod;
wherein the first magnet is coupled to the first rod, and the second magnet is coupled to the second rod; and
wherein the first magnet translates within the first coil along the center axis of the first rod, and the second magnet translates within the second coil along the center axis of the second rod.

2. The medical device of claim 1, wherein:
the shaft is operably coupled to the first rod and the second rod such that translational movement of the shaft relative to the mechanical structure moves the first rod along the center axis of the first rod and moves the second rod along the center axis of the second rod.

3. The medical device of claim 2, wherein:
a center axis of the shaft is defined between the proximal end and the distal end of the shaft;
a first signal generated by the first coil is associated with a position of the first magnet with reference to the first coil, and a second signal generated by the second coil is associated with a position of the second magnet with reference to the second coil; and
the first signal from the first coil and the second signal from the second coil are associated with a linear displacement of the shaft along the center axis of the shaft.

4. The medical device of claim 3, wherein:
the linear displacement of the shaft is in proportion to a force imparted to the shaft in a direction along the center axis of the shaft.

5. The medical device of claim 4, wherein:
a center axis of the shaft is defined between the proximal end and the distal end of the shaft; and
the first coil and the second coil are secured to the mounting bracket such that the center axis of the shaft is centered between the center axis of the first rod and the center axis of the second rod.

6. The medical device of claim 4, wherein:
the center axis of the first rod and the center axis of the second rod are parallel to the center axis of the shaft.

7. The medical device of claim 4, wherein:
a center axis of the shaft is defined between the proximal end and the distal end of the shaft;
the first signal has a first frequency, and the second signal has a second frequency; and
a microprocessor is configured to execute instructions to determine from the first frequency and the second frequency a measure of a force on the shaft along the center axis of the shaft.

8. The medical device of claim 2, wherein:
a center axis of the shaft is defined between the proximal end and the distal end of the shaft; and
the first coil and the second coil are secured to the mounting bracket such that the center axis of the shaft is centered between the center axis of the first rod and the center axis of the second rod.

9. The medical device of claim 2, wherein:
the first coil has a first height, the second coil has a second height, and the first height is equal to the second height.

10. The medical device of claim 2, wherein:
a center axis of the shaft is defined between the proximal end and the distal end of the shaft;
the medical device further comprises a linkage coupled to the shaft and to the mechanical structure;
the linkage comprises a spring; and
the spring is configured to be displaced in proportion to a force imparted to the shaft in a direction along the center axis of the shaft.

11. The medical device of claim 10, wherein:
a center axis of the shaft is defined between the proximal end and the distal end of the shaft;
a first signal generated by the first coil is associated with a position of the first magnet with reference to the first coil, and a second signal generated by the second coil is associated with a position of the second magnet with reference to the second coil;
the first signal has a first frequency, and the second signal has a second frequency; and
a microprocessor is configured to execute instructions to determine from the first frequency and the second frequency a measure of a force on the shaft along the center axis of the shaft.

12. The medical device of claim 2, wherein:
a first signal generated by the first coil is associated with a position of the first magnet with reference to the first coil, and a second signal generated by the second coil is associated with a position of the second magnet with reference to the second coil; and
the force sensor unit comprises a microprocessor coupled to receive the first and second signals.

13. The medical device of claim 2, wherein:
the shaft comprises a proximal end and a distal end;
a center axis of the shaft is defined between the proximal end and the distal end of the shaft;
a first signal generated by the first coil is associated with a position of the first magnet with reference to the first coil, and a second signal generated by the second coil is associated with a position of the second magnet with reference to the second coil;

the first signal has a first frequency, and the second signal has a second frequency; and a microprocessor is configured to execute instructions to determine from the first frequency and the second frequency a measure of a force on the shaft along the center axis of the shaft.

14. The medical device of claim 1, wherein:

a center axis of the shaft is defined between the proximal end and the distal end of the shaft; and the shaft is operably coupled to the first rod and the second rod such that the shaft is rotatable about the center axis of the shaft without moving the first rod or the second rod.

15. The medical device of claim 1, wherein:

the first coil has a first height, the second coil has a second height, and the first height is equal to the second height.

16. The medical device of claim 1, wherein:

a first signal generated by the first coil is associated with a position of the first magnet with reference to the first coil, and a second signal generated by the second coil is associated with a position of the second magnet with reference to the second coil; and the force sensor unit comprises a microprocessor coupled to receive the first and second signals.

17. The medical device of claim 1, wherein:

a first signal generated by the first coil is associated with a position of the first magnet with reference to the first coil, and a second signal generated by the second coil is associated with a position of the second magnet with reference to the second coil;

the first signal has a first frequency, and the second signal has a second frequency; and a microprocessor is configured to execute instructions to determine from the first frequency and the second frequency a measure of a force on the shaft along the center axis of the shaft.

18. The medical device of claim 1, wherein:

the medical device further comprises a link coupled to the shaft;

the first rod and the second rod are coupled to the link; and the link comprises a roll drive receiver in which the shaft is rotatable relative to the link without moving the first rod or the second rod.

19. The medical device of claim 18, wherein:

a center axis of the shaft is defined between the proximal end and the distal end of the shaft;

a first signal generated by the first coil is associated with a position of the first magnet with reference to the first coil, and a second signal generated by the second coil is associated with a position of the second magnet with reference to the second coil; and the first signal from the first coil and the second signal from the second coil are associated with a linear displacement of the shaft along the center axis of the shaft.

20. The medical device of claim 19, wherein:

the linear displacement of the shaft is in proportion to a force imparted to the shaft in a direction along the center axis of the shaft.

21. The medical device of claim 20, wherein:

the first coil and the second coil are secured to the mounting bracket such that the center axis of the shaft is centered between the center axis of the first rod and the center axis of the second rod.

22. The medical device of claim 20, wherein:

the center axis of the first rod and the center axis of the second rod are parallel to the center axis of the shaft.

23. The medical device of claim 19, wherein:

the first signal has a first frequency, and the second signal has a second frequency; and a microprocessor is configured to execute instructions to determine from the first frequency and the second frequency a measure of a force on the shaft along the center axis of the shaft.

24. The medical device of claim 18, wherein:

a center axis of the shaft is defined between the proximal end and the distal end of the shaft; and the first coil and the second coil are secured to the mounting bracket such that the center axis of the shaft is centered between the center axis of the first rod and the center axis of the second rod.

25. The medical device of claim 18, wherein:

the first coil has a first height, the second coil has a second height, and the first height is equal to the second height.

26. The medical device of claim 18, wherein:

a first signal generated by the first coil is associated with a position of the first magnet with reference to the first coil, and a second signal generated by the second coil is associated with a position of the second magnet with reference to the second coil; and the force sensor unit comprises a microprocessor coupled to receive the first and second signals.

27. The medical device of claim 18, wherein:

a center axis of the shaft is defined between the proximal end and the distal end of the shaft;

a first signal generated by the first coil is associated with a position of the first magnet with reference to the first coil, and a second signal generated by the second coil is associated with a position of the second magnet with reference to the second coil;

the first signal has a first frequency, and the second signal has a second frequency; and a microprocessor is configured to execute instructions to determine from the first frequency and the second frequency a measure of a force on the shaft along the center axis of the shaft.

28. The medical device of claim 1, wherein:

a center axis of the shaft is defined between the proximal end and the distal end of the shaft;

a first signal generated by the first coil is associated with a position of the first magnet with reference to the first coil, and a second signal generated by the second coil is associated with a position of the second magnet with reference to the second coil;

the first signal has a first frequency, and the second signal has a second frequency; and a microprocessor is configured to execute instructions to determine from the first frequency and the second frequency a measure of a force on the shaft along the center axis of the shaft.

* * * * *